United States Patent
Koenemann et al.

(10) Patent No.: US 8,658,290 B2
(45) Date of Patent: Feb. 25, 2014

(54) USE OF HALOGENATED PHTHALOCYANINES

(75) Inventors: Martin Koenemann, Mannheim (DE); Sudhakar Sundarraj, Singapore (SG); Jae Hyung Hwang, Mannheim (DE); Jan Schoeneboom, Mannheim (DE); Albert Liu, Palo Alto, CA (US); Peter Peumans, Sunnyvalle, CA (US); Felix Eickemeyer, Heidelberg (DE); Ingmar Bruder, Ludwigshafen (DE); Neil Gregory Pschirer, Mainz (DE); Ruediger Sens, Ludwigshafen (DE); Gerd Weber, Bad Duerkheim (DE); Sheeja Bahulayan, Singapore (SG); Peter Erk, Frankenthal (DE)

(73) Assignees: BASF SE, Ludwigshafen (DE); The Board of Trustees of the Leland Stanford Junior University, Palo Alto, CA (US)

( * ) Notice: Subject to any disclaimer, the term of this patent is extended or adjusted under 35 U.S.C. 154(b) by 325 days.

(21) Appl. No.: 12/738,947

(22) PCT Filed: Oct. 31, 2008

(86) PCT No.: PCT/EP2008/064796
§ 371 (c)(1),
(2), (4) Date: Apr. 20, 2010

(87) PCT Pub. No.: WO2009/056626
PCT Pub. Date: May 7, 2009

(65) Prior Publication Data
US 2010/0207114 A1    Aug. 19, 2010

Related U.S. Application Data

(60) Provisional application No. 60/984,175, filed on Oct. 31, 2007.

(51) Int. Cl.
*H01L 51/54* (2006.01)

(52) U.S. Cl.
USPC ........... 428/690; 428/917; 313/504; 313/505; 313/506; 257/40; 136/263; 540/122; 540/139; 540/140

(58) Field of Classification Search
USPC ................. 428/690, 917; 313/504, 505, 506; 257/40; 136/263; 540/122, 139, 140
See application file for complete search history.

(56) References Cited

U.S. PATENT DOCUMENTS

| 6,307,147 | B1 | 10/2001 | Bird et al. | |
| 2004/0067324 | A1* | 4/2004 | Lazarev et al. | 428/1.31 |

(Continued)

FOREIGN PATENT DOCUMENTS

| EP | 0 029 599 | 6/1981 |
| JP | 2-81479 | 3/1990 |

(Continued)

OTHER PUBLICATIONS

U.S. Appl. No. 13/119,192, filed Mar. 16, 2011, Koenemann, et al.

(Continued)

*Primary Examiner* — Gregory Clark
(74) *Attorney, Agent, or Firm* — Oblon, Spivak, McClelland, Maier & Neustadt, L.L.P.

(57) ABSTRACT

The present invention relates to the use of halogenated phthalocyanines as charge transport materials and/or as absorber materials.

20 Claims, 3 Drawing Sheets

16: metal electrode (cathode)

15: exciton blocking layer / electron transport layer (ETL)

14: electron transport layer (ETL)

13: mixed layer of hole-conducting material and electron transport material

12: hole transport layer ( HTL)

11: transparent conducting layer for anode

(56) References Cited

U.S. PATENT DOCUMENTS

| | | | |
|---|---|---|---|
| 2006/0060239 A1* | 3/2006 | Peumans et al. | 136/263 |
| 2006/0231954 A1 | 10/2006 | Yan et al. | |
| 2007/0190783 A1 | 8/2007 | Gomez et al. | |
| 2007/0259475 A1 | 11/2007 | Konemann et al. | |
| 2007/0269924 A1 | 11/2007 | Gomez et al. | |
| 2008/0009092 A1 | 1/2008 | Koenemann et al. | |
| 2008/0017850 A1 | 1/2008 | Koenemann et al. | |
| 2008/0035914 A1 | 2/2008 | Koenemann et al. | |
| 2008/0054258 A1 | 3/2008 | Koenemann et al. | |
| 2008/0087878 A1 | 4/2008 | Koenemann et al. | |
| 2008/0090325 A1 | 4/2008 | Koenemann et al. | |
| 2008/0268357 A1* | 10/2008 | Wada et al. | 430/66 |
| 2008/0269482 A1 | 10/2008 | Pschirer et al. | |
| 2008/0300405 A1 | 12/2008 | Konemann | |
| 2009/0078312 A1 | 3/2009 | Konemann et al. | |
| 2009/0166614 A1 | 7/2009 | Koenemann et al. | |
| 2009/0236591 A1 | 9/2009 | Koenemann et al. | |
| 2010/0048904 A1 | 2/2010 | Koenemann et al. | |
| 2010/0059716 A1 | 3/2010 | Qu et al. | |
| 2010/0072438 A1 | 3/2010 | Qu et al. | |

FOREIGN PATENT DOCUMENTS

| | | | |
|---|---|---|---|
| JP | 08 199161 | 8/1996 | |
| JP | 10-213912 | * 11/1998 | G03G 5/05 |
| JP | 11-251601 | 9/1999 | |
| JP | 2007-134503 | 5/2007 | |
| JP | 2007-242836 | 9/2007 | |
| WO | WO 2007/093643 | 8/2007 | |
| WO | 2008 003760 | 1/2008 | |

OTHER PUBLICATIONS

Pietro, J. William, "Rectifying Junctions Based on Metal-lophthalocyanine Thin Films", Advanced Materials, vol. 6, No. 3, pp. 239-242, XP000429161, ISSN: 0935-9648, Mar. 1, 1994.

Reddy, Venugopala K.R. et al., "Synthesis, spectral, magnetic and thermal studies on symmetrically substituted metal (II) 1,3,8,10,15,17,22,24-octachlorophthalocyanines", Dyes and Pigments, vol. 59, No. 3, pp. 237-244, XP004454402, ISSN: 0143-7208, Dec. 1, 2003.

Achar, B.N. et al., "Synthetic metals" based on nickel(II) 2,9,16,23-tetrahalo-substituted phthalocyanine derivatives, Synthetic Metals, vol. 114, pp. 219-224, (2000).

Murdey, Richard et al., "Frontier Electronic Structures in Fluorinated Copper Phthalocyanine Thin Films Studied Using Ultraviolet and Inverse Photoemission Spectroscopies", Mol. Cryst. Liq. Cryst., vol. 455, pp. 211-218, ISSN: 1542-1406, (2006).

Anderson L. Teresa et al., "Rectifying Junctions in Peripherally-Substituted Metallophthalocyanine Bilayer Films", J. Phys. Chem., vol. 97, pp. 6577-6578, (1993).

Mayer, T. et al., "Silicon-organic pigment material hybrids for photovoltaic application", Solar Energy Materials and Solar Cells, vol. 91, pp. 1873-1886, (2007).

U.S. Appl. No. 12/296,312, filed Oct. 7, 2008, Koenemann, et al.
U.S. Appl. No. 11/417,149, filed May 4, 2006, Koenemann, et al.
U.S. Appl. No. 12/593,097, filed Sep. 25, 2009, Gessner, et al.
U.S. Appl. No. 12/666,127, filed Dec. 22, 2009, Koenemann, et al.
U.S. Appl. No. 12/668,975, filed Jan. 13, 2010, Pschirer, et al.
U.S. Appl. No. 12/670,036, filed Jan. 21, 2010, Pschirer, et al.
U.S. Appl. No. 12/673,908, filed Feb. 17, 2010, Koenemann, et al.
U.S. Appl. No. 12/673,905, filed Feb. 17, 2010, Rennig, et al.
U.S. Appl. No. 13/322,210, filed Nov. 23, 2011, Sundarraj, et al.

Translation of the Notification of Reasons for Refusal, JP Pat. Appl. No. 2010-531533.

Wesley M. Sharman et al., American Chemical Society, 2005, vol. 16, pp. 1166-1185.

Zhang et al., Journal of the Chemical Society, Faraday Transactions, 1993, vol. 89, pp. 3347-3351.

Xu, Applied Physics Letter, 2004, vol. 85, No. 23, pp. 5757-5759, Asymmetric tandem organic photovoltaic cells with hybrid planar-mixed molecular heterojunctions.

* cited by examiner

16: metal electrode (cathode)

15: exciton blocking layer / electron transport layer (ETL)

14: electron transport layer (ETL)

13: mixed layer of hole-conducting material and electron transport material

12: hole transport layer (HTL)

11: transparent conducting layer for anode

Fig. 3

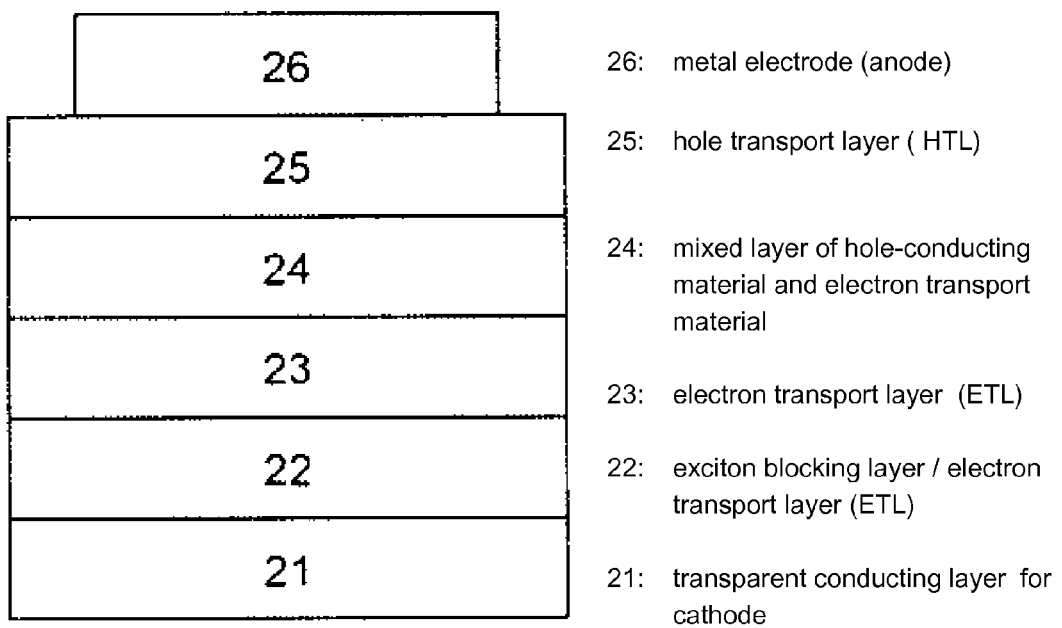

26: metal electrode (anode)

25: hole transport layer (HTL)

24: mixed layer of hole-conducting material and electron transport material

23: electron transport layer (ETL)

22: exciton blocking layer / electron transport layer (ETL)

21: transparent conducting layer for cathode

Fig. 4

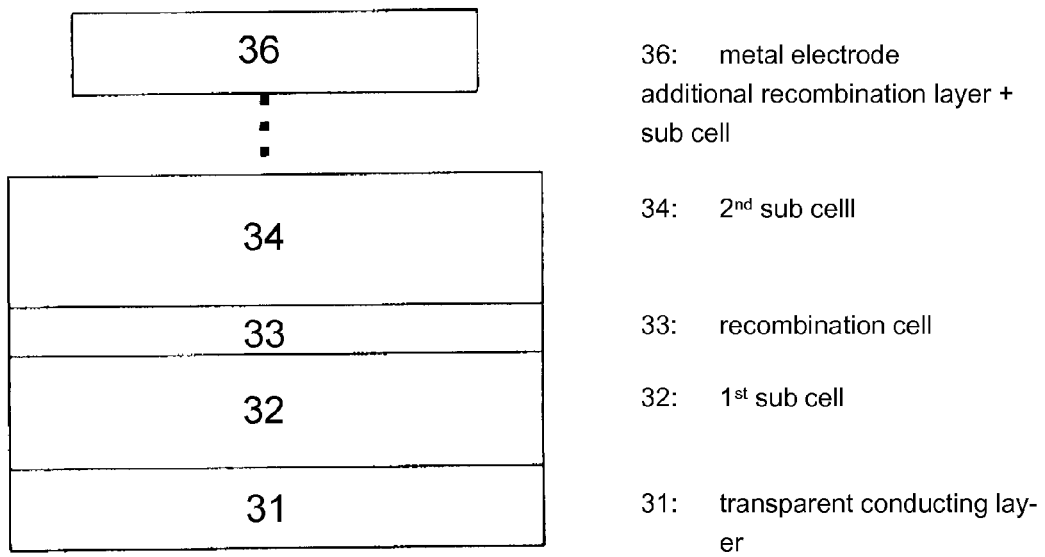

36: metal electrode
additional recombination layer + sub cell

34: 2nd sub celll

33: recombination cell

32: 1st sub cell

31: transparent conducting layer (a)   (b)

USE OF HALOGENATED PHTHALOCYANINES

The present invention relates to the use of halogenated phthalocyanines as charge transport materials or as absorber materials.

It is expected that, in the future, not only the classical inorganic semiconductors but increasingly also organic semiconductors based on low molecular weight or polymeric materials will be used in many sectors of the electronics industry. In many cases, these organic semiconductors have advantages over the classical inorganic semiconductors, for example better substrate compatibility and better processability of the semiconductor components based on them. They allow processing on flexible substrates and enable their interface orbital energies to be adjusted precisely to the particular application sector by the methods of molecular modeling. The significantly reduced costs of such components have brought a renaissance to the field of research of organic electronics. "Organic electronics" is concerned principally with the development of new materials and manufacturing processes for the production of electronic components based on organic semiconductor layers. These include in particular organic field-effect transistors (OFETs) and organic light-emitting diodes (OLEDs), and photovoltaics. Great potential for development is ascribed to organic field-effect transistors, for example in memory elements and integrated optoelectronic devices. Organic light-emitting diodes (OLEDs) exploit the property of materials of emitting light when they are excited by electrical current. OLEDs are particularly of interest as alternatives to cathode ray tubes and liquid-crystal displays for producing flat visual display units. Owing to the very compact design and the intrinsically lower power consumption, devices which comprise OLEDs are suitable especially for mobile applications, for example for applications in cell phones, laptops, etc.

The direct conversion of solar energy to electrical energy in solar cells is based on the internal photo effect of a semiconductor material, i.e. the generation of electron hole pairs by absorption of photons and the separation of the negative and positive charge carriers at a p-n transition. The photovoltage thus generated can bring about a photocurrent in an external circuit, through which the solar cell delivers its power.

The semiconductor can absorb only those photons which have an energy which is greater than its band gap. The size of the semiconductor band gap thus determines the proportion of sunlight which can be converted to electrical energy. It is expected that, in the future, organic solar cells will outperform the classical solar cells based on silicon owing to lower costs, a lower weight, the possibility of producing flexible and/or colored cells, the better possibility of fine adjustment of the band gap. There is thus a great demand for organic semiconductors which are suitable for producing organic solar cells.

Solar cells normally consist of two absorbing materials with different band gaps in order to utilize solar energy very effectively. The first organic solar cells, for example, consisted of a two-layer system composed of a copper phthalocyanine as a p-conductor and perylene-3,4:9,10-tetracarboxylic acid bisbenzimidazole (PTCBI) as an n-conductor and exhibited an efficiency of 1%. The efficiency of a solar cell depends upon its open-circuit voltage ($V_{OC}$). It indicates the maximum voltage of the irradiated cell with an open circuit. Further important parameters are the short-circuit current density ($J_{SC}$), the filling factor (FF) and the efficiency ($\eta$).

US 2006/0231954 relates to an electric contact material comprising heterojunctions, wherein the material is composed of electron-type organic semiconductors, hole-type organic semiconductors and heterojunctions made thereof. The hole-type organic semiconductor layer comprises at least one compound selected from copper phthalocyanine, nickel phthalocyanine, zinc phthalocyanine, cobalt phthalocyanine, platinum phthalocyanine, and metal-free phthalocyanine; the electron-type organic semiconductor layer comprises at least one compound selected from copper hexadecafluorophthalocyanine, zinc hexadecafluoro-phthalocyanine, iron hexadecafluorophthalocyanine and cobalt hexadecafluoro-phthalocyanine.

EP 0 921 579 A2 discloses thin film transistors based on coordination compounds of substituted phthalocyanines with copper, zinc, tin, iron or hydrogen, wherein the substituents are electron-withdrawing substituents. At least one of the six-membered rings of the phthalocyanines has a chlorine or fluorine substituent. However, coordination compounds of substituted phthalocyanines having 1 to 12 halogen substituents are not disclosed. All coordination compounds of substituted phthalocyanines concretely disclosed carry sixteen chlorine or fluorine substituents.

Synthetic Materials 114 (2000) 219-224 relates to nickel (II) 2,9,16,23-tetrahalo-substituted phthalocyanine complexes and their doping with iodine as well as to the electrical conductivity of these complexes.

In Mol. Cryst. Liq. Cryst (2006), Vol. 455, pages 211-218, R. Murdey et al. describe the electronic structures of copper phthalocyanine, copper octafluorophthalocyanine and copper hexadecafluorophthalocyanine thin films.

J. Phys. Chem. 1993, 97, 6577-6578 refers to metallophthalocyanine bilayer films and their behaviour toward an applied DC voltage. The bilayers studied are $Cu(PcF_8)/Cu(Pc)$, $Cu(PcF_8)/Ni(Pc)$ and $Cu(Pc)/Ni(Pc)$. No concrete substitution patterns of the fluorinated copper phthalocyanines are disclosed.

In Solar Energy Materials & Solar Cells 91, 2007, 1873-1886, the optoelectronic interactions of a hybrid inorganic-organic system comprising silicon and zinc phthalocyanines optionally substituted by 4, 8 or 12 fluorine atoms has been studied for possible application as photovoltaic material in dye-sensitized thin film solar cells.

U.S. Pat. No. 6,307,147 relates to organic dyes for photovoltaic cells and for photoconductive electrophotography systems. The photovoltaic cell comprises a compound of formula A

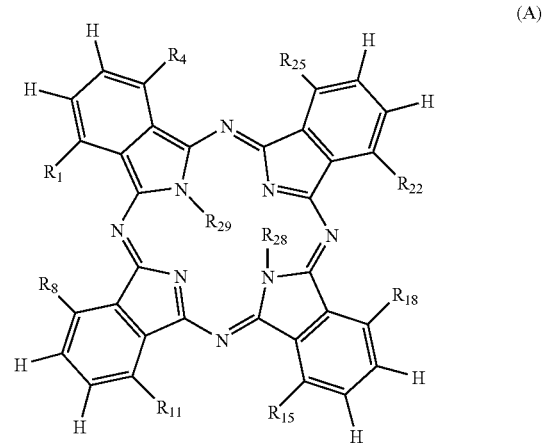

(A)

wherein $R_1$, $R_4$, $R_8$, $R_{11}$, $R_{15}$, $R_{18}$, $R_{22}$, and $R_{25}$ are selected from the group consisting of hydrogen, fluorine, chlorine, methoxy, methyl, ethyl and cyano; wherein $R_{31}$ and $R_{29}$ are both hydrogen or together are a metal ion having a double positive charge or a metal ion plus non-metal atom or group bound to the metal ion, and having overall a double positive charge; and wherein $R_1$, $R_4$, $R_{15}$, and $R_{18}$ are the same and are a first substituent, and $R_8$, $R_{11}$, $R_{22}$ and $R_{25}$ are the same and are a second substituent which is different from said first substituent.

WO 2008/003760 discloses the use of copper phthalocyanines having a chlorination degree of at least 12 as air-stable n-type organic semiconductors.

It has now been found that, surprisingly, halogenated phthalocyanines having up to 12 halogen atoms on the phthalocyanine skeleton are particularly advantageously suitable as charge transport materials and/or absorber materials. They are suitable especially as semiconductor materials, especially for organic photovoltaics (OPVs) and in organic field-effect transistors (OFETs). They provide organic photovoltaic cells with higher open circuit voltage $V_{OC}$ than metal-free and metal containing unsubstituted phthalocyanines, when paired with the same complementary semiconductor material.

The present invention therefore relates firstly to the use of compounds of the general formula Ia and Ib

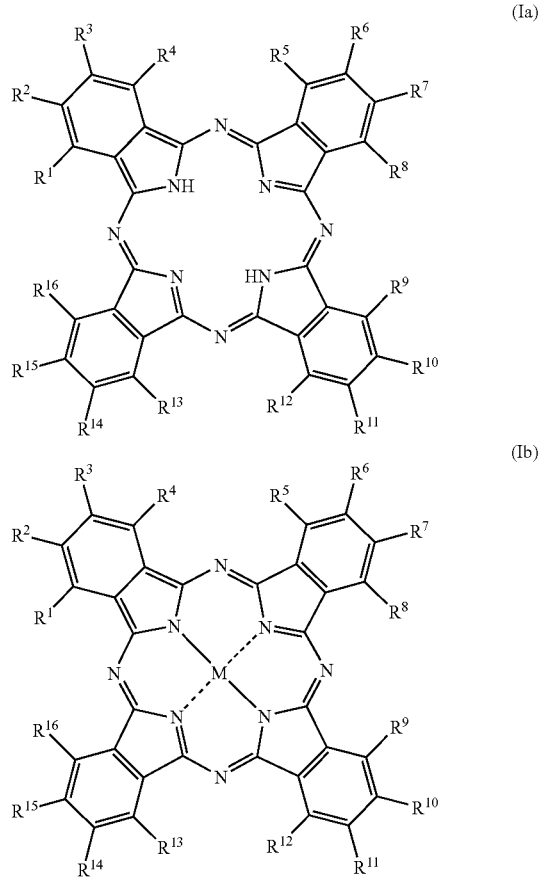

where
from one to twelve, e.g. 1, 2, 3, 4, 5, 6, 7, 8, 9, 10, 11 or 12, of the radicals $R^1$ to $R^{16}$ are each halogen and the others are each hydrogen, and
M in the formula Ib is a divalent metal, a divalent metal atom containing group or a divalent metalloid group
as charge transport materials and/or as absorber materials.

According to a special embodiment, the compound of the formula Ib is not copper dodecachlorophthalocyanine (CuPcCl$_{12}$).

According to a special embodiment, the compound of formula Ib is not copper octafluorophthalocyanine (CuPcF8), wherein $R^2$, $R^3$, $R^6$, $R^7$, $R^{10}$, $R^{11}$, $R^{14}$ and $R^{15}$ are fluorine and $R^1$, $R^4$, $R^5$, $R^8$, $R^9$, $R^{12}$, $R^{13}$ and $R^{16}$ are hydrogen. According to a broader special embodiment, the compound of the formula Ib is not copper octafluorophthalocyanine (CuPcF$_8$).

According to a further special embodiment, the compound of the formulae Ia and Ib is not a compound, wherein $R^1$, $R^4$, $R^9$ and $R^{12}$ are chlorine or fluorine and $R^2$, $R^3$, $R^5$, $R^6$, $R^7$, $R^8$, $R^{10}$, $R^{11}$, $R^{13}$, $R^{14}$, $R^{15}$ and $R^{16}$ each are hydrogen.

According to a further special embodiment, the organic solar cell does not comprise a compound of the formula Ib, wherein M is Cu, $R^2$, $R^3$, $R^6$, $R^7$, $R^{10}$, $R^{11}$, $R^{14}$ and $R^{15}$ are each fluorine and $R^1$, $R^4$, $R^5$, $R^8$, $R^9$, $R^{12}$, $R^{13}$ and $R^{16}$ are each hydrogen in combination with a further semiconductor material selected from copper phthalocyanine and nickel phthalocyanine.

According to a further special embodiment, the organic solar cell does not comprise a compound of the formulae Ia or Ib, wherein $R^1$, $R^4$, $R^9$ and $R^{12}$ are chlorine or fluorine and $R^2$, $R^3$, $R^5$, $R^6$, $R^7$, $R^8$, $R^{10}$, $R^{11}$, $R^{13}$, $R^{14}$, $R^{15}$ and $R^{16}$ each are hydrogen in combination with zinc hexadecafluorophthalocyanine.

The present invention furthermore relates to the use of compounds of formulae Ia and Ib as a semiconductor material in organic photovoltaics or as a semiconductor material in organic field-effect transistors.

The present invention furthermore relates to the use of compounds of formulae Ia and Ib as a charge transfer material in organic photovoltaics.

The present invention furthermore relates to the use of compounds of formulae Ia and Ib as a charge transfer material in organic light-emitting diodes.

The present invention furthermore relates to the use of compounds of formulae Ia and Ib as electron donor and a compound selected from fullerenes, fullerene derivatives and rylene compounds as electron acceptor in a photoactive layer of an organic solar cell.

The present invention furthermore relates to the use of compounds of formulae Ia and Ib as electron donor and a compound selected from fullerenes, fullerene derivatives and rylene compounds as electron acceptor in a photoactive layer of an organic solar cell having donor-acceptor junctions in the form of a bulk-heterojunction.

The present invention furthermore relates to the use of compounds of formulae Ia and Ib as electron donor and a compound selected from fullerenes, fullerene derivatives and rylene compounds as electron acceptor in a photoactive layer of an organic solar cell having donor-acceptor junctions in the form of a flat junction.

Furthermore, the present invention relates to an organic solar cell comprising a substrate having at least one cathode, at least one anode and at least one compound of the formulae Ia and/or Ib as a photoactive material. Furthermore, the present invention relates to an organic solar cell, wherein the compound of the formulae Ia and/or Ib and/or a further different semiconductor material is used in combination with at least one dopant, especially selected from pyronin B, rhodamine, 3,6-difluoro-2,5,7,7,8,8-hexacyanoquinodimethane and combinations thereof.

Furthermore, the present invention relates to an organic solar cell in the form of a tandem cell containing a subcell, which comprises at least one compound of formulae Ia and/or Ib and at least one fullerene or fullerene derivative, especially C60.

Furthermore, the present invention relates to an organic field-effect transistor comprising a substrate having at least one gate structure, a source electrode and a drain electrode and at least one compound of the formula Ia and/or Ib as a semiconductor.

Furthermore, the present invention relates to a substrate having a multitude of organic field-effect transistors, wherein at least some of the field-effect transistors comprise at least one compound of the formulae Ia and/or Ib as an n-semiconductor.

Furthermore, the present invention relates to an OLED comprising at least one compound of the formulae Ia and/or Ib.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein:

FIG. 3 illustrates a solar cell with an inversion structure; and

FIG. 4 illustrates a tandem cell.

Figure 1:
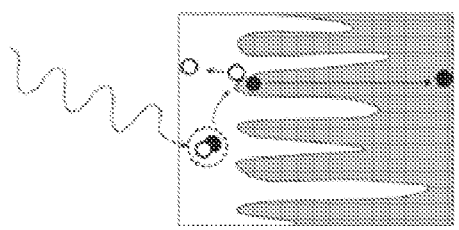
FIG. 1 shows a nearly perfect morphology of a bulk-heterojunction.

Halogen is iodine, bromine, chlorine or fluorine, particularly chlorine or fluorine.

In the context of the present invention, the expression "alkyl" comprises straight-chain or branched alkyl. It is preferably straight-chain or branched $C_1$-$C_{30}$-alkyl, especially $C_1$-$C_{20}$-alkyl and most preferably $C_1$-$C_{12}$-alkyl. Examples of alkyl groups are especially methyl, ethyl, n-propyl, isopropyl, n-butyl, isobutyl, sec-butyl, tert-butyl, n-pentyl, n-hexyl, n-heptyl, n-octyl, n-nonyl, n-decyl, n-undecyl, n-dodecyl, n-tridecyl, n-tetradecyl, n-hexadecyl, n-octadecyl and n-eicosyl.

The expression alkyl also comprises alkyl radicals whose carbon chains may be interrupted by one or more nonadjacent groups which are selected from —O—, —S—, —NR$^e$—, —C(=O)—, —S(=O)— and/or —S(=O)$_2$—. R$^e$ is preferably hydrogen, alkyl, cycloalkyl, heterocycloalkyl, aryl or hetaryl. The expression alkyl also comprises substituted alkyl radicals. Substituted alkyl groups may, depending on the length of the alkyl chain, have one or more (e.g. 1, 2, 3, 4, 5 or more than 5) substituents. These are preferably each independently selected from cycloalkyl, heterocycloalkyl, aryl, hetaryl, halogen, hydroxyl, thiol, COOH, carboxylate, SO$_3$H, sulfonate, NE$^1$E$^2$, nitro and cyano, where E$^1$ and E$^2$ are each independently hydrogen, alkyl, cycloalkyl, heterocycloalkyl, aryl or hetaryl. Halogen substituents are preferably fluorine, chlorine or bromine.

Carboxylate and sulfonate are, respectively, a derivative of a carboxylic acid function or a sulfonic acid function, especially a metal carboxylate or sulfonate, a carboxylic ester or sulfonic ester function or a carboxamide or sulfonamide function. Cycloalkyl, heterocycloalkyl, aryl and hetaryl substituents of the alkyl groups may in turn be unsubstituted or substituted; suitable substituents are those specified below for these groups.

The above remarks regarding alkyl also apply to the alkyl moiety in alkoxy.

In the context of the present invention, the expression "cycloalkyl" comprises unsubstituted or substituted cycloalkyl groups, preferably $C_3$-$C_8$-cycloalkyl groups such as cyclopropyl, cyclobutyl, cyclopentyl, cyclohexyl, cycloheptyl or cyclooctyl, especially $C_5$-$C_8$-cycloalkyl. Substituted cycloalkyl groups may have one or more (e.g. 1, 2, 3, 4, 5 or more than 5) substituents. These are preferably each independently selected from alkyl and the substituents specified above for the alkyl groups. In the case of substitution, the cycloalkyl groups preferably bear one or more, for example one, two, three, four or five, $C_1$-$C_6$-alkyl groups.

In the context of the present invention, the expression "aryl" comprises mono- or polycyclic aromatic hydrocarbon radicals which may be unsubstituted or substituted. Aryl is preferably unsubstituted or substituted phenyl, naphthyl, indenyl, fluorenyl, anthracenyl, phenanthrenyl, naphthacenyl, chrysenyl, pyrenyl, etc., and more preferably phenyl or naphthyl. Substituted aryls may, depending on the number and size of their ring systems, have one or more (e.g. 1, 2, 3, 4, 5 or more than 5) substituents. They are preferably each independently selected from alkyl, alkoxy, cycloalkyl, heterocycloalkyl, aryl, hetaryl, halogen, hydroxyl, thiol, COOH, carboxylate, SO$_3$H, sulfonate, NE$^5$E$^6$, nitro and cyano, where E$^5$ and E$^6$ are each independently hydrogen, alkyl, cycloalkyl, heterocycloalkyl, aryl or hetaryl. Halogen substituents are preferably fluorine, chlorine or bromine. Aryl is more preferably phenyl which, in the case of substitution, may bear generally 1, 2, 3, 4 or 5, preferably 1, 2 or 3 substituents.

Aryl which bears one or more radicals is, for example, 2-, 3- and 4-methylphenyl, 2,4-, 2,5-, 3,5- and 2,6-dimethylphenyl, 2,4,6-trimethylphenyl, 2-, 3- and 4-ethyl-phenyl, 2,4-, 2,5-, 3,5- and 2,6-diethylphenyl, 2,4,6-triethylphenyl, 2-, 3- and 4-propyl-phenyl, 2,4-, 2,5-, 3,5- and 2,6-dipropylphenyl, 2,4,6-tripropylphenyl, 2-, 3- and 4-isopropylphenyl, 2,4-, 2,5-, 3,5- and 2,6-diisopropylphenyl, 2,4,6-triisopropylphenyl, 2-, 3- and 4-butylphenyl, 2,4-, 2,5-, 3,5- and 2,6-dibutylphenyl, 2,4,6-tributylphenyl, 2-, 3- and 4-isobutylphenyl, 2,4-, 2,5-, 3,5- and 2,6-diisobutylphenyl, 2,4,6-triisobutylphenyl, 2-, 3- and 4-sec-butylphenyl, 2,4-, 2,5-, 3,5- and 2,6-di-sec-butylphenyl, 2,4,6-tri-sec-butylphenyl, 2-, 3- and 4-tert-butylphenyl, 2,4-, 2,5-, 3,5- and 2,6-di-tert-butylphenyl and 2,4,6-tri-tert-butylphenyl; 2-, 3- and 4-methoxyphenyl, 2,4-, 2,5-, 3,5- and 2,6-dimethoxyphenyl, 2,4,6-trimethoxyphenyl, 2-, 3- and 4-ethoxyphenyl, 2,4-, 2,5-, 3,5- and 2,6-diethoxyphenyl, 2,4,6-triethoxyphenyl, 2-, 3- and 4-propoxyphenyl, 2,4-, 2,5-, 3,5- and 2,6-dipropoxyphenyl, 2-, 3- and 4-isopropoxyphenyl, 2,4-, 2,5-, 3,5- and 2,6-diisopropoxyphenyl and 2-, 3- and 4-butoxyphenyl; 2-, 3- and 4-cyanophenyl.

The above remarks regarding aryl also apply to the ary moiety in aryloxy.

In the context of the present invention, the expression "heterocycloalkyl" comprises nonaromatic, unsaturated or fully saturated, cycloaliphatic groups having generally from 5 to 8 ring atoms, preferably 5 or 6 ring atoms, in which 1, 2 or 3 of the ring carbon atoms are replaced by heteroatoms selected from oxygen, nitrogen, sulfur and an —NR$^e$— group and which is unsubstituted or substituted by one or more, for example 1, 2, 3, 4, 5 or 6 $C_1$-$C_6$-alkyl groups. Examples of such heterocycloaliphatic groups include pyrrolidinyl, piperidinyl, 2,2,6,6-tetramethylpiperidinyl, imidazolidinyl, pyrazolidinyl, oxazolidinyl, morpholidinyl, thiazolidinyl, isothiazolidinyl, isoxazolidinyl, piperazinyl-, tetrahydrothiophenyl, dihydrothien-2-yl, tetrahydrofuranyl, dihydrofuran-2-yl, tetrahydropyranyl, 1,2-oxazolin-5-yl, 1,3-oxazolin-2-yl and dioxanyl.

In the context of the present invention, the expression "heteroaryl" comprises unsubstituted or substituted, heteroaromatic, mono- or polycyclic groups, preferably the pyridyl, quinolinyl, acridinyl, pyridazinyl, pyrimidinyl, pyrazinyl, pyrrolyl, imidazolyl, pyrazolyl, indolyl, purinyl, indazolyl, benzotriazolyl, 1,2,3-triazolyl, 1,3,4-triazolyl and carbazolyl groups, where these heterocycloaromatic groups, in the case of substitution, may bear generally 1, 2 or 3 substituents. The substituents are preferably selected from $C_1$-$C_6$-alkyl, $C_1$-$C_6$-alkoxy, hydroxyl, carboxyl, halogen and cyano. As used herein a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher" HOMO or LUMO energy level appears closer to the top of such a diagram than a "lower" HOMO or LUMO energy level.

In the context of organic materials, the terms "donor" and "acceptor" refer to the relative positions of the HOMO and LUMO energy levels of two contacting but different organic materials. The term "electron donor" refers to the material's electron affinity. An electron donor material has a relative low electron affinity, i.e. the EA value has a smaller absolute value. As such, an electron donor material tends to act as a p-type material. In other words, an electron donor material may act as a hole transport material. The term "electron acceptor" refers to the material's electron affinity. An electron acceptor material has a relative high electron affinity. As such, an electron acceptor material tends to act as a n-type material. In other words, an electron acceptor material may act as an electron transport material.

The term "charge transport material" as used herein refers to a material which transports charge, i.e. holes or electrons. An electron donor material transports holes and an electron acceptor material transports electrons.

The term "photoactive layer" as used herein is a portion of a photosensitive device that absorbs electromagnetic radiation to generate excitons (i.e. electrically neutral excited state in form of electron-hole pairs).

In the compounds of formulae Ia and Ib, halogen substituents can be in the ortho- or meta-position of each 6-membered ring in the phthalocyanine ring. The two ortho positions on each 6-membered ring are marked by asterix (*) and the two meta positions on each 6-membered ring are marked by # in the formulae Ia and Ib below.

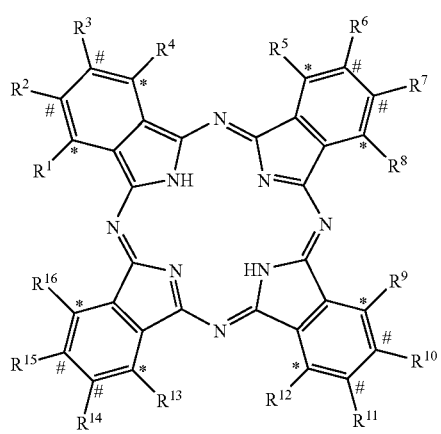

(Ia)

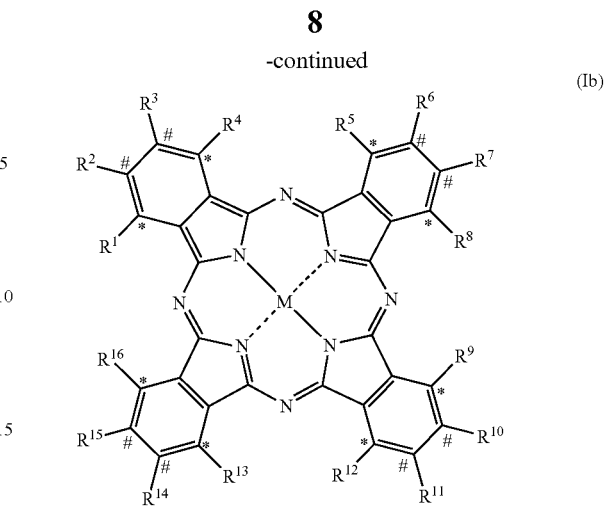

(Ib)

wherein $R^1$ to $R^{16}$ and M are as defined above.

Compounds of formula Ia and Ib, wherein each six-membered ring carries a halogen substituent in one of the ortho-positions are referred to as ortho-compounds. Compounds of formula Ia and Ib, wherein each six-membered ring carries a halogen substituent in one of the meta-positions are referred to as meta-compounds. Compounds of formula Ia and Ib, wherein each six-membered ring carries two halogen substituents in both ortho-positions are referred to as diortho-compounds. Compounds of formula Ia and Ib, wherein each six-membered ring carries two halogen substituents in both meta-positions are referred to as dimeta-compounds.

In one embodiment, preference is given to those compounds of the formulae Ia and Ib, wherein from one to ten, e.g. 1, 2, 3, 4, 5, 6, 7, 8, 9 or 10, especially two to ten, of the $R^1$ to $R^{16}$ radicals are each halogen and the others are each hydrogen. In a further embodiment, preference is given to those compounds of the formulae Ia and Ib, wherein from 1 to 8, e.g. 1, 2, 3, 4, 5, 6, 7 or 8, of the $R^1$ to $R^{16}$ radicals are each halogen and the others are each hydrogen.

In a further preferred embodiment, 4 of the $R^1$ to $R^{16}$ radicals are each halogen and the others are each hydrogen. In this embodiment, each six-membered ring preferably carries one halogen atom. According to a specific embodiment, each six-membered ring carries one halogen atom in the ortho-position. According to a further specific embodiment, each each six-membered ring carries one halogen atom in the meta-position. According to a further specific embodiment, two of the six-membered rings each carry one halogen atom in the ortho-position and the other two six-membered rings each carry one halogen atom in the meta-positions. According to a further specific embodiment, three of the six-membered rings each carry one halogen atom in the ortho-position and the other six-membered ring carries one halogen atom in the meta-position. According to a further specific embodiment, three of the six-membered rings each carry one halogen atom in the meta-position and the other six-membered ring carries one halogen atom in the ortho-position.

In a further preferred embodiment, 8 of the $R^1$ to $R^{16}$ radicals are each halogen and the others are each hydrogen. In this embodiment, each six-membered ring preferably carries two halogen atoms. They may be attached either in the ortho-position or in the two meta-position. In a further embodiment, two of the six-membered rings carry each two halogen atoms attached in the ortho-position and the other two six-membered rings each carry two halogen atoms attached in the meta-positions. According to a further specific embodiment, three of the six-membered rings each carry two halogen atom in the ortho-positions and the other six-membered ring carries two halogen atoms in the meta-position. According to a further specific embodiment, three of the six-membered rings each carry two halogen atoms in the meta-position and the other six-membered ring carries two halogen atoms in the meta-position.

The halogen radicals are preferably selected from F and Cl. In a preferred embodiment, in the compounds of the formulae Ia and Ib, the $R^1$ to $R^{16}$ radicals which are halogen are all F. In a further preferred embodiment, in the compounds of the formulae Ia and Ib the $R^1$ to $R^{16}$ radicals which are halogen are all Cl.

Divalent metals may, for example, be chosen from those of groups 2, 8, 10, 11, 12 and 14 of the Periodic Table. Divalent metals are, for example, Cu(II), Zn(II), Fe(II), Ni(II), Cd(II), Ag(II), Mg(II), Sn(II), or Pb (II).

A divalent metal atom containing group may, for example, be chosen from a divalent oxometal, a divalent hydroxymetal, or a divalent halogenometal moiety. In the divalent oxometal moiety, for example, the metal may be chosen from those of groups 4, 5, 7 and 14 of the Periodic Table. Examples of divalent oxometal moieties are V(IV)O, Mn(IV)O, Zr(IV)O, Sn(IV)O or Ti(IV)O. In a divalent hydroxymetal moiety, the metal may be chosen from those of groups 4, 6, 13, 14 and 15 of the Periodic Table. Examples of divalent hydroxymetal moieties are Al(III)OH, Cr(III)OH, Bi(III)OH, or Zr(IV)(OH)$_2$. In a divalent halogenometal moiety, the metal may be chosen from those of group 13 of the Periodic Table. Examples of divalent halogenometal moieties are for example, for example, Al(III)Cl, Al(III)F or In(III)Cl.

In divalent metalloid moieties, the metalloid may be chosen from a metalloid of group 14 of the Periodic Table, e.g. silicon. With a tetravalent metalloid, two of the valences may be satisfied by ligands such as hydrogen, hydroxy, halogen, e.g. fluorine or chlorine, alkyl, alkoxy, aryl or aryloxy. Examples of divalent metalloid moieties are SiH$_2$, SiF$_2$, SiCl$_2$, Si(OH)$_2$, Si(alkyl)$_2$, Si(aryl)$_2$, Si(alkoxy)$_2$ and Si(aryloxy)$_2$.

In the formula Ib, M is preferably Cu or Zn. Likewise, preference is given to compounds of formula Ib, wherein M is a divalent halogenometal moiety, preferably Al(III)Cl, Al(III)F or In(III)Cl.

Examples of octafluorinated and octachlorinated phthalocyanines are the following:

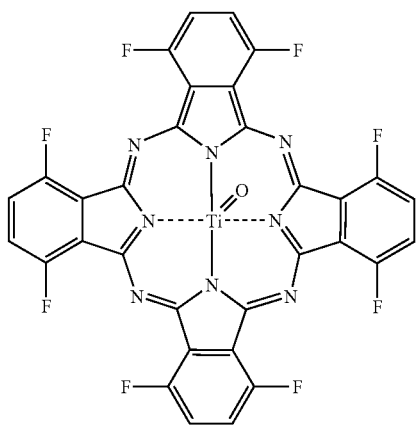

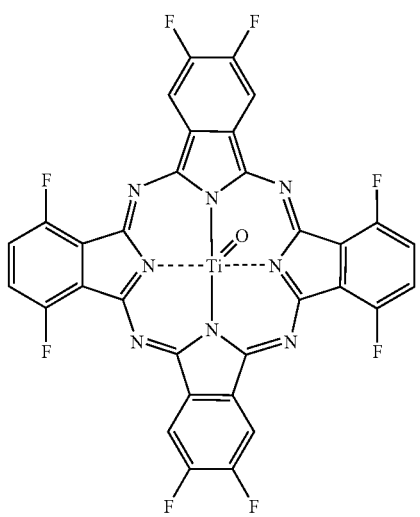

-continued

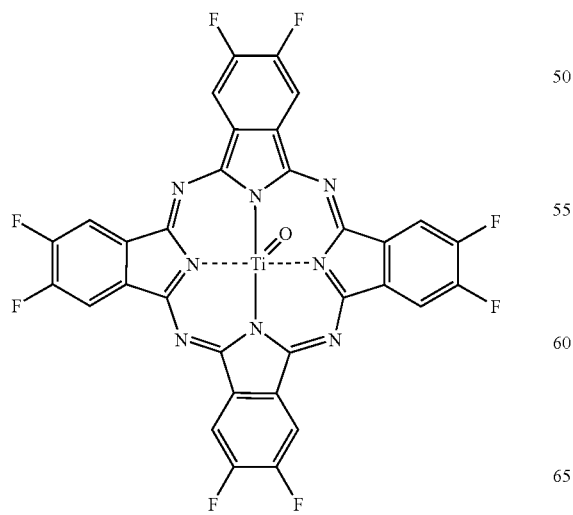

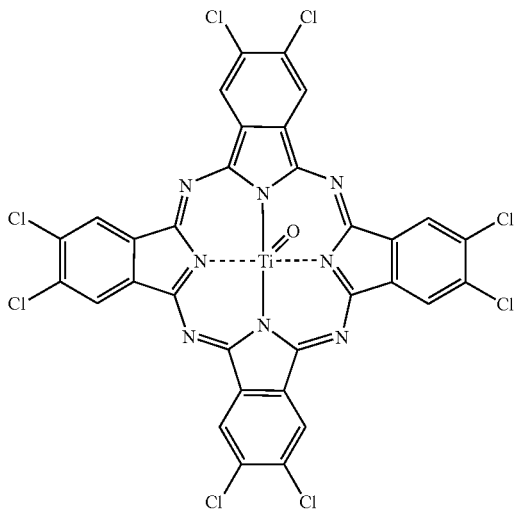

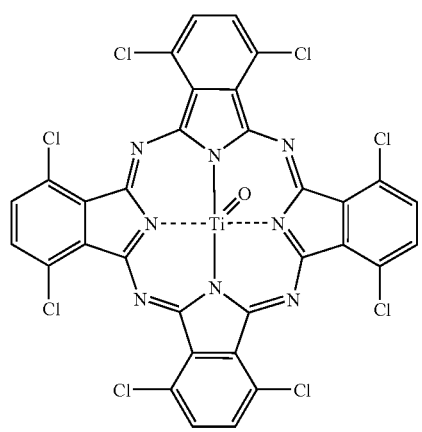
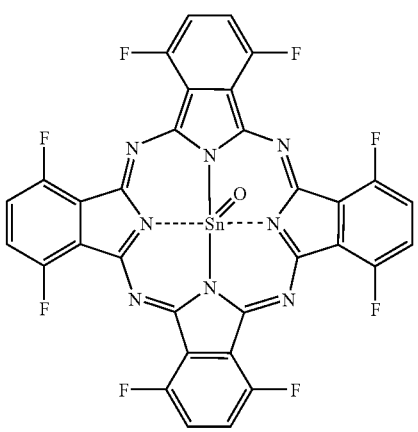
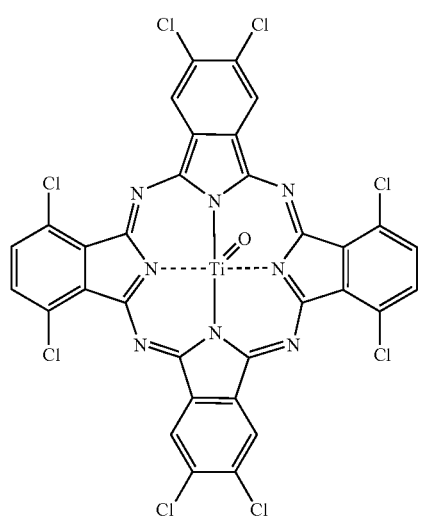
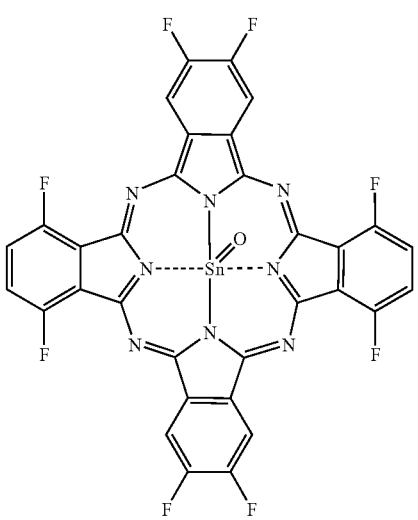
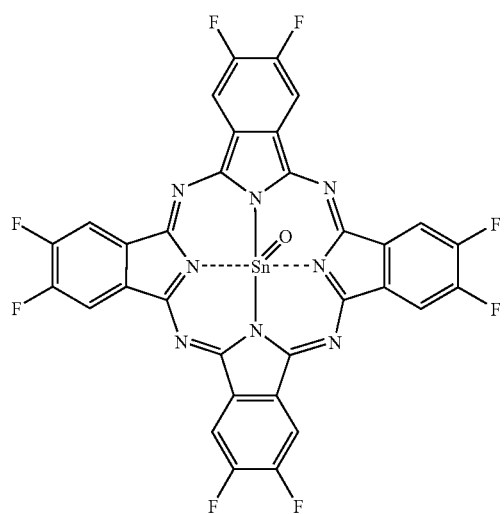
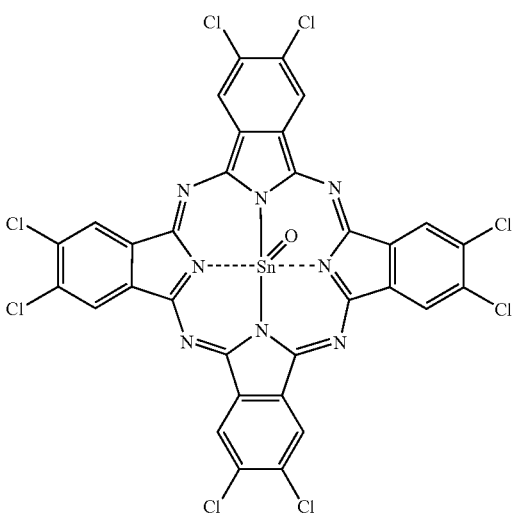

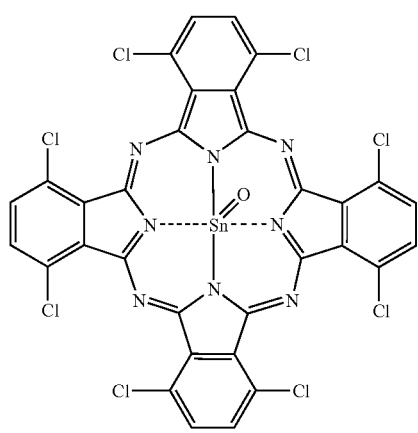
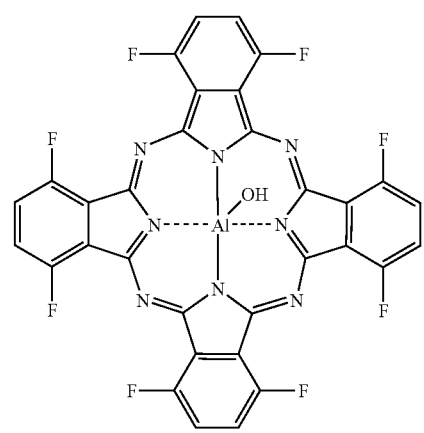
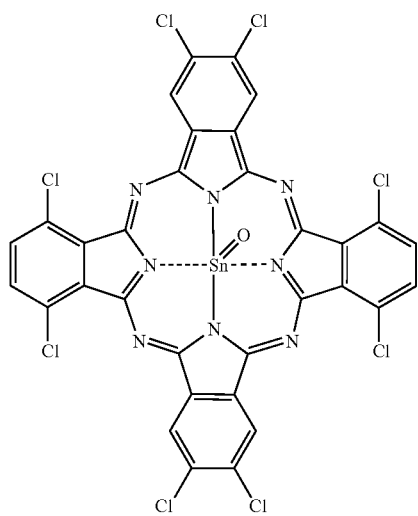
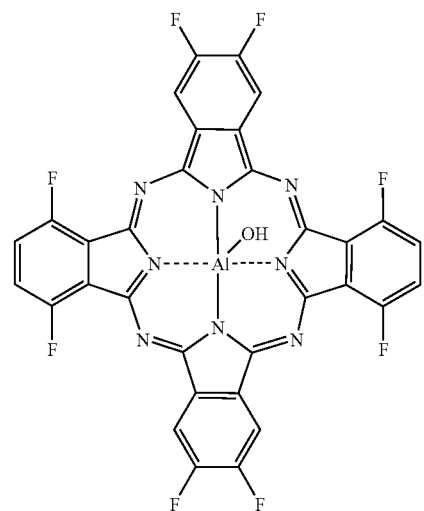
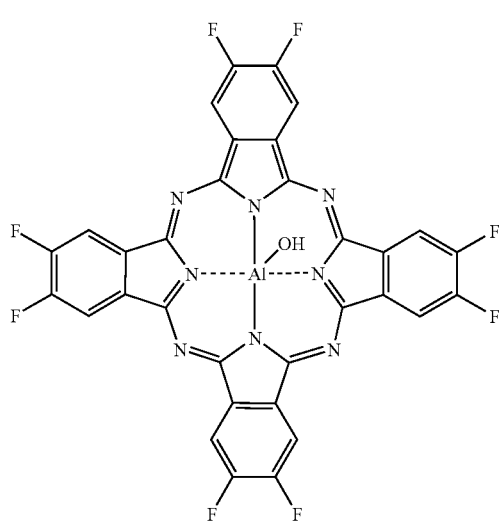
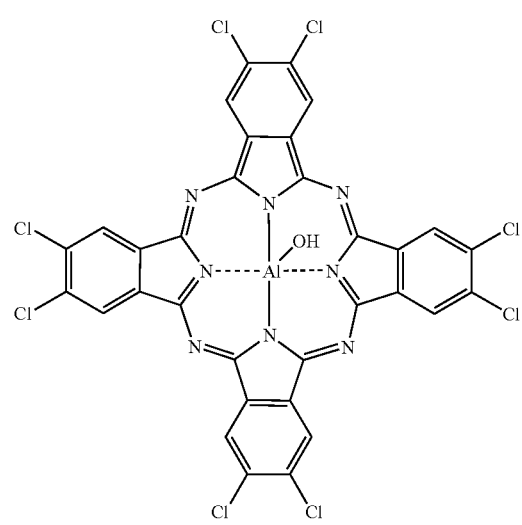

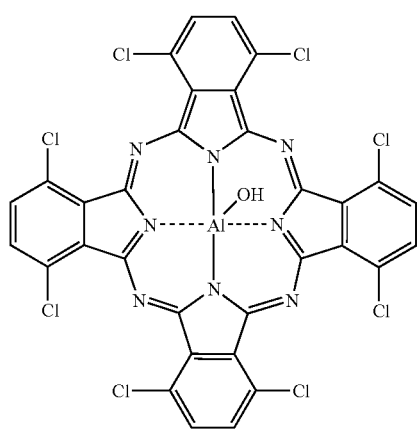
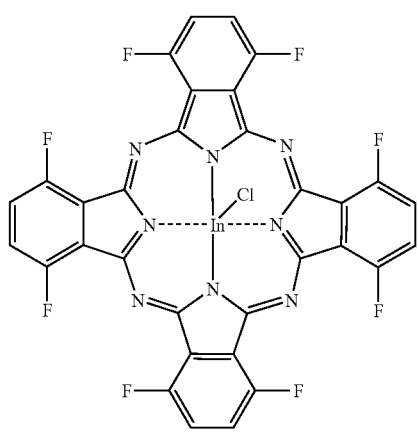
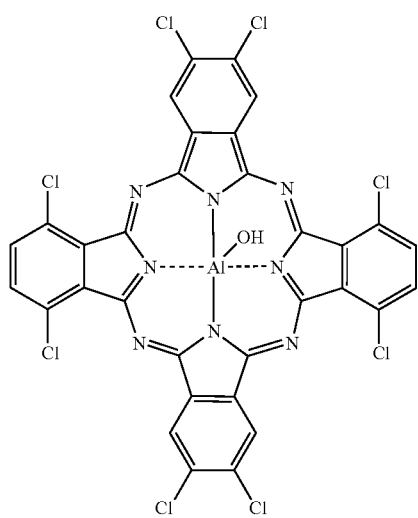
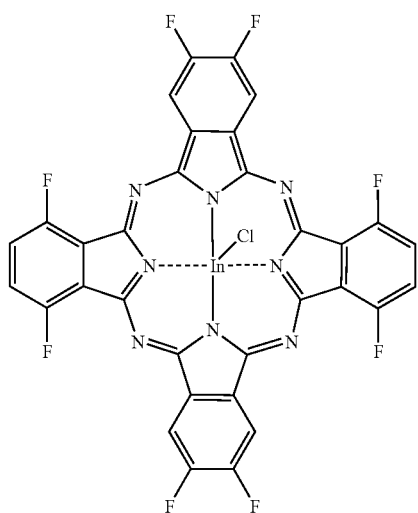
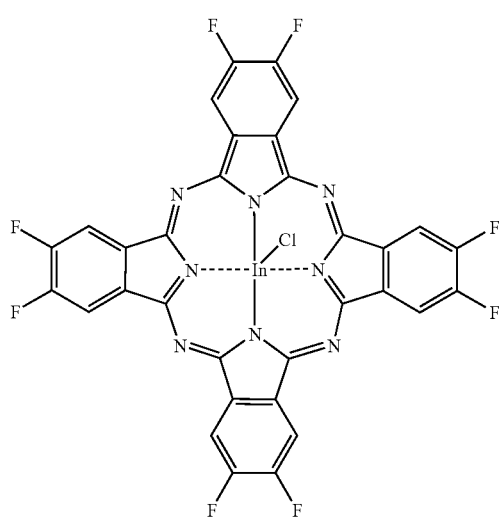
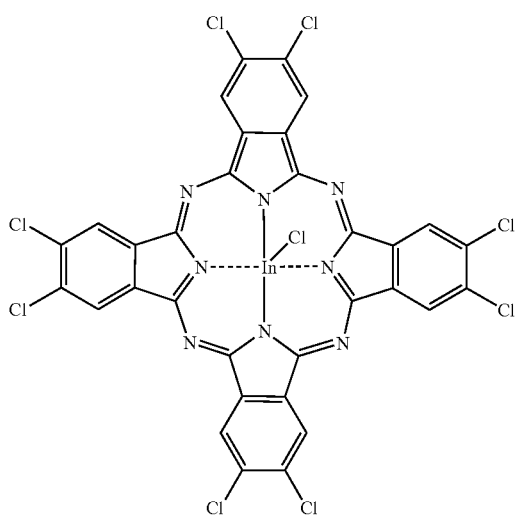

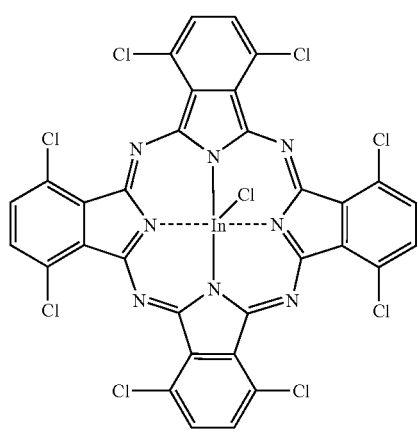
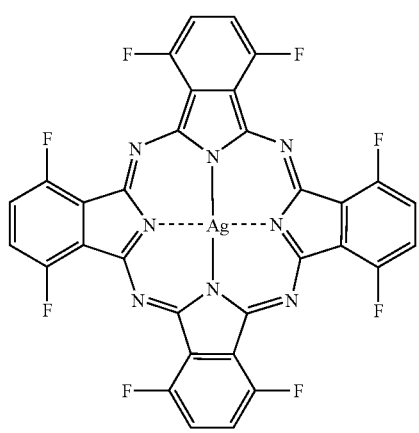
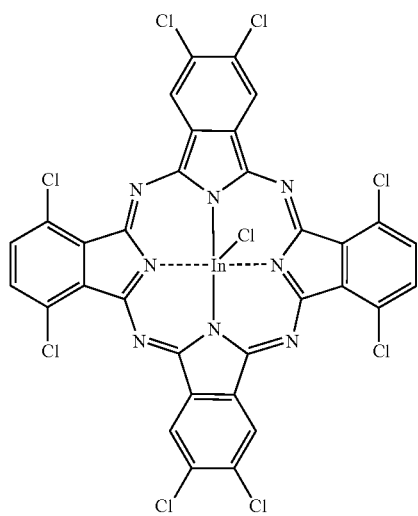
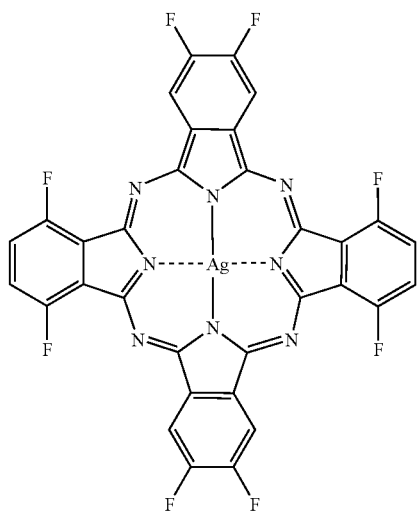
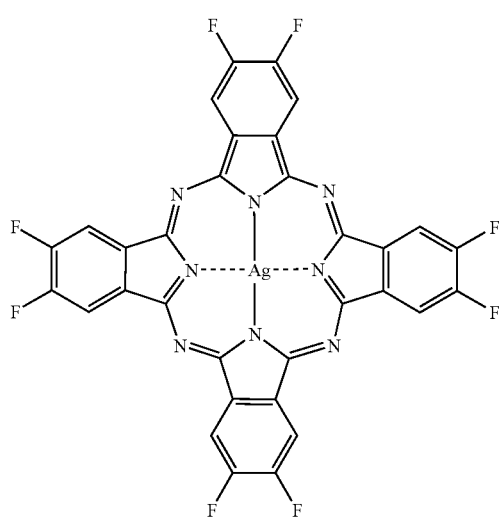
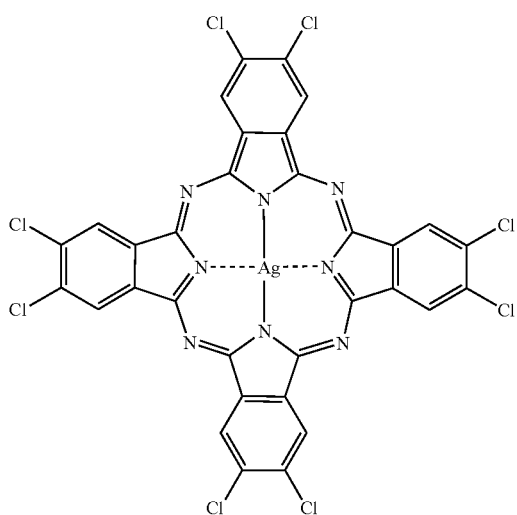

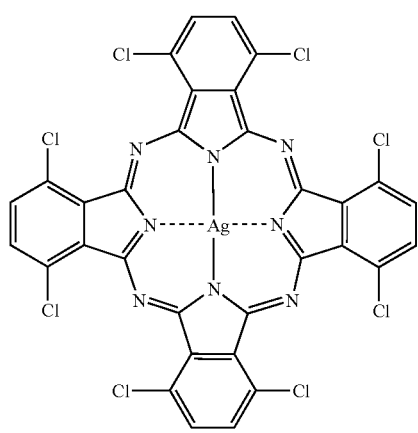
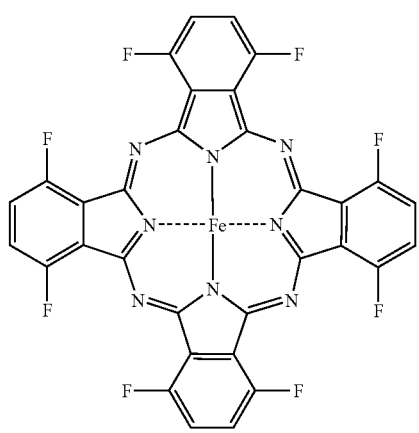
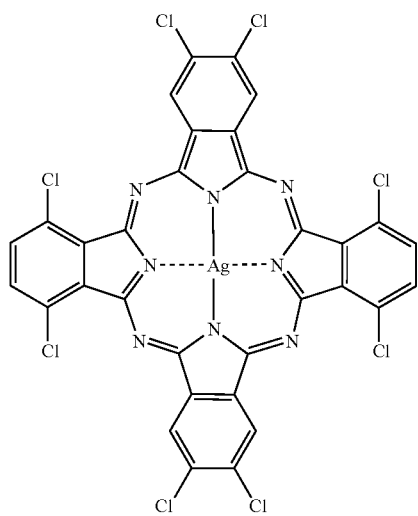
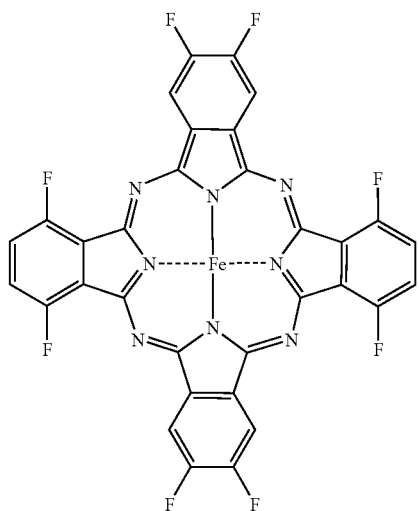
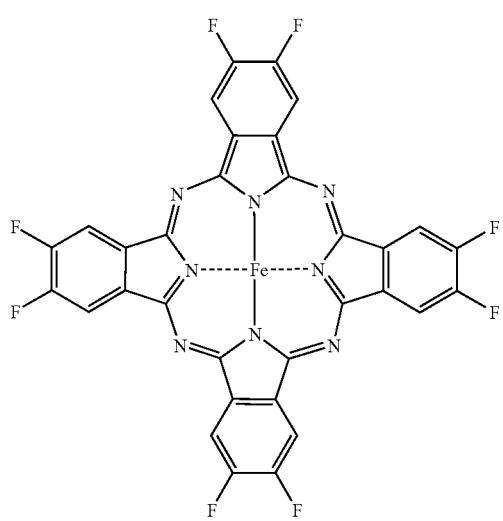
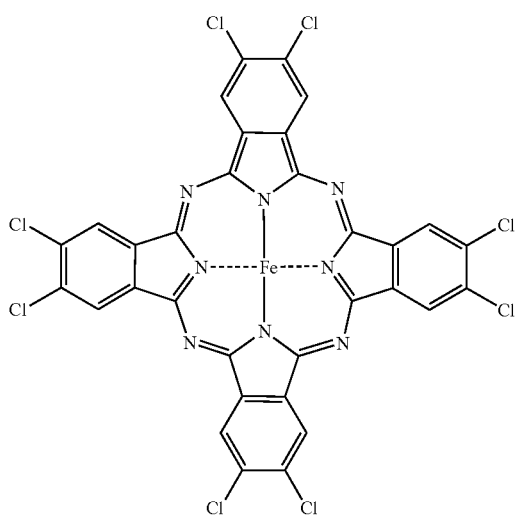

-continued
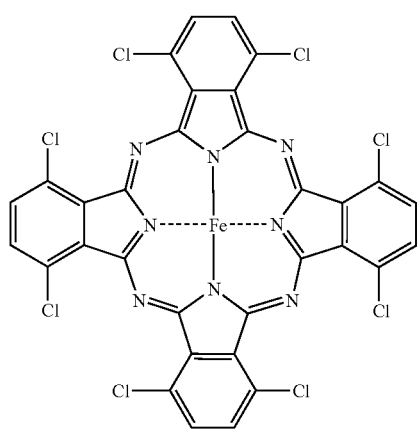
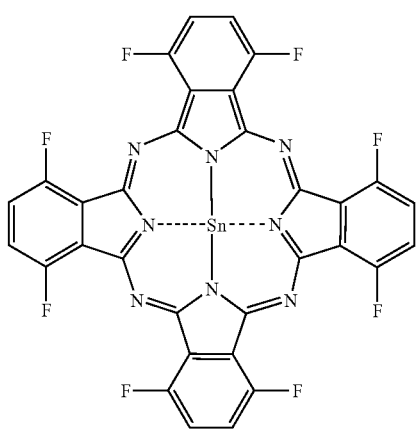
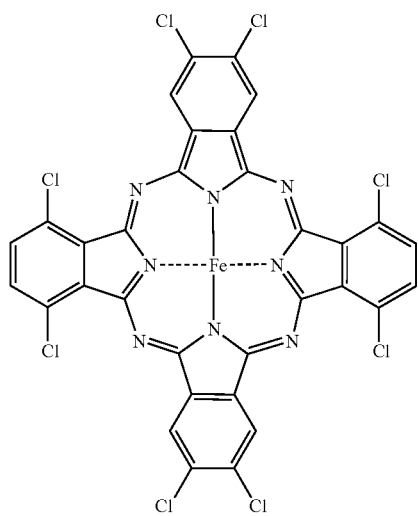
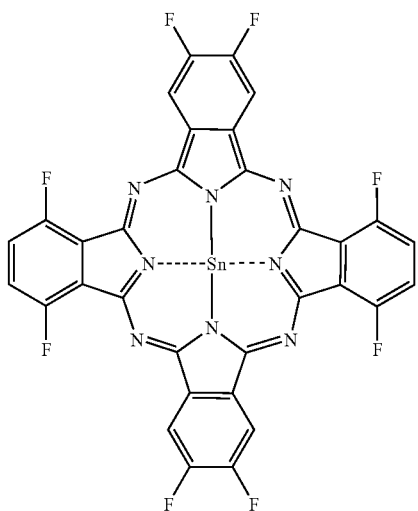
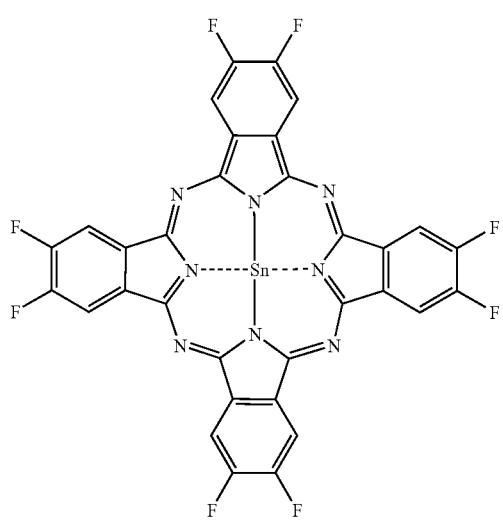
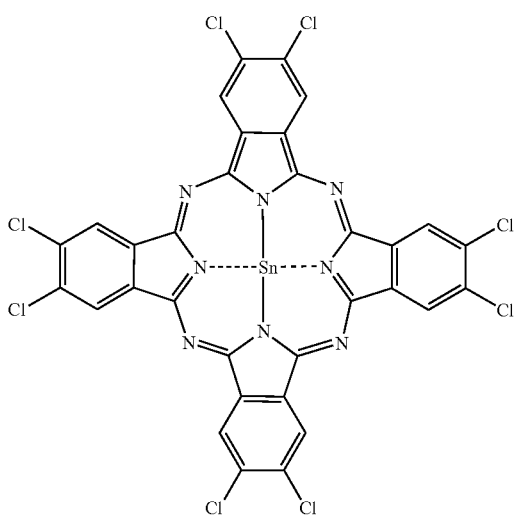

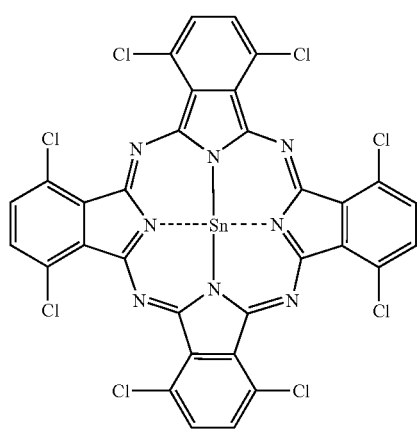
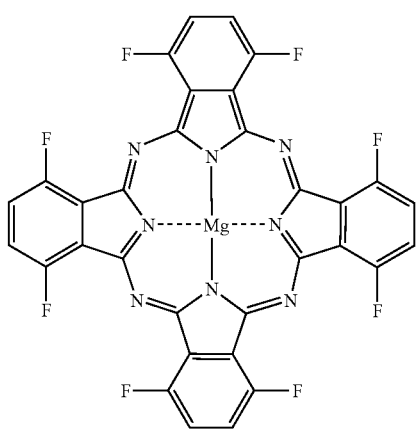
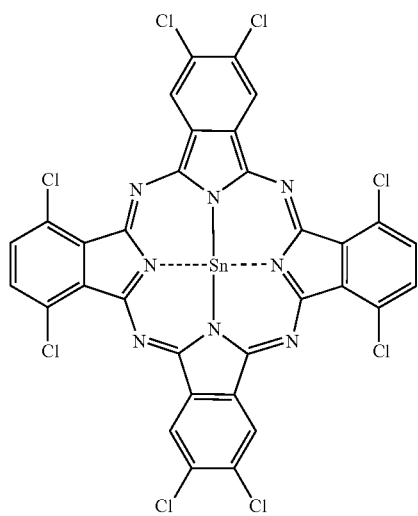
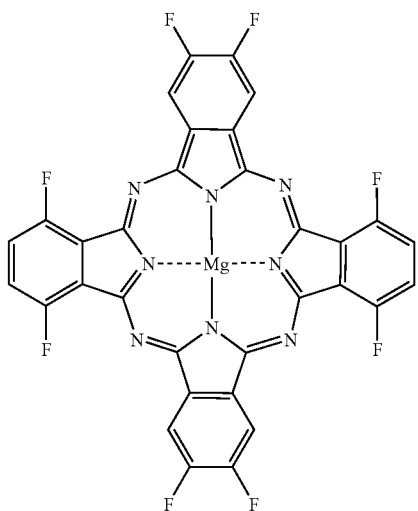
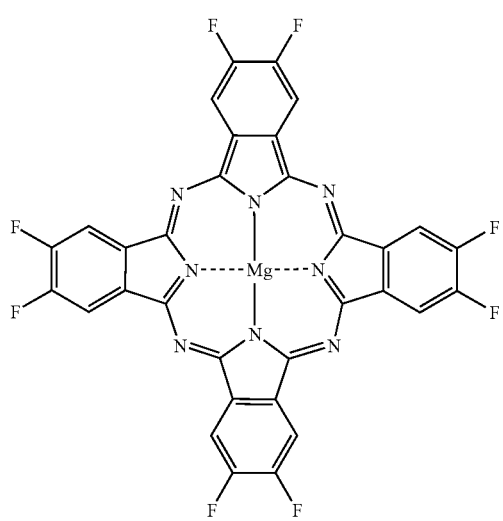
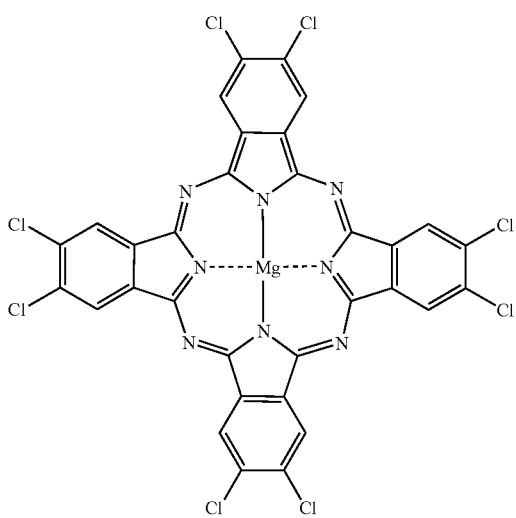

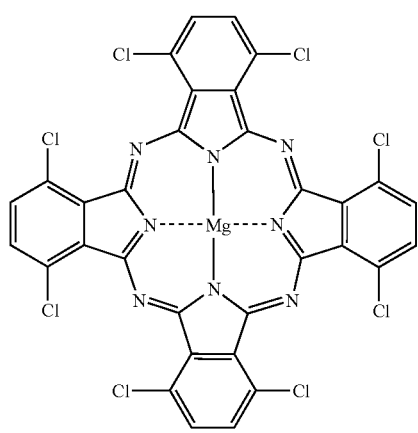
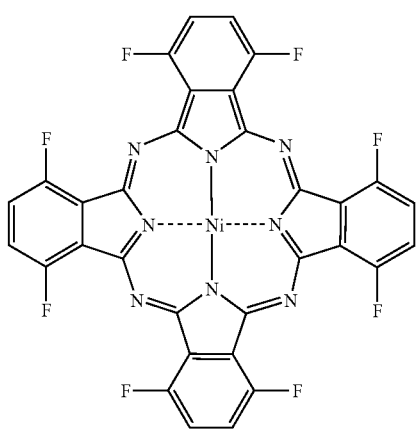
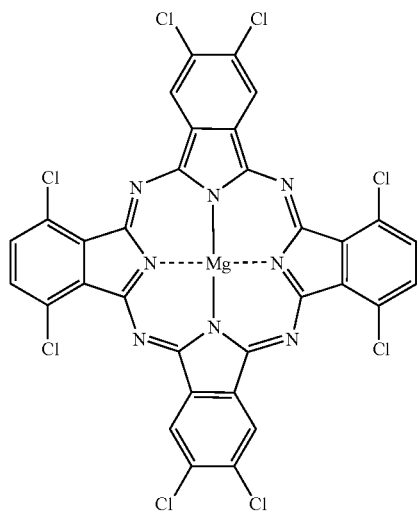
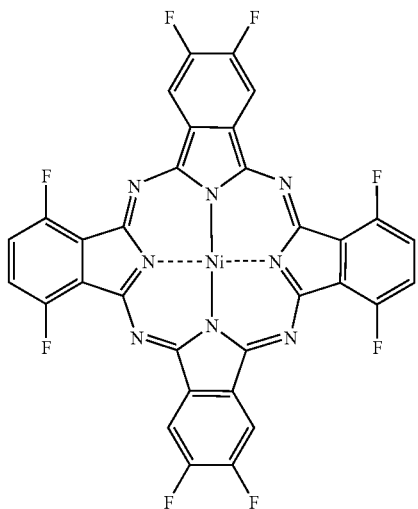
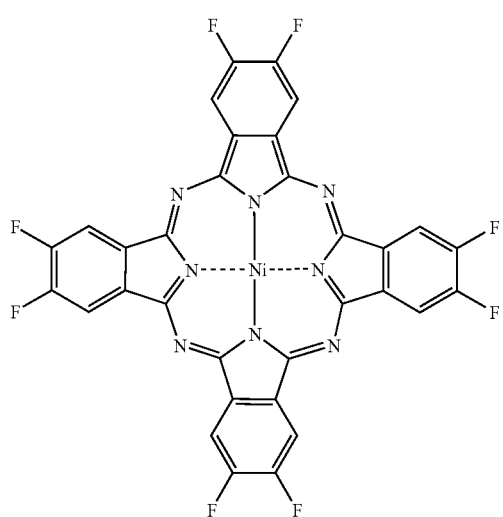
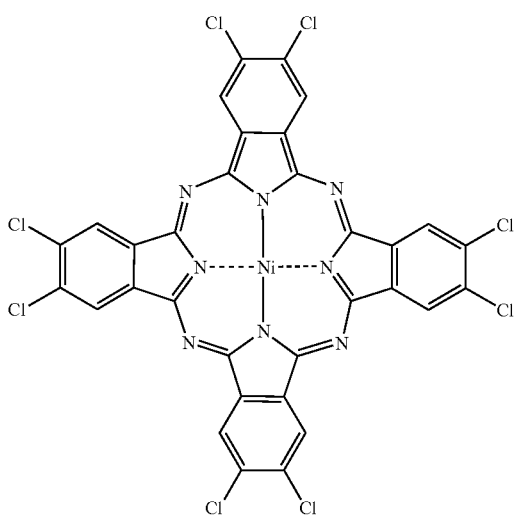

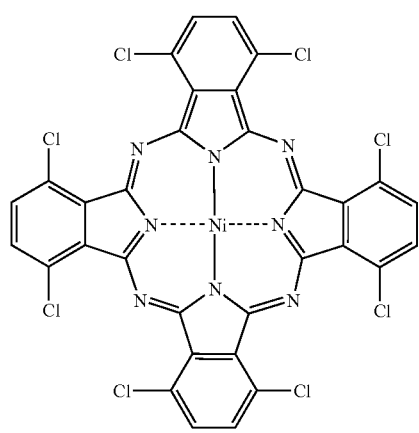
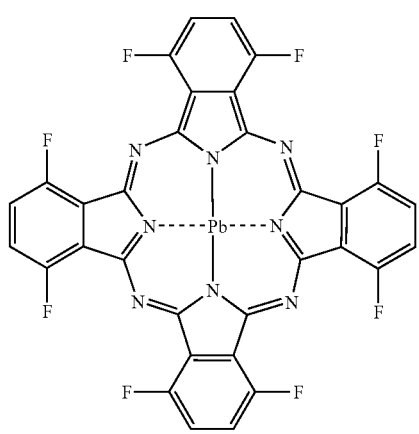
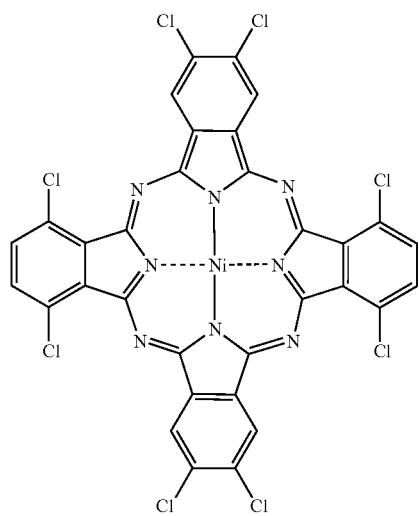
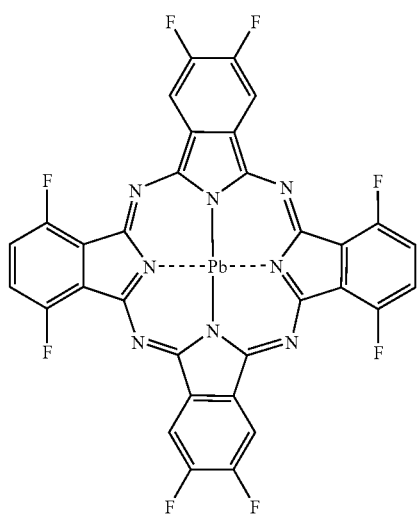
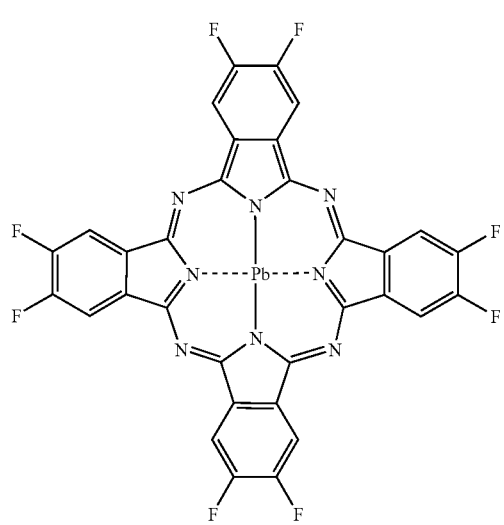
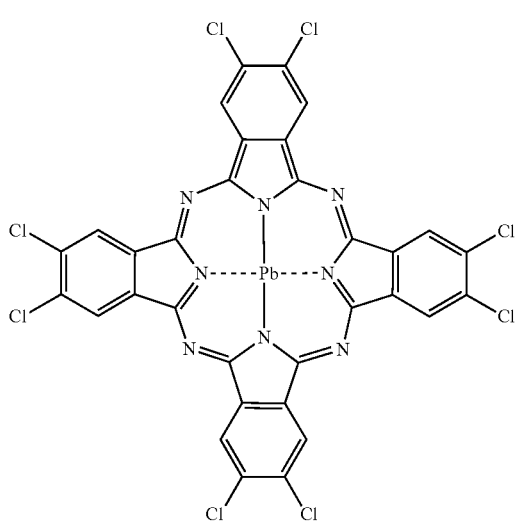

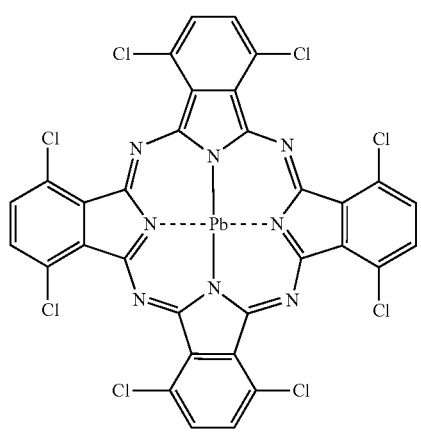
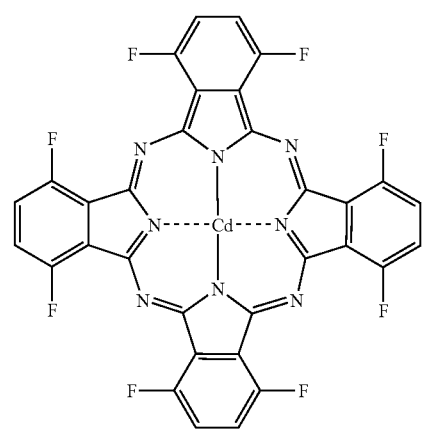
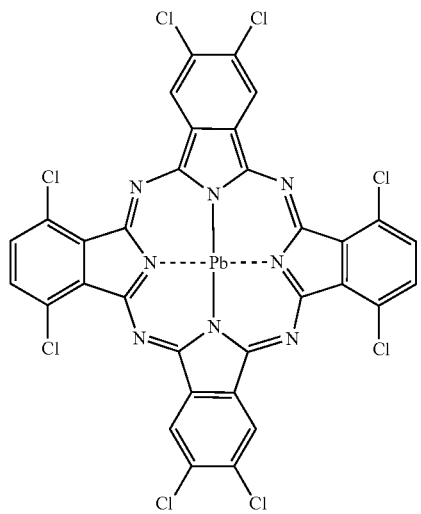
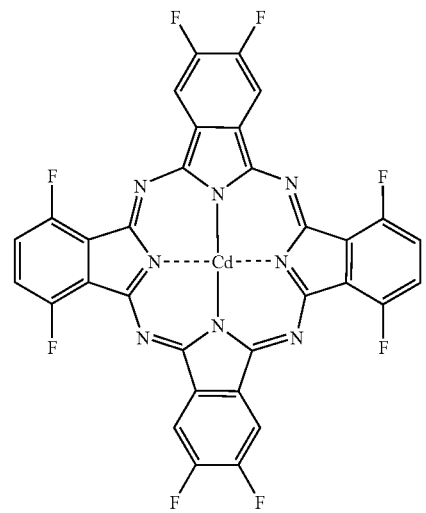
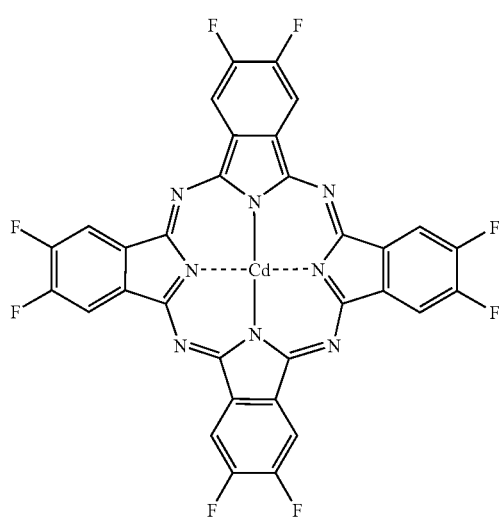
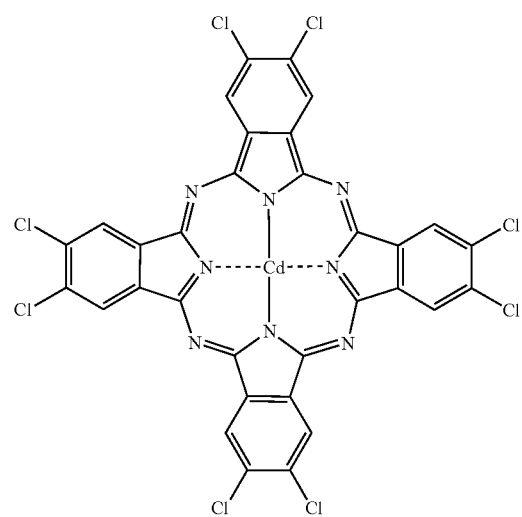

-continued
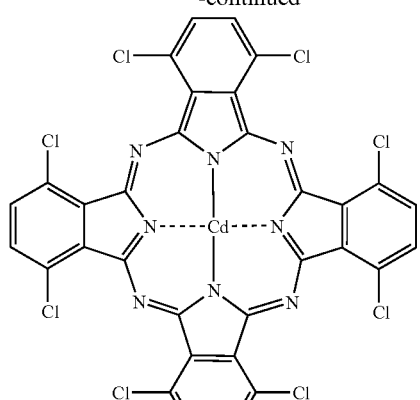
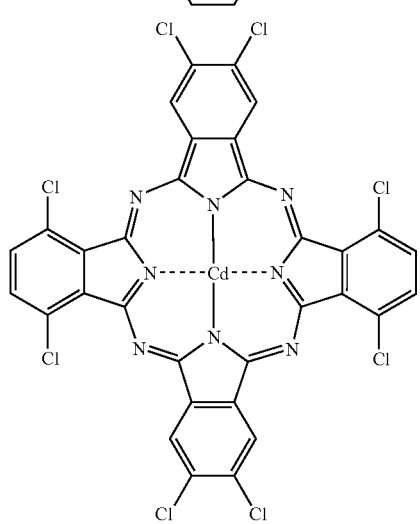
Examples of octafluorinated and octachlorinated phthalocyanines are also the following compounds of the formulae I.1, I.2, I.3, I.4, I.5 and I.6
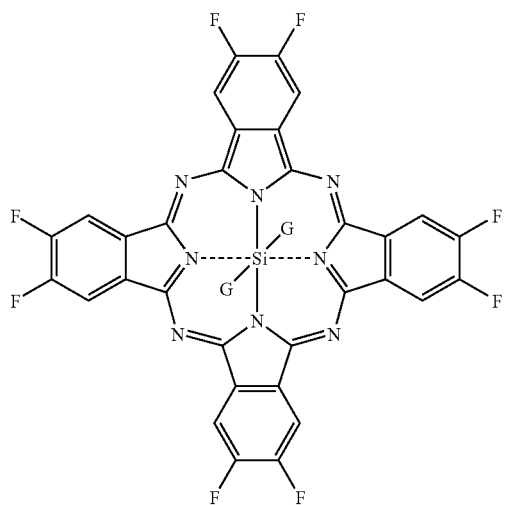
(I.1)
-continued
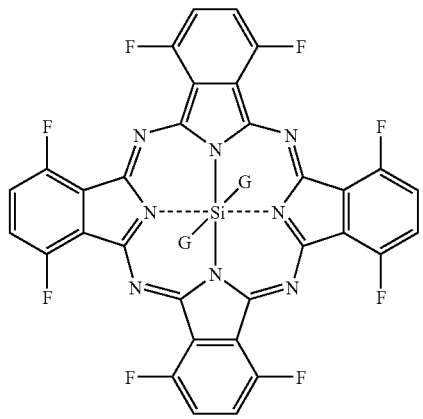
(I.2)
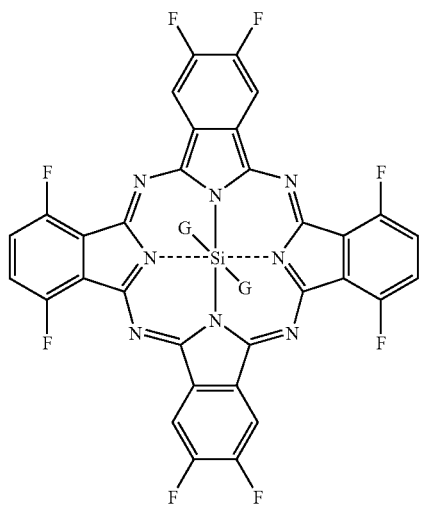
(I.3)
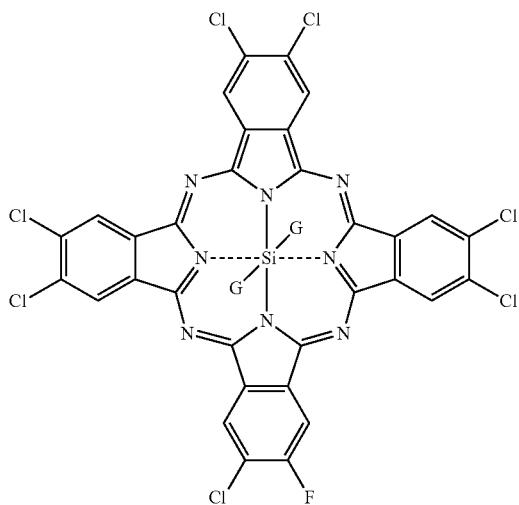
(I.4)

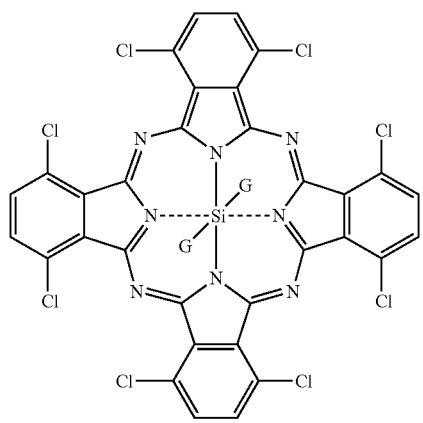
(I.5)
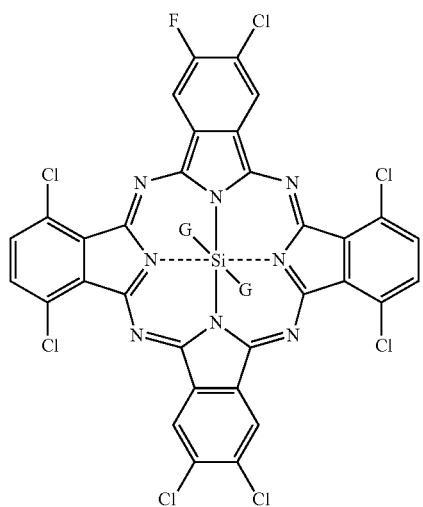
(I.6)
wherein G is H, F, Cl, OH, alkyl, alkoxy, aryl or aryloxy.
Examples of preferred octafluorinated and octachlorinated phthalocyanines are the following:
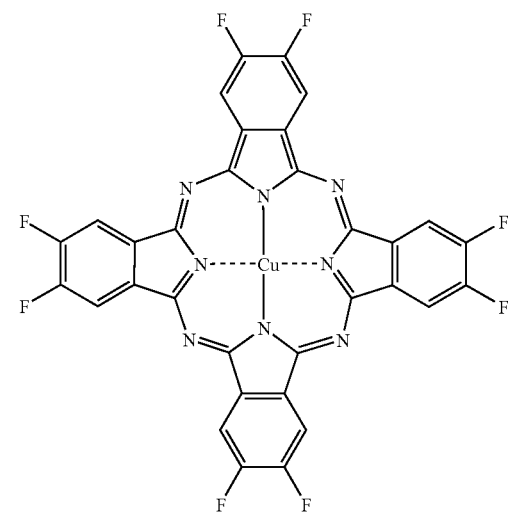
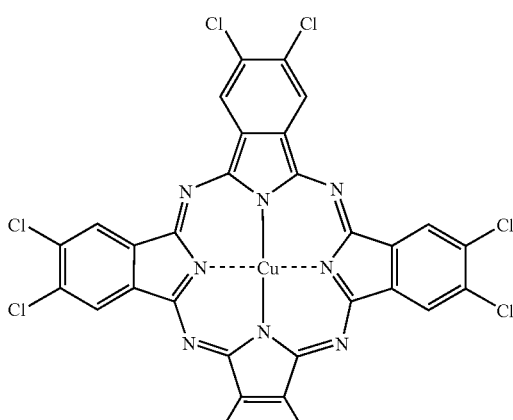
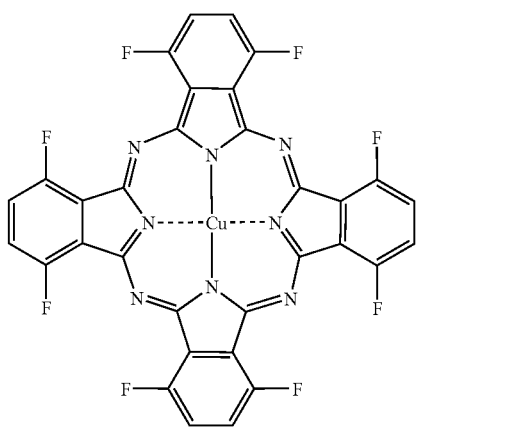
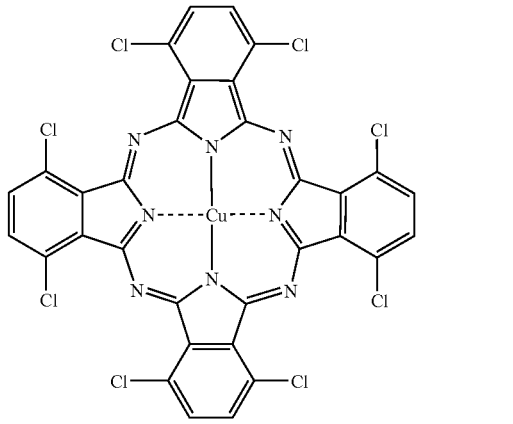

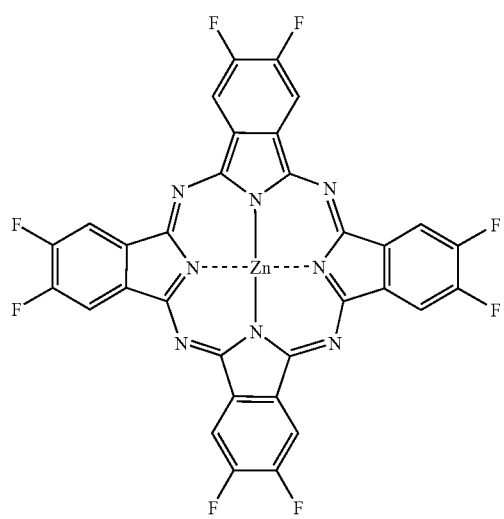
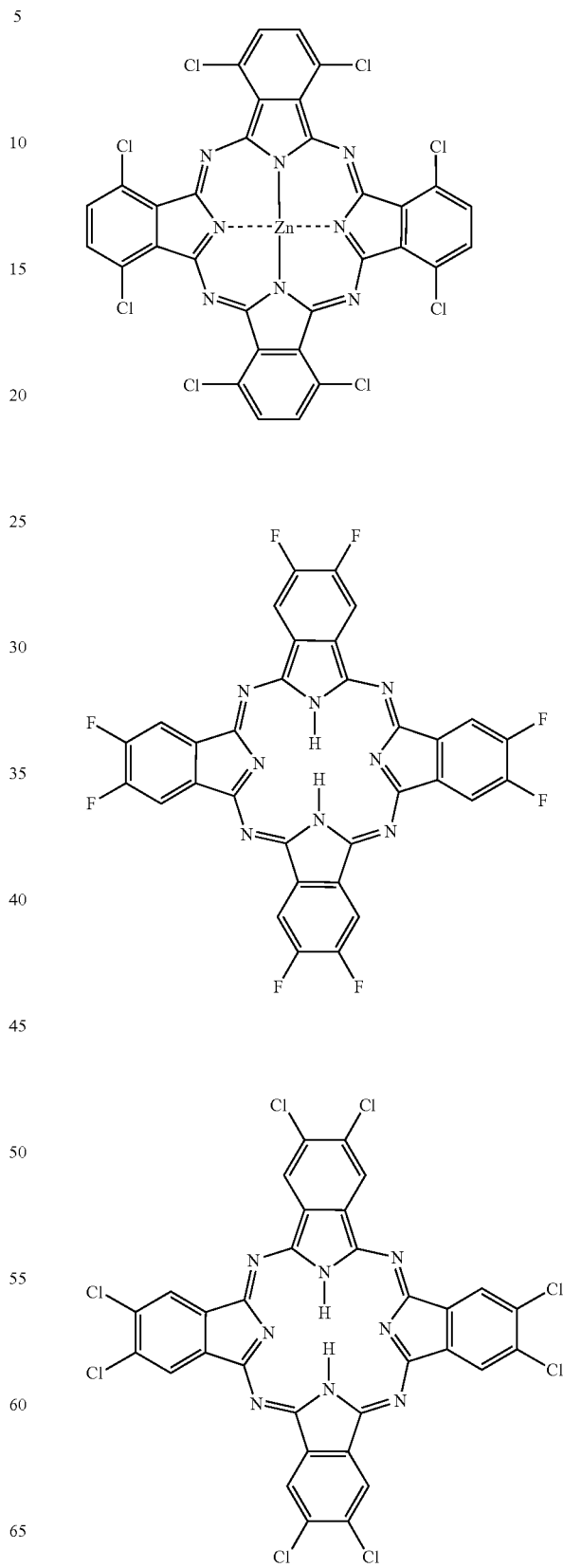

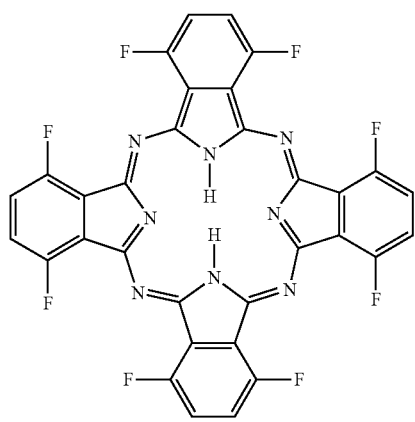
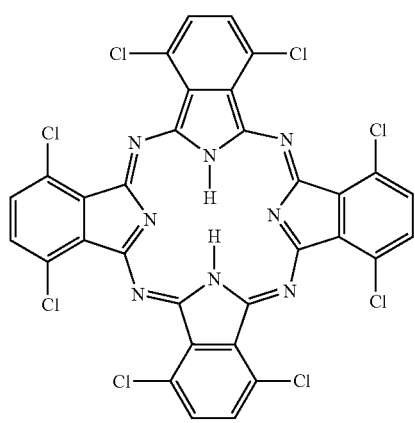
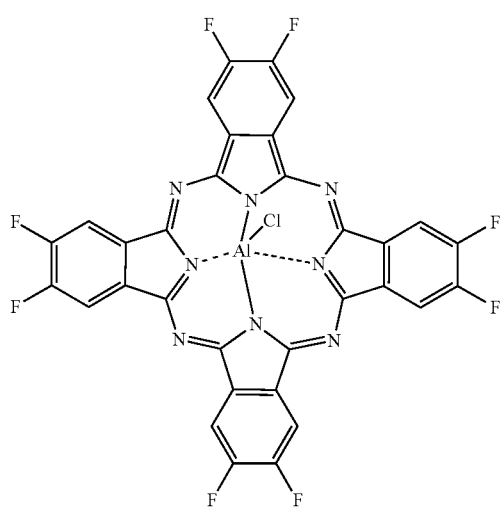
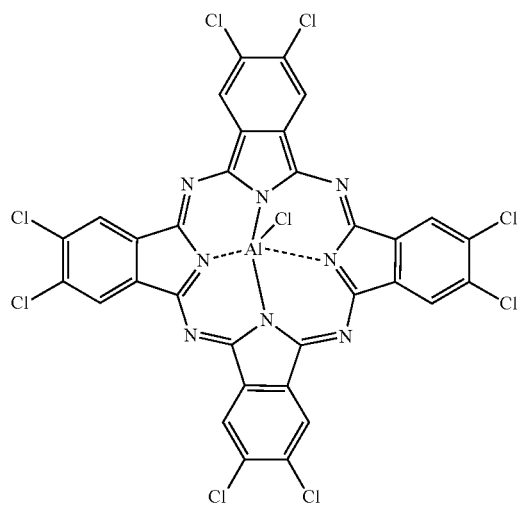
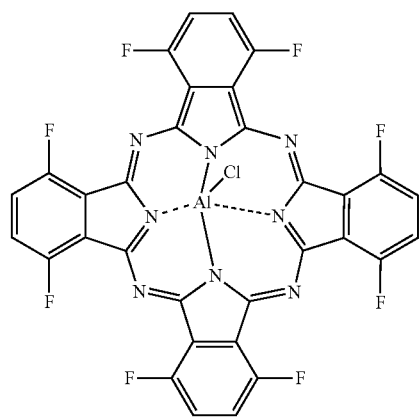
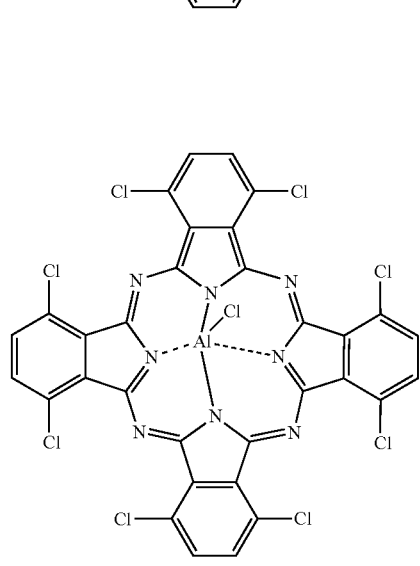

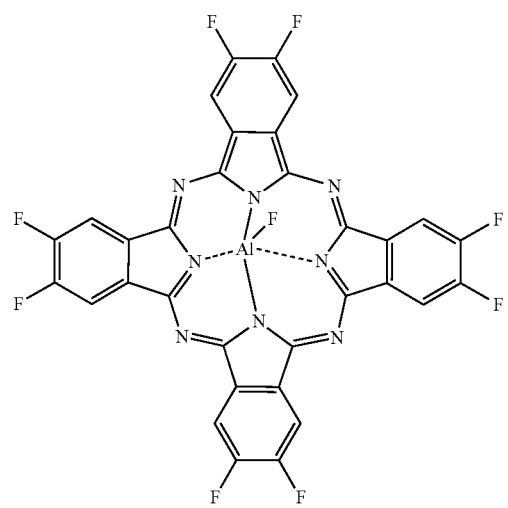
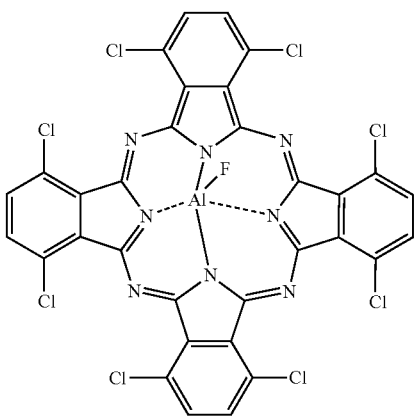
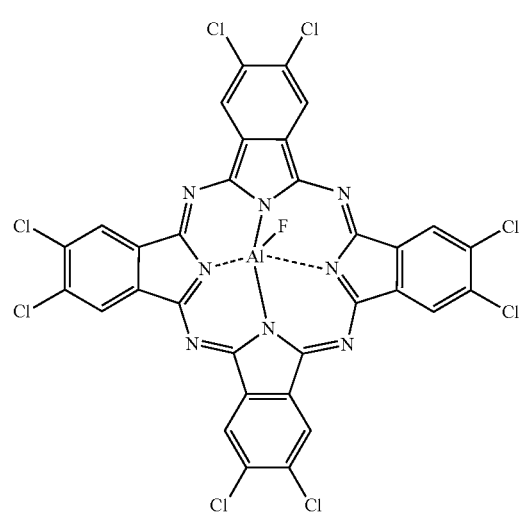
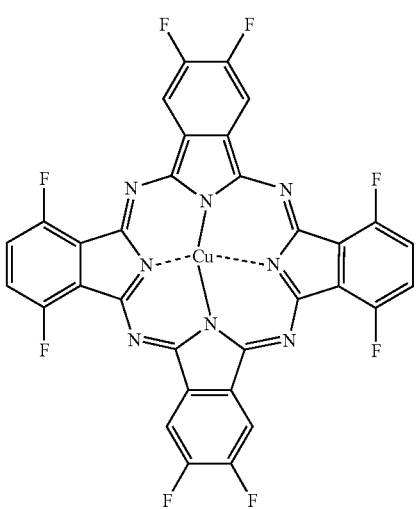
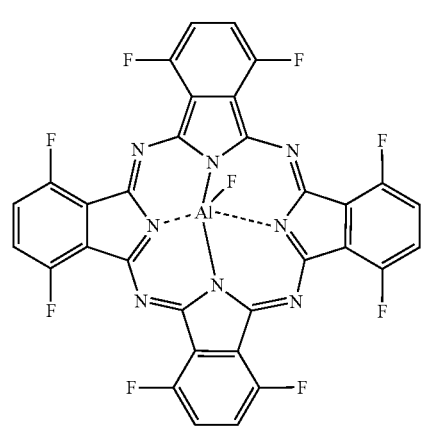
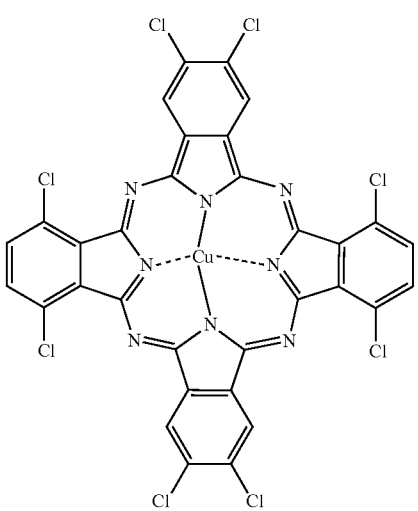 [SMILES: Clc1cc2c3nc4nc(nc5[nH]c(nc6nc(nc([nH]3)c2cc1Cl)-c1c(Cl)ccc(Cl)c1-6)c1cc(Cl)c(Cl)cc51)-c1c(Cl)ccc(Cl)c1-4]

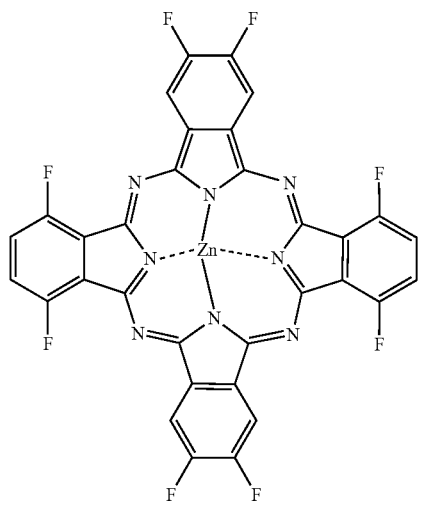
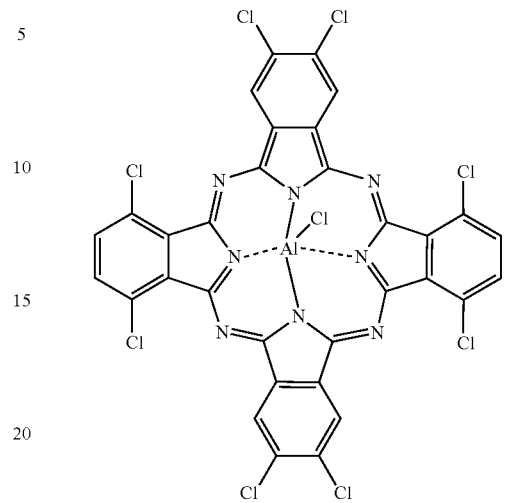
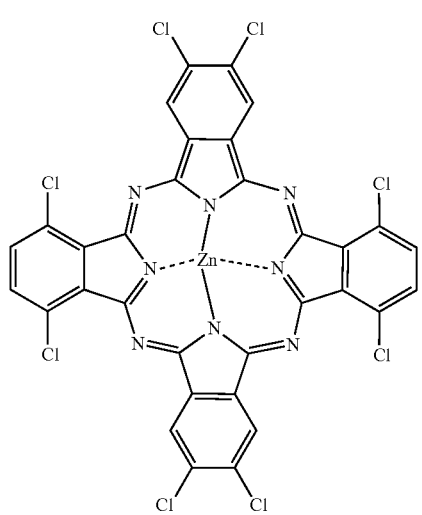
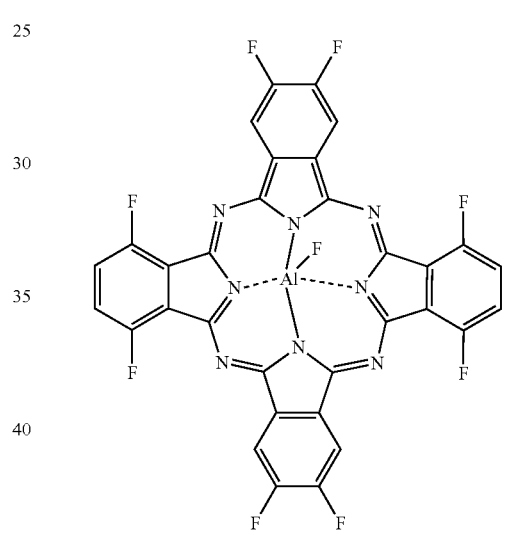
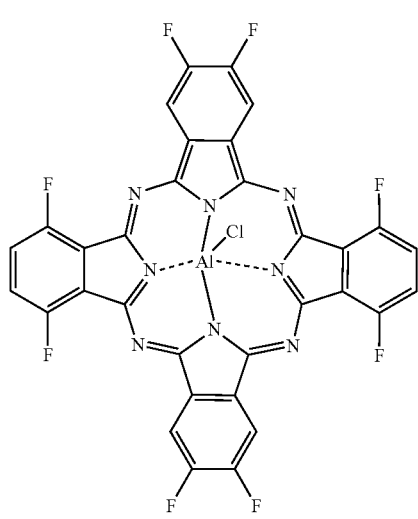
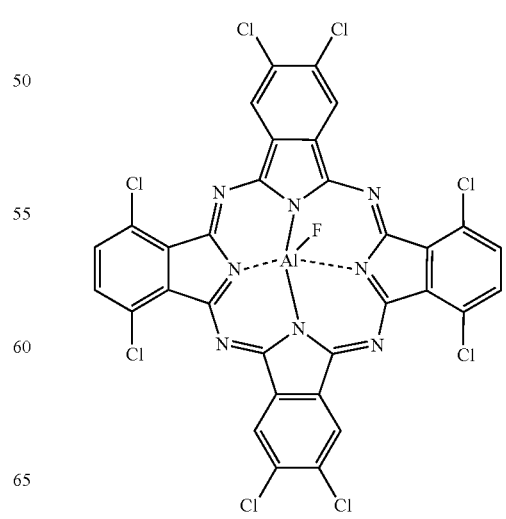

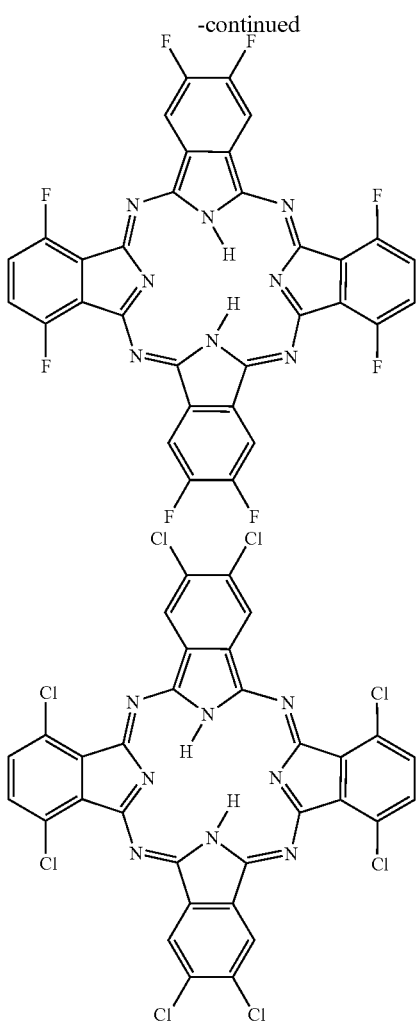

Examples of meta-tetrafluorinated phthalocyanines are the isomeric compounds of the following formula I.7 and mixtures thereof:

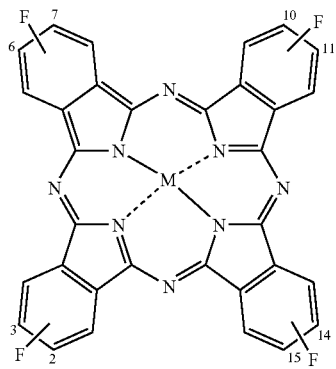

(I.7)

wherein M has one of the meanings given above and where each isomer has a first fluorine substituent in the 2 or 3 position, a second fluorine substituent in the 6 or 7 position, a third fluorine substituent in the 10 or 11 position and a fourth fluorine substituent in the 14 or 15 position.

Specific examples are compounds I.7 and mixtures thereof, wherein M is Ti(=O).

Specific examples are compounds I.7 and mixtures thereof, wherein M is Sn(=O).

Specific examples are compounds I.7 and mixtures thereof, wherein M is Al(OH).

Specific examples are compounds I.7 and mixtures thereof, wherein M is InCl.

Specific examples are compounds I.7 and mixtures thereof, wherein M is $SiH_2$.

Specific examples are compounds I.7 and mixtures thereof, wherein M is $SiF_2$.

Specific examples are compounds I.7 and mixtures thereof, wherein M is $SiCl_2$.

Specific examples are compounds I.7 and mixtures thereof, wherein M is $Si(OH)_2$.

Specific examples are compounds I.7 and mixtures thereof, wherein M is $Si(alkyl)_2$.

Specific examples are compounds I.7 and mixtures thereof, wherein M is $Si(alkoxy)_2$.

Specific examples are compounds I.7 and mixtures thereof, wherein M is $Si(aryl)_2$.

Specific examples are compounds I.7 and mixtures thereof, wherein M is $Si(aryloxy)_2$.

Specific examples are compounds I.7 and mixtures thereof, wherein M is Ag(II).

Specific examples are compounds I.7 and mixtures thereof, wherein M is Fe(II).

Specific examples are compounds I.7 and mixtures thereof, wherein M is Sn(II).

Specific examples are compounds I.7 and mixtures thereof, wherein M is Mg(II).

Specific examples are compounds I.7 and mixtures thereof, wherein M is Ni(II).

Specific examples are compounds I.7 and mixtures thereof, wherein M is Pb(II).

Specific examples are compounds I.7 and mixtures thereof, wherein M is Cd(II).

Examples of ortho-tetrafluorinated phthalocyanines are the isomeric compounds of the following formula I.8 and mixtures thereof:

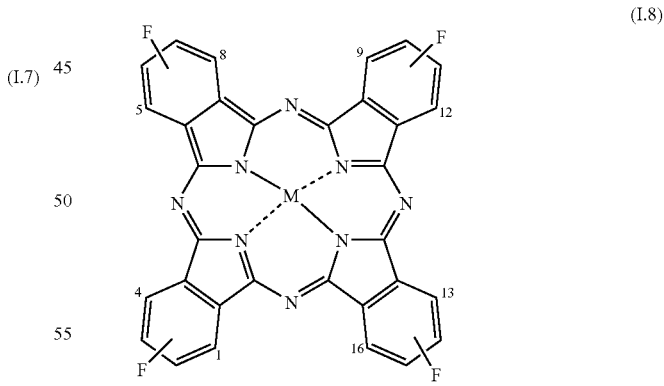

(I.8)

wherein M has one of the meanings given above and where each isomer has a first fluorine substituent in the 1 or 4 position, a second fluorine substituent in the 5 or 8 position, a third fluorine substituent in the 9 or 12 position and a fourth fluorine substituent in the 13 or 16 position.

Specific examples are compounds I.8 and mixtures thereof, wherein M is Ti(=O).

Specific examples are compounds I.8 and mixtures thereof, wherein M is Sn(=O).

Specific examples are compounds I.8 and mixtures thereof, wherein M is Al(OH).
Specific examples are compounds I.8 and mixtures thereof, wherein M is InCl.
Specific examples are compounds I.8 and mixtures thereof, wherein M is $SiH_2$.
Specific examples are compounds I.8 and mixtures thereof, wherein M is $SiF_2$.
Specific examples are compounds I.8 and mixtures thereof, wherein M is $SiCl_2$.
Specific examples are compounds I.8 and mixtures thereof, wherein M is $Si(OH)_2$.
Specific examples are compounds I.8 and mixtures thereof, wherein M is $Si(alkyl)_2$.
Specific examples are compounds I.8 and mixtures thereof, wherein M is $Si(alkoxy)_2$.
Specific examples are compounds I.8 and mixtures thereof, wherein M is $Si(aryl)_2$.
Specific examples are compounds I.8 and mixtures thereof, wherein M is $Si(aryloxy)_2$.
Specific examples are compounds I.8 and mixtures thereof, wherein M is Ag(II).
Specific examples are compounds I.8 and mixtures thereof, wherein M is Fe(II).
Specific examples are compounds I.8 and mixtures thereof, wherein M is Sn(II).
Specific examples are compounds I.8 and mixtures thereof, wherein M is Mg(II).
Specific examples are compounds I.8 and mixtures thereof, wherein M is Ni(II).
Specific examples are compounds I.8 and mixtures thereof, wherein M is Pb(II).
Specific examples are compounds I.8 and mixtures thereof, wherein M is Cd(II).

Examples of meta-tetrachlorinated phthalocyanines are the isomeric compounds of the following formula I.9 and mixtures thereof:

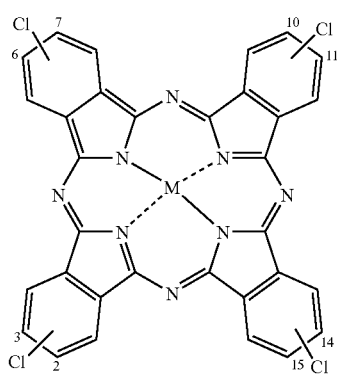

(I.9)

wherein M has one of the meanings given above and where each isomer has a first chlorine substituent in the 2 or 3 position, a second chlorine substituent in the 6 or 7 position, a third chlorine substituent in the 10 or 11 position and a fourth chlorine substituent in the 14 or 15 position.

Specific examples are compounds I.9 and mixtures thereof, wherein M is Ti(=O).
Specific examples are compounds I.9 and mixtures thereof, wherein M is Sn(=O).
Specific examples are compounds I.9 and mixtures thereof, wherein M is Al(OH).
Specific examples are compounds I.9 and mixtures thereof, wherein M is InCl.
Specific examples are compounds I.9 and mixtures thereof, wherein M is $SiH_2$.
Specific examples are compounds I.9 and mixtures thereof, wherein M is $SiF_2$.
Specific examples are compounds I.9 and mixtures thereof, wherein M is $SiCl_2$.
Specific examples are compounds I.9 and mixtures thereof, wherein M is $Si(OH)_2$.
Specific examples are compounds I.9 and mixtures thereof, wherein M is $Si(alkyl)_2$.
Specific examples are compounds I.9 and mixtures thereof, wherein M is $Si(alkoxy)_2$.
Specific examples are compounds I.9 and mixtures thereof, wherein M is $Si(aryl)_2$.
Specific examples are compounds I.9 and mixtures thereof, wherein M is $Si(aryloxy)_2$.
Specific examples are compounds I.9 and mixtures thereof, wherein M is Ag(II).
Specific examples are compounds I.9 and mixtures thereof, wherein M is Fe(II).
Specific examples are compounds I.9 and mixtures thereof, wherein M is Sn(II).
Specific examples are compounds I.9 and mixtures thereof, wherein M is Mg(II).
Specific examples are compounds I.9 and mixtures thereof, wherein M is Ni(II).
Specific examples are compounds I.9 and mixtures thereof, wherein M is Pb(II).
Specific examples are compounds I.9 and mixtures thereof, wherein M is Cd(II).

Examples of ortho-tetrachlorinated phthalocyanines are the isomeric compounds of the following formula I.10 and mixtures thereof:

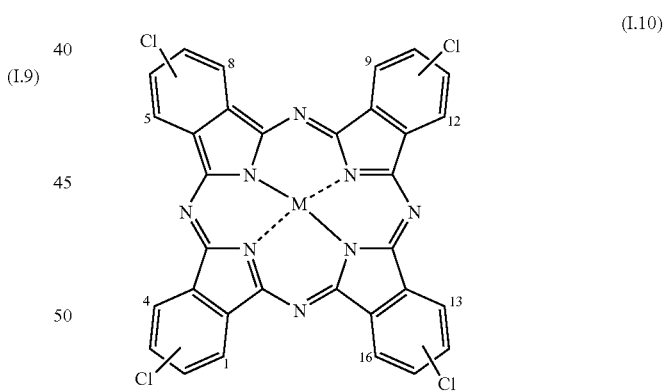

(I.10)

wherein M has one of the meanings given above and where each isomer has a first chlorine substituent in the 1 or 4 position, a second chlorine substituent in the 5 or 8 position, a third chlorine substituent in the 9 or 12 position and a fourth chlorine substituent in the 13 or 16 position.

Specific examples are compounds I.10 and mixtures thereof, wherein M is Ti(=O).
Specific examples are compounds I.10 and mixtures thereof, wherein M is Sn(=O).
Specific examples are compounds I.10 and mixtures thereof, wherein M is Al(OH).
Specific examples are compounds I.10 and mixtures thereof, wherein M is InCl.

Specific examples are compounds I.10 and mixtures thereof, wherein M is SiH$_2$.
Specific examples are compounds I.10 and mixtures thereof, wherein M is SiF$_2$.
Specific examples are compounds I.10 and mixtures thereof, wherein M is SiCl$_2$.
Specific examples are compounds I.10 and mixtures thereof, wherein M is Si(OH)$_2$.
Specific examples are compounds I.10 and mixtures thereof, wherein M is Si(alkyl)$_2$.
Specific examples are compounds I.10 and mixtures thereof, wherein M is Si(alkoxy)$_2$.
Specific examples are compounds I.10 and mixtures thereof, wherein M is Si(aryl)$_2$.
Specific examples are compounds I.10 and mixtures thereof, wherein M is Si(aryloxy)$_2$.
Specific examples are compounds I.10 and mixtures thereof, wherein M is Ag(II).
Specific examples are compounds I.10 and mixtures thereof, wherein M is Fe(II).
Specific examples are compounds I.10 and mixtures thereof, wherein M is Sn(II).
Specific examples are compounds I.10 and mixtures thereof, wherein M is Mg(II).
Specific examples are compounds I.10 and mixtures thereof, wherein M is Ni(II).
Specific examples are compounds I.10 and mixtures thereof, wherein M is Pb(II).
Specific examples are compounds I.10 and mixtures thereof, wherein M is Cd(II).

Examples of tetrafluorinated phthalocyanines are also the isomeric compounds of the following formulae I.11 and mixtures thereof:

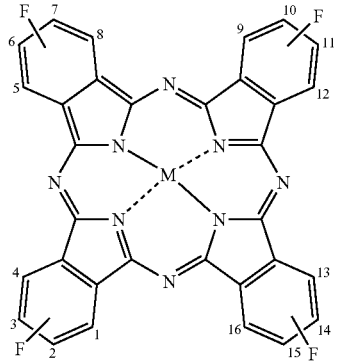

(I.11)

where M has one of the meanings given above and where each of the isomers I.11 has a first fluorine substituent in the 1 or 2 or 3 or 4 position, a second fluorine substituent in the 5 or 6 or 7 or 8 position, a third fluorine substituent in the 9 or 10 or 11 or 12 position and a fourth fluorine substituent in the 13 or 14 or 15 or 16 position.
Specific examples are compounds I.11 and mixtures thereof, wherein M is Ti(=O).
Specific examples are compounds I.11 and mixtures thereof, wherein M is Sn(=O).
Specific examples are compounds I.11 and mixtures thereof, wherein M is Al(OH).
Specific examples are compounds I.11 and mixtures thereof, wherein M is InCl.
Specific examples are compounds I.11 and mixtures thereof, wherein M is SiH$_2$.
Specific examples are compounds I.11 and mixtures thereof, wherein M is SiF$_2$.
Specific examples are compounds I.11 and mixtures thereof, wherein M is SiCl$_2$.
Specific examples are compounds I.11 and mixtures thereof, wherein M is Si(OH)$_2$.
Specific examples are compounds I.11 and mixtures thereof, wherein M is Si(alkyl)$_2$.
Specific examples are compounds I.11 and mixtures thereof, wherein M is Si(alkoxy)$_2$.
Specific examples are compounds I.11 and mixtures thereof, wherein M is Si(aryl)$_2$.
Specific examples are compounds I.11 and mixtures thereof, wherein M is Si(aryloxy)$_2$.
Specific examples are compounds I.11 and mixtures thereof, wherein M is Ag(II).
Specific examples are compounds I.11 and mixtures thereof, wherein M is Fe(II).
Specific examples are compounds I.11 and mixtures thereof, wherein M is Sn(II).
Specific examples are compounds I.11 and mixtures thereof, wherein M is Mg(II).
Specific examples are compounds I.11 and mixtures thereof, wherein M is Ni(II).
Specific examples are compounds I.11 and mixtures thereof, wherein M is Pb(II).
Specific examples are compounds I.11 and mixtures thereof, wherein M is Cd(II).

Examples of tetrachlorinated phthalocyanines are also the isomeric compounds of the following formulae I.12 and mixtures thereof:

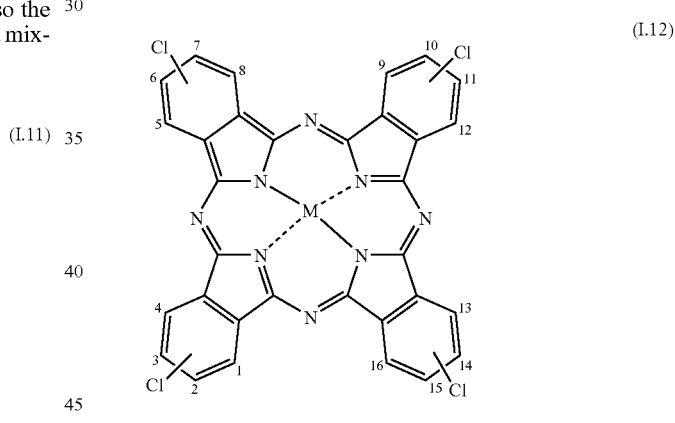

where M has one of the meanings given above and in which each of the isomers I.12 has a first chlorine substituent in the 1 or 2 or 3 or 4 position, a second chlorine substituent in the 5 or 6 or 7 or 8 position, a third chlorine substituent in the 9 or 10 or 11 or 12 position and a fourth chlorine substituent in the 13 or 14 or 15 or 16 position
Specific examples are compounds I.12 and mixtures thereof, wherein M is Ti(=O).
Specific examples are compounds I.12 and mixtures thereof, wherein M is Sn(=O).
Specific examples are compounds I.12 and mixtures thereof, wherein M is Al(OH).
Specific examples are compounds I.12 and mixtures thereof, wherein M is InCl.
Specific examples are compounds I.12 and mixtures thereof, wherein M is SiH$_2$.
Specific examples are compounds I.12 and mixtures thereof, wherein M is SiF$_2$.
Specific examples are compounds I.12 and mixtures thereof, wherein M is SiCl$_2$.
Specific examples are compounds I.12 and mixtures thereof, wherein M is Si(OH)$_2$.

Specific examples are compounds I.12 and mixtures thereof, wherein M is Si(alkyl)$_2$.
Specific examples are compounds I.12 and mixtures thereof, wherein M is Si(alkoxy)$_2$.
Specific examples are compounds I.12 and mixtures thereof, wherein M is Si(aryl)$_2$.
Specific examples are compounds I.12 and mixtures thereof, wherein M is Si(aryloxy)$_2$.
Specific examples are compounds I.12 and mixtures thereof, wherein M is Ag(II).
Specific examples are compounds I.12 and mixtures thereof, wherein M is Fe(II).
Specific examples are compounds I.12 and mixtures thereof, wherein M is Sn(II).
Specific examples are compounds I.12 and mixtures thereof, wherein M is Mg(II).
Specific examples are compounds I.12 and mixtures thereof, wherein M is Ni(II).
Specific examples are compounds I.12 and mixtures thereof, wherein M is Pb(II).
Specific examples are compounds I.12 and mixtures thereof, wherein M is Cd(II).

Preferred meta-tetrafluorinated phthalocyanines are the isomeric compounds of the following formula IA and mixtures thereof:

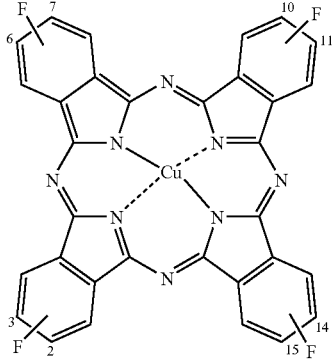

(IA)

where each isomer has a first fluorine substituent in the 2 or 3 position, a second fluorine substituent in the 6 or 7 position, a third fluorine substituent in the 10 or 11 position and a fourth fluorine substituent in the 14 or 15 position.

Preferred meta-tetrafluorinated phthalocyanines are also the isomeric compounds of the following formula IB and mixtures thereof:

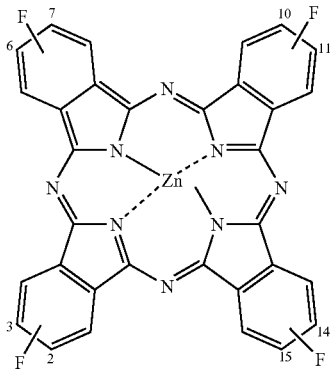

(IB)

where each isomer has a first fluorine substituent in the 2 or 3 position, a second fluorine substituent in the 6 or 7 position, a third fluorine substituent in the 10 or 11 position and a fourth fluorine substituent in the 14 or 15 position.

Preferred meta-tetrafluorinated phthalocyanines are also the isomeric compounds of the following formula IC and mixtures thereof:

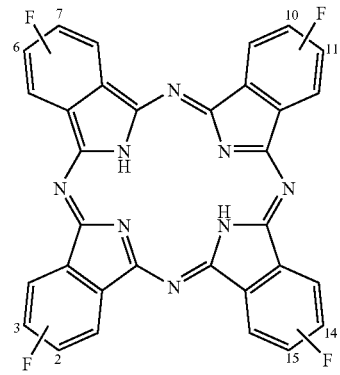

(IC)

where each isomer has a first fluorine substituent in the 2 or 3 position, a second fluorine substituent in the 6 or 7 position, a third fluorine substituent in the 10 or 11 position and a fourth fluorine substituent in the 14 or 15 position.

Preferred meta-tetrafluorinated phthalocyanines are also the isomeric compounds of the following formula ID and mixtures thereof:

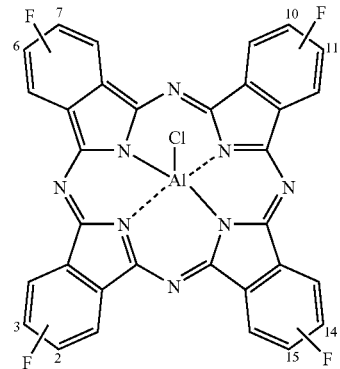

(ID)

where each isomer has a first fluorine substituent in the 2 or 3 position, a second fluorine substituent in the 6 or 7 position, a third fluorine substituent in the 10 or 11 position and a fourth fluorine substituent in the 14 or 15 position.

Preferred meta-tetrafluorinated phthalocyanines are also the isomeric compounds of the following formula IE and mixtures thereof:

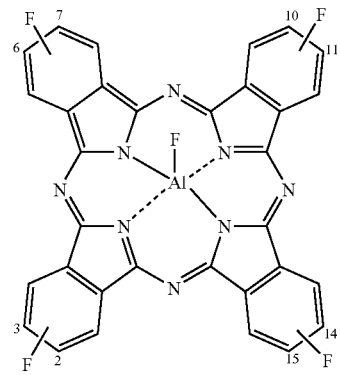

(IE)

where each isomer has a first fluorine substituent in the 2 or 3 position, a second fluorine substituent in the 6 or 7 position, a third fluorine substituent in the 10 or 11 position and a fourth fluorine substituent in the 14 or 15 position.

Preferred ortho-tetrafluorinated phthalocyanines are also the isomeric compounds of the following formula IF and mixtures thereof:

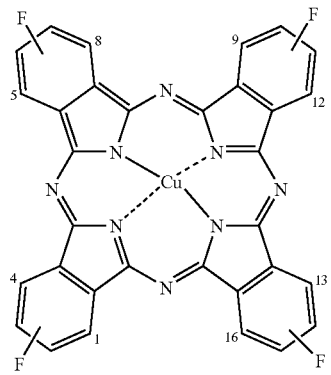

(IF)

where each isomer has a first fluorine substituent in the 1 or 4 position, a second fluorine substituent in the 5 or 8 position, a third fluorine substituent in the 9 or 12 position and a fourth fluorine substituent in the 13 or 16 position.

Preferred ortho-tetrafluorinated phthalocyanines are also the isomeric compounds of the following formula IG and mixtures thereof:

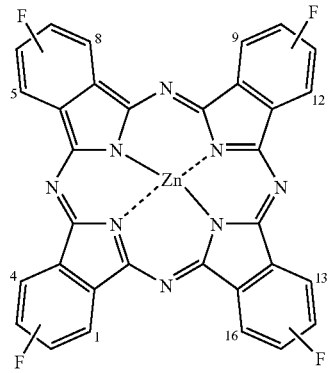

(IG)

where each isomer has a first fluorine substituent in the 1 or 4 position, a second fluorine substituent in the 5 or 8 position, a third fluorine substituent in the 9 or 12 position and a fourth fluorine substituent in the 13 or 16 position.

Preferred ortho-tetrafluorinated phthalocyanines are also the isomeric compounds of the following formula IH and mixtures thereof:

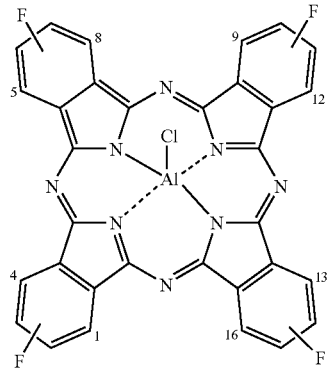

(IH)

where each isomer has a first fluorine substituent in the 1 or 4 position, a second fluorine substituent in the 5 or 8 position, a third fluorine substituent in the 9 or 12 position and a fourth fluorine substituent in the 13 or 16 position.

Preferred ortho-tetrafluorinated phthalocyanines are also the isomeric compounds of the following formula II and mixtures thereof:

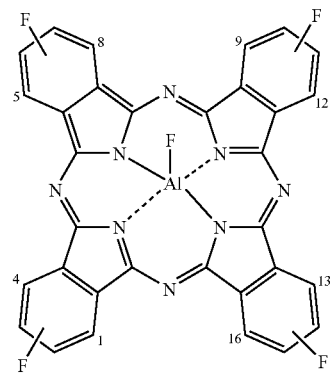

(II)

where each isomer has a first fluorine substituent in the 1 or 4 position, a second fluorine substituent in the 5 or 8 position, a third fluorine substituent in the 9 or 12 position and a fourth fluorine substituent in the 13 or 16 position.

Preferred ortho-tetrafluorinated phthalocyanines are also the isomeric compounds of the following formula IJ and mixtures thereof:

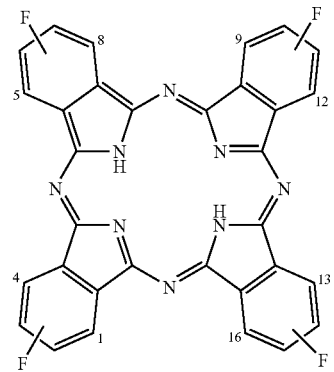

(IJ)

where each isomer has a first fluorine substituent in the 1 or 4 position, a second fluorine substituent in the 5 or 8 position, a third fluorine substituent in the 9 or 12 position and a fourth fluorine substituent in the 13 or 16 position.

Preferred meta-tetrachlorinated phthalocyanines are the isomeric compounds of the following formula IK and mixtures thereof:

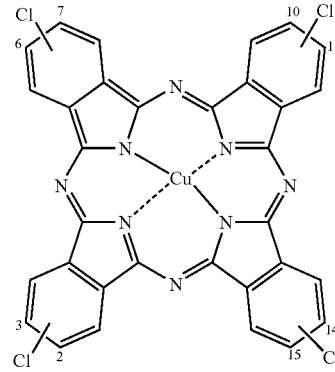

(IK)

where each isomer has a first chlorine substituent in the 2 or 3 position, a second chlorine substituent in the 6 or 7 position, a third chlorine substituent in the 10 or 11 position and a fourth chlorine substituent in the 14 or 15 position.

Preferred meta-tetrachlorinated phthalocyanines are also the isomeric compounds of the following formula IL and mixtures thereof:

(IL)

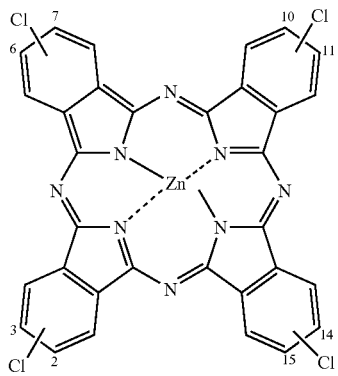

where each isomer has a first chlorine substituent in the 2 or 3 position, a second chlorine substituent in the 6 or 7 position, a third chlorine substituent in the 10 or 11 position and a fourth chlorine substituent in the 14 or 15 position.

Preferred meta-tetrachlorinated phthalocyanines are also the isomeric compounds of the following formula IM and mixtures thereof:

(IM)

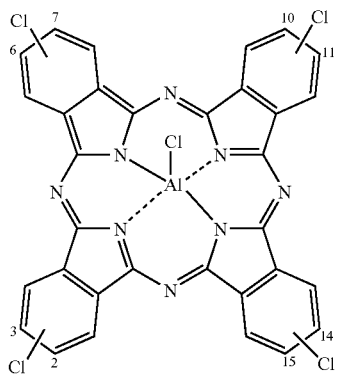

where each isomer has a first chlorine substituent in the 2 or 3 position, a second chlorine substituent in the 6 or 7 position, a third chlorine substituent in the 10 or 11 position and a fourth chlorine substituent in the 14 or 15 position.

Preferred meta-tetrachlorinated phthalocyanines are also the isomeric compounds of the following formula IN and mixtures thereof:

(IN)

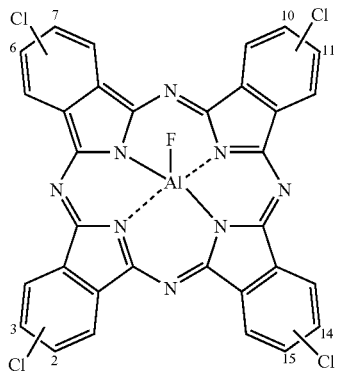

where each isomer has a first chlorine substituent in the 2 or 3 position, a second chlorine substituent in the 6 or 7 position, a third chlorine substituent in the 10 or 11 position and a fourth chlorine substituent in the 14 or 15 position.

Preferred meta-tetrachlorinated phthalocyanines are also the isomeric compounds of the following formula IO and mixtures thereof:

(IO)

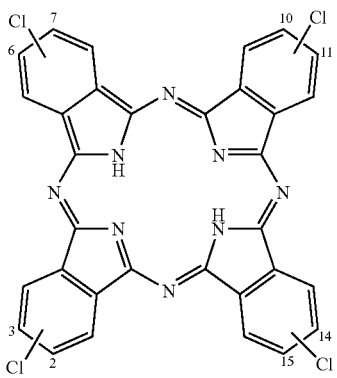

where each isomer has a first chlorine substituent in the 2 or 3 position, a second chlorine substituent in the 6 or 7 position, a third chlorine substituent in the 10 or 11 position and a fourth chlorine substituent in the 14 or 15 position.

Preferred ortho-tetrachlorinated phthalocyanines are also the isomeric compounds of the following formula IP and mixtures thereof:

(IP)

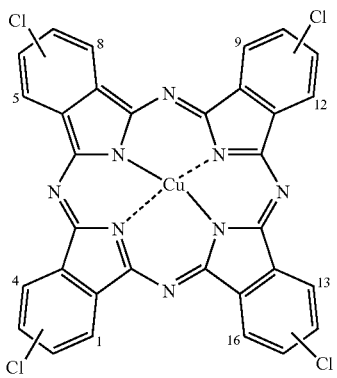

where each isomer has a first chlorine substituent in the 1 or 4 position, a second chlorine substituent in the 5 or 8 position, a third chlorine substituent in the 9 or 12 position and a fourth chlorine substituent in the 13 or 16 position.

Preferred ortho-tetrachlorinated phthalocyanines are also the isomeric compounds of the following formula IQ and mixtures thereof:

(IQ)

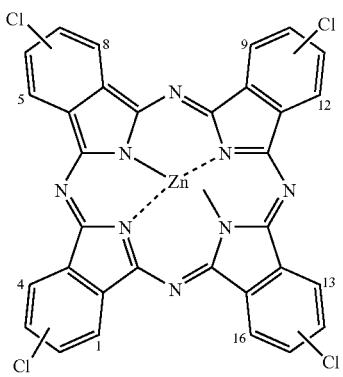

where each isomer has a first chlorine substituent in the 1 or 4 position, a second chlorine substituent in the 5 or 8 position, a third chlorine substituent in the 9 or 12 position and a fourth chlorine substituent in the 13 or 16 position.

Preferred ortho-tetrachlorinated phthalocyanines are also the isomeric compounds of the following formula IR and mixtures thereof:

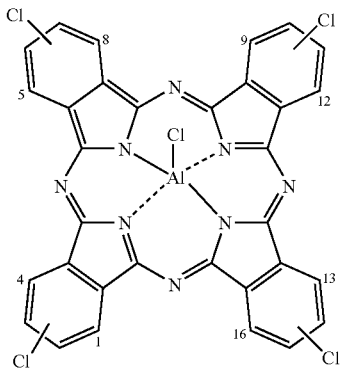
(IR)

where each isomer has a first chlorine substituent in the 1 or 4 position, a second chlorine substituent in the 5 or 8 position, a third chlorine substituent in the 9 or 12 position and a fourth chlorine substituent in the 13 or 16 position.

Preferred ortho-tetrachlorinated phthalocyanines are also the isomeric compounds of the following formula IS and mixtures thereof:

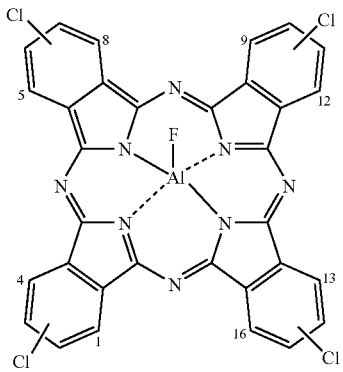
(IS)

where each isomer has a first chlorine substituent in the 1 or 4 position, a second chlorine substituent in the 5 or 8 position, a third chlorine substituent in the 9 or 12 position and a fourth chlorine substituent in the 13 or 16 position.

Preferred ortho-tetrachlorinated phthalocyanines are also the isomeric compounds of the following formula IT and mixtures thereof:

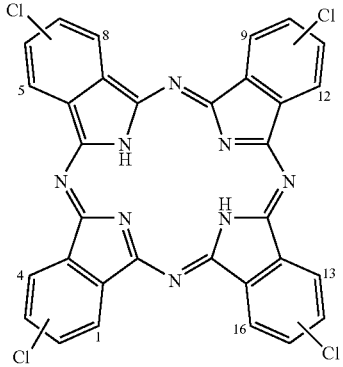
(IT)

where each isomer has a first chlorine substituent in the 1 or 4 position, a second chlorine substituent in the 5 or 8 position, a third chlorine substituent in the 9 or 12 position and a fourth chlorine substituent in the 13 or 16 position.

Preferred tetrafluorinated phthalocyanines are also the isomeric compounds of the following formulae IU, IV, IW, IX and IY and mixtures thereof:

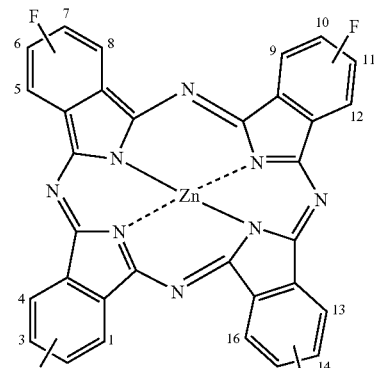
(IU)

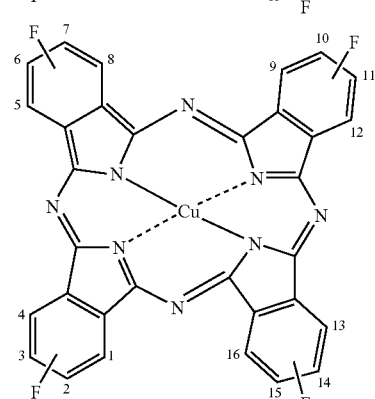
(IV)

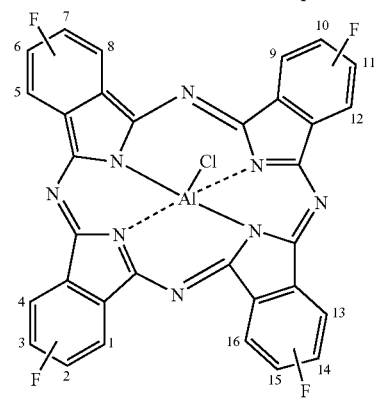
(IW)

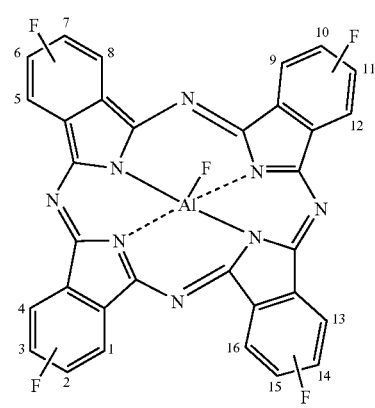
(IX)

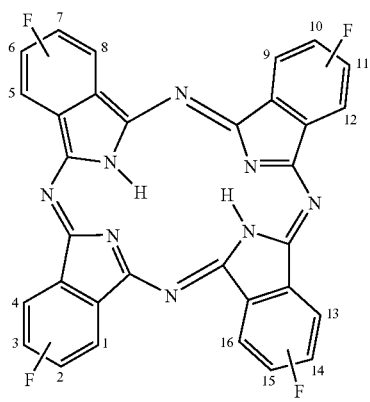

(IY)

where each isomer of the formulae IU, IV, IW, IX and IY has a first fluorine substituent in the 1 or 2 or 3 or 4 position, a second fluorine substituent in the 5 or 6 or 7 or 8 position, a third fluorine substituent in the 9 or 10 or 11 or 12 position and a fourth fluorine substituent in the 13 or 14 or 15 or 16 position.

Preferred tetrachlorinated phthalocyanines are also the isomeric compounds of the following formulae IZ, IZa, IZb, IZc and IZd and mixtures thereof:

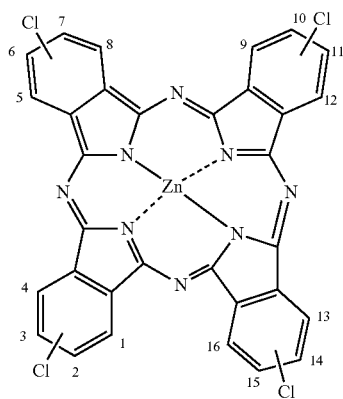

(IZ)

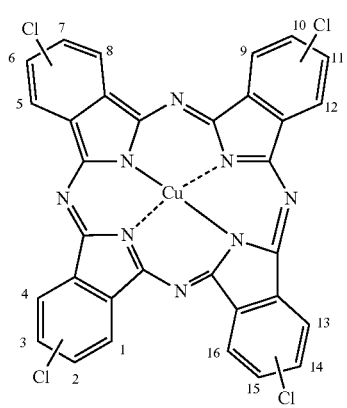

(IZa)

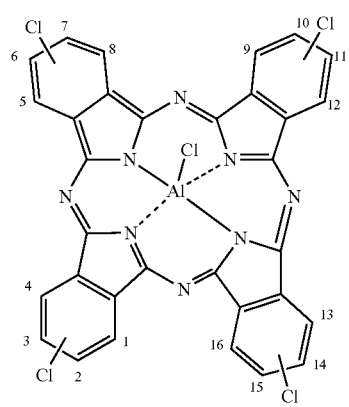

(IZb)

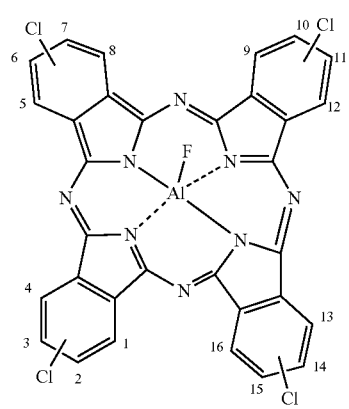

(IZc)

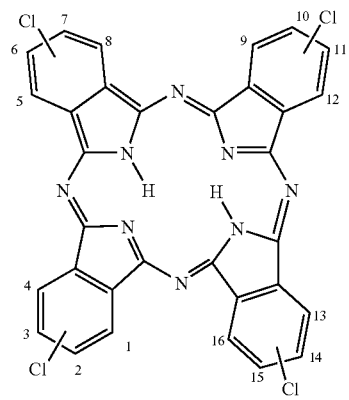

(IZd)

where each isomer of the formulae IZ, IZa, IZb, IZc and IZd has a first chlorine substituent in the 1 or 2 or 3 or 4 position, a second chlorine substituent in the 5 or 6 or 7 or 8 position, a third chlorine substituent in the 9 or 10 or 11 or 12 position and a fourth chlorine substituent in the 13 or 14 or 15 or 16 position.

Compounds of the general formulae Ia and Ib may be prepared in analogy to the methods described in literature or as described in the experimental part of this application. Some compounds of the general formulae Ia and Ib are also commercially available.

A suitable method for preparing meta-halogenated phthalocyanines of formula Ib is illustrated below for meta-tetrafluorinated phthalocyanines shown on the example of the isomeric compounds of the formula IB and mixtures thereof:

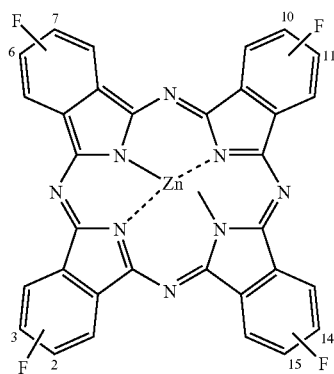

(IB)

where each isomer has a first fluorine substituent in the 2 or 3 position, a second fluorine substituent in the 6 or 7 position, a third fluorine substituent in the 10 or 11 position and a fourth fluorine substituent in the 14 or 15 position.

The isomeric compounds of the formula IB and mixtures thereof can be prepared by heating a mixture comprising 3-fluorophthalonitrile, urea and a zinc salt.

Preferably, the reaction is carried out in the presence of a catalyst. The catalyst can be selected from ammonium molybdate, ammonium phosphomolybdate and molybdenum oxide. Preference is given to using ammonium molybdate. The molar amount of the catalyst based on the total molar amount of 3-fluorophthalonitrile usually is 0.01 to 0.5 times, preferably 0.05 to 0.2 times.

The zinc salt can be selected from zinc halides, especially zinc chloride, zinc salt of a $C_1$-$C_6$-carboxylic acid, especially zinc acetate and zinc sulfate. In particular, the zinc salt used is zinc acetate. The molar amount of the zinc salt based on the total molar amount of 3-fluorophthalonitrile usually is 0.3 to 0.5 times.

According to a special embodiment, the reaction mixture also comprises zinc (0) as zinc source. Preferably, the zinc is in the form of zinc dust. In this embodiment, the molar amount of zinc based on the total molar amount of 3-fluorophthalonitrile usually is 0.2 times to 0.4 times, preferably 0.2 to 0.3 times, and the molar amount of zinc salt based on the total amount of 3-fluorophthalonitrile usually is 0.025 times to 0.05 times.

In general, the molar amount of urea based on the total molar amount of 3-fluorophthalonitrile is 1.5 times to 3 times.

The reaction is usually carried out in a solvent. Suitable solvents are organic solvents having a high boiling point, such as nitrobenzene, chlorinated benzene such as trichlorobenzene or chlorinated naphthalene and mixtures thereof. Particular preference is given to using nitrobenzene.

Preference is given to effecting the reaction under a protective gas atmosphere, for example nitrogen or argon. The reaction is usually carried out at a temperature between 140 to 220° C., preferably between 150 to 200° C. At this temperature, the mixture is usually allowed to react for 1 to 10 hours.

A skilled person will readily understand that isomeric compounds of formula Ib having a first halogen substituent in the 1 or 4 position, a second halogen substituent in the 5 or 8 position, a third halogen substituent in the 9 or 12 position and a fourth halogen substituent in the 13 or 16 position and mixtures thereof may be prepared similar to the method described above for meta-halogenated phthalocyanines of formula Ib.

A suitable method for preparing for preparing ortho-tetrafluorinated phthalocyanines is shown on the example of the isomeric compounds of the formula IG and mixtures thereof:

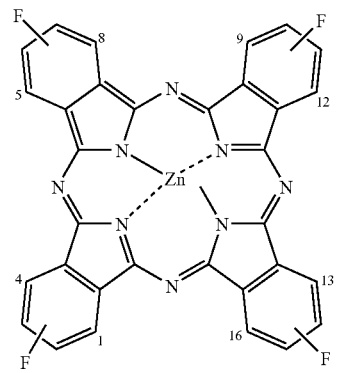

(IG)

where each isomer has a first fluorine substituent in the 1 or 4 position, a second fluorine substituent in the 5 or 8 position, a third fluorine substituent in the 9 or 12 position and a fourth fluorine substituent in the 13 or 16 position.

The isomeric compounds of the formula IG and mixtures thereof can be prepared by heating a mixture comprising 4-fluorophthalonitrile, urea and a zinc salt.

Preferably, the reaction is carried out in the presence of a catalyst.

As to the catalyst, zinc salt, urea, solvent and reaction conditions used, reference is made to what is said above for the preparation of isomeric compounds of formula IB and mixtures thereof.

The invention further relates to the use of the compounds of the formulae Ia and/or Ib as light absorbers.

Before the compounds of formulae Ia and Ib are used as charge transport materials or absorber materials, it may be advisable to subject them to a purification process. Suitable purification processes comprise conversion of the compounds of the formula Ia and Ib to the gas phase. This includes purification by sublimation or PVD (physical vapor deposition). Preference is given to a fractional sublimation. For fractional sublimation and/or deposition of the compound, a temperature gradient is used. Preference is given to subliming the compound of the formulae Ia and Ib with heating in a carrier gas stream. The carrier gas then flows through a separating chamber. A suitable separating chamber has at least two different separating zones with different temperatures. Preference is given to using a three-zone furnace. A suitable process and an apparatus for fractional sublimation is described in U.S. Pat. No. 4,036,594. Moreover, it is possible to purify the compounds of formulae Ia and Ib by fractional crystallization. A preferred solvent is sulfuric acid.

The compounds of the formulae Ia and Ib are suitable particularly advantageously as organic semiconductors. Depending on their purity, the position of the energy level of a further semiconductor material used in combination and/or any doping, they may be used as an electron donor (p-semiconductor) or electron acceptor (n-semiconductor).

The compounds of the formulae Ia and Ib are notable for their air stability.

The compounds of the formulae Ia and Ib are suitable with preference as a semiconductor material for organic field-effect transistors. They are preferably used as n-semiconductors. Likewise, preference is given to compounds of the formulae Ia and Ib to be used as p-semiconductors. The invention therefore further provides an organic field-effect transistor, comprising a substrate having at least one gate structure, a source electrode and a drain electrode and at least one compound of the formula Ia and/or Ib, as defined above, as a semiconductor, especially as an n-semiconductor.

Suitable substrates are in principle the materials known for this purpose. Suitable substrates comprise, for example, metals (preferably metals of groups 8, 9, 10 or 11 of the Periodic Table, such as Au, Ag, Cu), oxidic materials (such as glass, ceramics, $SiO_2$, especially quartz), semiconductors (e.g. doped Si, doped Ge), metal alloys (for example based on Au, Ag, Cu, etc.), semiconductor alloys, polymers (e.g. polyvinyl chloride, polyolefins such as polyethylene and polypropylene, polyesters, fluoropolymers, polyamides, polyimides, polyurethanes, polyalkyl(meth)acrylates, polystyrene and mixtures and composites thereof), inorganic solids (e.g. ammonium chloride), paper and combinations thereof. The substrates may be flexible or inflexible, and have a curved or planar geometry, depending on the desired use.

A typical substrate for semiconductor units comprises a matrix (for example a quartz or polymer matrix) and, optionally, a dielectric top layer.

Suitable dielectrics are anodized aluminum ($Al_2O_3$), $SiO_2$, polystyrene, poly-α-methylstyrene, polyolefins (such as polypropylene, polyethylene, polyisobutene), polyvinylcarbazole, fluorinated polymers (e.g. Cytop), cyanopullulans (e.g. CYMM), polyvinylphenol, poly-p-xylene, polyvinyl chloride, or polymers crosslinkable thermally or by atmospheric moisture.

Specific dielectrics are "self-assembled nanodielectrics", i.e. polymers which are obtained from monomers comprising SiCl functionalities, for example $Cl_3SiOSiCl_3$, $Cl_3Si$—$(CH_2)_6$—$SiCl_3$, $Cl_3Si$—$(CH_2)_{12}$—$SiCl_3$, and/or which are crosslinked by atmospheric moisture or by addition of water diluted with solvents (see, for example, Faccietti Adv. Mat. 2005, 17, 1705-1725). Instead of water, it is also possible for hydroxyl-containing polymers such as polyvinyl phenol or polyvinyl alcohol or copolymers of vinylphenol and styrene to serve as crosslinking components. It is also possible for at least one further polymer to be present during the crosslinking operation, for example polystyrene, which is then also crosslinked (see Facietti, US patent application 2006/0202195).

The substrate may additionally have electrodes, such as gate, drain and source electrodes of OFETs, which are normally localized on the substrate (for example deposited onto or embedded into a nonconductive layer on the dielectric). The substrate may additionally comprise conductive gate electrodes of the OFETs, which are typically arranged below the dielectric top layer (i.e. the gate dielectric).

The layer thicknesses are, for example, from 10 nm to 5 µm for semiconductors, from 50 nm to 10 µm for the dielectric; the electrodes may, for example, be from 20 nm to 1 µm thick.

In a specific embodiment, an insulator layer (gate insulating layer) is present on at least part of the substrate surface. The insulator layer comprises at least one insulator which is preferably selected from inorganic insulators such as $SiO_2$, SiN (silicon nitride), etc., ferroelectric insulators such as $Al_2O_3$, $Ta_2O_5$, $La_2O_5$, $TiO_2$, $Y_2O_3$, etc., organic insulators such as polyimides, benzocyclobutene (BCB), polyvinyl alcohols, polyacrylates, etc., and combinations thereof.

Suitable materials for source and drain electrodes are in principle electrically conductive materials. These include metals, preferably metals of groups 6, 7, 8, 9, 10 or 11 of the Periodic Table, such as Pd, Au, Ag, Cu, Al, Ni, Cr, etc. Also suitable are conductive polymers such as PEDOT (=poly(3,4-ethylenedioxythiophene)): PSS (=poly(styrenesulfonate)), polyaniline, surface-modified gold, etc. Preferred electrically conductive materials have a specific resistance of less than $10^{-3}$ ohm×meter, preferably less than $10^{-4}$ ohm×meter, especially less than $10^{-6}$ or $10^{-7}$ ohm×meter.

In a specific embodiment, drain and source electrodes are present at least partly on the organic semiconductor material. It will be appreciated that the substrate may comprise further components as used customarily in semiconductor materials or ICs, such as insulators, resistors, capacitors, conductor tracks, etc.

The electrodes may be applied by customary processes, such as evaporation, lithographic processes or another structuring process.

The compounds of the formula Ia and/or Ib used in accordance with the invention and the coated substrates produced therefrom are particularly advantageously suitable for use in organic field-effect transistors (OFETs). They may be used, for example, for the production of integrated circuits (ICs), for which customary n-channel MOSFETs (metal oxide semiconductor field-effect transistors) have been used to date. These are then CMOS-like semiconductor units, for example for microprocessors, microcontrollers, static RAM and other digital logic circuits. They are especially suitable for use in displays (specifically large-surface area and/or flexible displays) and RFID tags.

In a preferred embodiment, the inventive field-effect transistor is a thin-film transistor (TFT). In a customary construction, a thin-film transistor has a gate electrode disposed on the substrate, a gate insulation layer disposed thereon and on the substrate, a semiconductor layer disposed on the gate insulator layer, an ohmic contact layer on the semiconductor layer, and a source electrode and a drain electrode on the ohmic contact layer.

Various semiconductor architectures based on the inventive coated substrates are also conceivable, for example top contact, top gate, bottom contact, bottom gate, or else a vertical construction, for example a VOFET (vertical organic field-effect transistor), as described, for example, in US 2004/0046182.

A further aspect of the invention relates to the provision of electronic components which are based on the inventive substrates and comprise a plurality of semiconductor components, which may be n- and/or p-semiconductors. Examples of such components are field-effect transistors (FETs), bipolar junction transistors (BJTs), tunnel diodes, converters, light-emitting components, biological and chemical detectors or sensors, temperature-dependent detectors, photodetectors such as polarization-sensitive photodetectors, gates, AND, NAND, NOT, OR, TOR and NOR gates, registers, switches, timer units, static or dynamic stores and other dynamic or sequential, logical or other digital components including programmable circuits.

To produce OFETs, the surface of the substrate may be subjected to a modification before the deposition of at least one compound of the general formula Ia and/or Ib (and if appropriate of at least one further semiconductor material). This modification serves to form regions which bind the semiconductor materials and/or regions onto which no semiconductor materials can be deposited. Such processes are described, for example in U.S. Ser. No. 11/353,934 (=US 2007/01900783).

A specific semiconductor element is an inverter. In digital logic, the inverter is a gate which inverts an input signal. The inverter is also referred to as a NOT gate. Real inverter circuits have an output current which constitutes the opposite of the input current. Typical values are, for example, (0, +5V) for TTL circuits. The performance of a digital inverter reproduces the voltage transfer curve (VTC), i.e. the plot of input current against output current. Ideally, it is a staged function, and the closer the real measured curve approximates to such a stage, the better the inverter is. In a specific embodiment of the invention, the compounds of the formula Ia and/or Ib are used as organic n-semiconductors in an inverter.

The compounds of the formula Ia and/or Ib are also particularly advantageously suitable for use in organic photovoltaics (OPVs).

Organic solar cells generally have a layer structure and generally comprise at least the following layers: anode, photoactive layer and cathode. These layers are generally disposed on a substrate customary therefor. The structure of organic solar cells is described, for example, in US 2005/0098726 and US 2005/0224905, which are fully incorporated here by reference.

The invention further provides an organic solar cell comprising a substrate with at least one cathode, at least one anode and at least one compound of the formula Ia and/or Ib as defined above as a photoactive material.

Suitable substrates for organic solar cells are, for example, oxidic materials (such as glass, ceramic, $SiO_2$, especially quartz, etc.), polymers (e.g. polyvinyl chloride, polyolefins such as polyethylene and polypropylene, polyesters, fluoropolymers, polyamides, polyurethanes, polyalkyl(meth) acrylates, polystyrene and mixtures and composites thereof) and combinations thereof.

Suitable electrodes (cathode, anode) are in principle metals (preferably of groups 8, 9, 10 or 11 of the Periodic Table, e.g. Pt, Au, Ag, Cu, Al, In, Mg, Ca), semiconductors (e.g. doped Si, doped Ge, indium tin oxide (ITO), gallium indium tin oxide (GITO), zinc indium tin oxide (ZITO), etc.), metal alloys (e.g. based on Pt, Au, Ag, Cu, etc., especially Mg/Ag alloys), semiconductor alloys, etc. The anode used is preferably a material essentially transparent to incident light. This includes, for example, ITO, doped ITO, FTO (fluorine doped tin oxie), AZO (aluminium doped ZnO), ZnO, $TiO_2$, Ag, Au, Pt. The cathode used is preferably a material which essentially reflects the incident light. This includes, for example, metal films, for example of Al, Ag, Au, In, Mg, Mg/Al, Ca, etc.

For its part, the photoactive layer comprises at least one or consists of at least one layer which comprises, as an organic semiconductor material, at least one compound of the formulae Ia and/or Ib as defined above. In addition to the photoactive layer, there may be one or more further layers. These include, for example, layers with electron-conducting properties (electron transport layer, ETL)

layers which comprise a hole-conducting material (hole transport layer, HTL) which need not absorb, exciton- and hole-blocking layers (e.g. EBLs) which should not absorb, and multiplication layers.

Suitable exciton- and hole-blocking layers are described, for example, in U.S. Pat. No. 6,451,415.

Suitable materials for exciton blocker layers are, for example, bathocuproin (BCP), 4,4',4"-tris[3-methylphenyl-N-phenylamino]triphenylamine (m-MTDATA) or polyethylenedioxy-thiophene (PEDOT).

The inventive solar cells may be based on photoactive donor-acceptor heterojunctions. Upon optical excitation of an organic material, excitons are generated. For photocurrent to occur, the electron-hole pair has to be separated, typically at a donor-acceptor interface between two dissimilar contacting materials. At such an interface, the donor material forms a heterojunction with an acceptor material. If the charges do not separate, they can recombine in a geminant recombination process, also known as quenching, either radiatively, by the emission of light of a lower energy than the incident light, or non-radiatively, by the production of heat. Either of these outcomes is undesirable. When at least one compound of the formula Ia and/or Ib is used as the HTM (hole transport material), the corresponding ETM (electron transport material) must be selected such that, after excitation of the compounds, a rapid electron transfer to the ETM takes place. Suitable ETMs are, for example, C60 and other fullerenes, perylene-3,4;9,10-bis(dicarboximides) (PTCDIs), etc. When at least one compound of the formula Ia and/or Ib is used as the ETM, the complementary HTM must be selected such that, after excitation of the compound, a rapid hole transfer to the HTM takes place. The heterojunction may have a flat (smooth) configuration (cf. Two layer organic photovoltaic cell, C. W. Tang, Appl. Phys. Lett., 48 (2), 183-185 (1986) or N. Karl, A. Bauer, J. Holzäpfel, J. Marktanner, M. Mobus, F. Stölzle, Mol. Cryst. Liq. Cryst., 252, 243-258 (1994).) or be implemented as a bulk heterojunction or interpenetrating donor-acceptor network (cf., for example, C. J. Brabec, N. S. Sariciftci, J. C. Hummelen, Adv. Funct. Mater., 11 (1), 15 (2001).). Bulk heterojunctions are discussed in details below.

The compounds of the formula Ia and/or Ib can be used as a photoactive material in solar cells with MiM, pin, pn, Mip or Min structure (M=metal, p=p-doped organic or inorganic semiconductor, n=n-doped organic or inorganic semiconductor, i=intrinsically conductive system of organic layers; cf., for example, J. Drechsel et al., Org. Electron., 5 (4), 175 (2004) or Maennig et al., Appl. Phys. A 79, 1-14 (2004)).

The compounds of the formula Ia and/or Ib can also be used as a photoactive material in tandem cells, as described by P. Peumans, A. Yakimov, S. R. Forrest in J. Appl. Phys, 93 (7), 3693-3723 (2003) (cf. patents U.S. Pat. No. 4,461,922, U.S. Pat. No. 6,198,091 and U.S. Pat. No. 6,198,092) and are discussed in details below.

The compounds of the formula Ia and/or Ib can also be used as a photoactive material in tandem cells composed of two or more MiM, pin, Mip or Min diodes stacked on one another (cf. patent application DE 103 13 232.5) (J. Drechsel et al., Thin Solid Films, 451-452, 515-517 (2004)).

The layer thicknesses of the M, n, i and p layers are typically from 10 to 1000 nm, preferably from 10 to 400 nm. Thin layers can be produced by vapor deposition under reduced pressure or in inert gas atmosphere, by laser ablation or by solution- or dispersion-processable methods such as spin-coating, knife-coating, casting methods, spraying, dip-coating or printing (e.g. inkjet, flexographic, offset, gravure; intaglio, nanoimprinting).

In order to improve efficiency of an organic solar cell the average distance an exciton must diffuse from its generation to its dissociation site (donor-acceptor interface) can be reduced in an interpenetrating network of the donor and acceptor materials. FIG. 1 shows a nearly perfect morphology of a bulk-heterojunction with a great donor-acceptor interface area and continuous carrier conducting pathways to the opposing electrodes.

Bulk heterojunctions may be produced by a gas phase deposition process (physical vapor deposition, PVD). Suitable methods are described in US 2005/0227406, to which reference is made here. To this end, typically a compound of formulae Ia and/or Ib as electron donor and at least one electron acceptor material may be subjected to a vapor phase deposition by cosublimation. PVD processes are performed under high-vacuum conditions and comprise the following steps: evaporation, transport, deposition. The deposition is effected preferably at a pressure range from about $10^{-5}$ to $10^{-7}$ mbar. The deposition rate is preferably in a range from 0.01 to 10 nm/s. The deposition can be effected under an inert atmosphere, for example, under nitrogen, argon or helium. The temperature of the substrate in the deposition is preferably within a range from about −100 to 300° C., more preferably from −50 to 250° C.

The other layers of the solar cell can be produced by known methods. These include vapor deposition under reduced pressure or in inert gas atmosphere, by laser ablation or by solution- or dispersion-processable methods such as spin-coating, knife-coating, casting methods, spraying, dip-coating or printing (e.g. inkjet, flexographic, offset, gravure; intaglio, nanoimprinting). The complete solar cell is preferably produced by a gas phase deposition process.

The photoactive layer (mixed layer) can be subjected to a thermal treatment directly after its preparation or after the preparation of other layers being part of the solar cell. Annealing may improve the morphology of the photoactive layer. The temperature is preferably in the range of from 60 to 300° C. and the processing time ranges from 1 minute to 3 hours. In addition or alternatively to a thermal treatment, the photoactive layer may be subjected to a treatment using a solvent-containing gas. According to a suitable embodiment saturated solvent vapors in air at ambient temperature are used. Suitable solvents are toluene, xylene, chlorobenzene. trichloromethane, dichloromethane, N-methylpyrrolidone, N,N-dimethylformamide, ethyl acetate and mixtures thereof. The processing time usually ranges from 1 minute to 3 hours.

According to a preferred embodiment of the invention, the solar cell according to the present invention is a bulk-heterojunction single cell having a normal structure.

According to a specific embodiment the cell has the following structure:
a substrate essentially transparent to incident light
a first electrode (front electrode, anode)
hole transport layer (HTL)
mixed layer of a hole-conducting material and electron transport material in form of a bulk heterojunction
electron transport layer (ETL)
exciton blocking layer/electron transport layer
electrode (back electrode, cathode)

Figure 2:
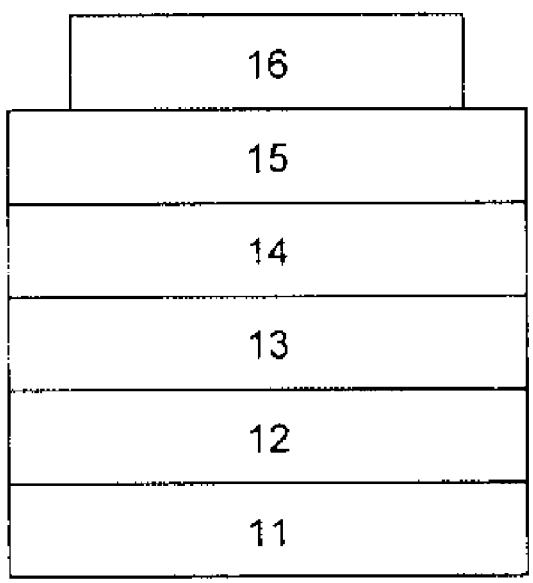
FIG. 2 illustrates a solar cell with a normal structure.

FIG. 2 illustrates a solar cell with normal structure according to the present invention. Preferably, the mixed layer consists of a compound of formula Ib and a fullerene, especially C60. Likewise preference is given to those mixed layers consisting of a compound of formula Ib and a rylene, especially 1,6,7,12-tetrachloroperylene-3,4:9,10-tetracarboximide. In particular, the compounds of formula Ib are selected from copper (ortho-tetrafluoro)phthalocyanine, copper (meta-tetrafluoro)phthalocyanine, copper (ortho+meta $F_4$)phthalocyanine, zinc (ortho-tetrafluoro)phthalocyanine, zinc (meta-tetrafluoro)phthalocyanine, zinc (ortho+meta $F_4$)phthalocyanine, zinc (ortho-tetrachloro)phthalocyanine, zinc (meta-tetrachloro)phthalocyanine, zinc (ortho+meta $Cl_4$)phthalocyanine, copper (diortho-octafluoro)phthalocyanine, copper (dimeta-octafluoro)phthalocyanine, zinc (diortho-octafluoro)phthalocyanine and zinc (dimeta-octafluoro)phthalocyanine. HTL and ETL can be either undoped or doped. Suitable dopants are discussed below.

According to further preferred embodiment of the invention, the solar cell according to the present invention is a bulk-heterojunction single cell having an inverse structure. The order of layer is the inverse of that of the normal structure. According to a specific embodiment the cell has the following structure:
a substrate essentially transparent to incident light
a first electrode (front electrode, cathode)
exciton blocking layer/electron transport layer
electron transport layer (ETL)
mixed layer of a hole-conducting material and electron transport material in form of a bulk heterojunction
hole transport layer (HTL)
electrode (back electrode, anode)

FIG. 3 illustrates a solar cell with inversion structure according to the present invention. Preferably, the mixed layer consists of a compound of formula Ib and a fullerene, especially C60. Likewise preference is given to those mixed layers consisting of a compound of formula Ib and a rylene, especially 1,6,7,12-tetrachloroperylene-3,4:9,10-tetracarboximide. In particular, the compounds of formula Ib are selected from copper (ortho-tetrafluoro) phthalocyanine, copper (meta-tetrafluoro)phthalocyanine, copper (ortho+meta $F_4$)phthalocyanine, zinc (ortho-tetrafluoro)phthalocyanine, zinc (meta-tetrafluoro)phthalocyanine, zinc (ortho+meta $F_4$)phthalaocyanine, zinc (ortho-tetrachloro) phthalocyanine, zinc (meta-tetrachloro)phthalocyanine, zinc (ortho+meta $Cl_4$)phthalocyanine, copper (diortho-octafluoro)phthalocyanine, copper (dimeta-octafluoro)phthalocyanine, zinc (diortho-octafluoro)phthalocyanine and zinc (dimetaoctafluoro)phthalocyanine. HTL and ETL can be either undoped or doped. Suitable dopants are discussed below.

According to further preferred embodiment of the invention, the solar cell according to the present invention is a bulk-heterojunction tandem cell.

A tandem cell comprises two or more than two, e.g. 3, 4, 5, etc., subcells. A single subcell, some of the subcells or all subcells may comprise a donor-acceptor heterojunction in form of a bulk heterojunction based on a compound of formulae Ia and/or Ib. Preferably, at least one of the subcells comprises a compound of formulae Ia or Ib and at least one fullerene, especially C60 or rylene, especially 1,6,7,12-tetrachloroperylene-3,4:9,10-tetracarboximide. In particular, the compounds of formula Ib are selected from copper (ortho-tetrafluoro)phthalocyanine, copper (meta-tetrafluoro)phthalocyanine, copper (ortho+meta $F_4$)phthalocyanine, zinc (ortho-tetrafluoro)phthalocyanine, zinc (meta-tetrafluoro) phthalocyanine, zinc (ortho+meta $F_4$)phthalaocyanine, zinc (ortho-tetrachloro)phthalocyanine, zinc (meta-tetrachloro) phthalocyanine, zinc (ortho+meta $Cl_4$)phthalocyanine, copper (diortho-octafluoro)phthalocyanine, copper (dimeta-octafluoro)phthalocyanine, zinc (diortho-octafluoro) phthalocyanine and zinc (dimetaoctafluoro)phthalocyanine.

The subcells forming the tandem cell may be connected in series or parallel. Preference is given to those tandem cells, wherein the subcells are connected in series. Preferably, an additional recombination layer is between the single subcells. Both normal structure and inverse structure can be used as subcell. However, the polarity of all subcells should be in one direction, i.e. all cells have a normal structure or all cells have an inverse structure.

FIG. 4 illustrates a tandem cell according to the present invention. Layer 31 is a transparent conducting layer. Suitable materials are those mentioned herein for the single cells.

Layer 32 and 34 are the individual subcells. Here, subcell refers to functional layers of a single cell, excluding cathode and anode. The subcells can be either all compound of formulae Ia and/or Ib—C60 cells or a compound of formulae Ia and/or Ib—C60 cell and another combination of semiconductor materials, such as C60 combined with metallophthalocyanines such as zinc phthalocyanine or copper phthalocyanine, dibenzotetraphenylperiflanthene, oligothiophenes such as α,α'-bis(2,2-dicyanovinyl)-quinquethiophene (DCV5T) and the like. The subcells can also be either all of compound of formulae Ia and/or Ib—PCBM ([6,6]-phenyl-C60-butyric acid methyl ester) cells or a compound of formulae Ia and/or Ib—PCBM cell and another combination of semiconductor material such as PCBM combined with poly(alkylthiophenes) such as poly(3-hexylthiophene). The subcells can also be either all of compound of formulae Ia and/or Ib-3,4,9,10-perylene tetracarboxylic acid bisbenzimidazole (PTCBI) cells or a compound of formulae Ia and/or Ib—PTCBI cell and another combination of semiconductor material such as PTCBI combined with poly(alkylthiophenes) such as poly(3-hexylthiophene). In particular, the compounds of formula Ib are selected from copper (ortho-tetrafluoro)phthalocyanine, copper (meta-tetrafluoro)phthalocyanine, copper (ortho+meta $F_4$)phthalocyanine, zinc (ortho-tetrafluoro)phthalocyanine, zinc (meta-tetrafluoro) phthalocyanine, zinc (ortho+meta $F_4$)phthalaocyanine, zinc (ortho-tetrachloro)phthalocyanine, zinc (meta-tetrachloro) phthalocyanine, zinc (ortho+meta $Cl_4$)phthalocyanine, copper (diortho-octafluoro)phthalocyanine, copper (dimeta-octafluoro)phthalocyanine, zinc (diortho-octafluoro) phthalocyanine and zinc (dimeta-octafluoro)phthalocyanine. In all cases, the best case is a combination of materials such a combination that the absorption of each subcell does not overlap too much, but is distributed over the solar spectrum, which in turns contributes to the higher photocurrent. For example, a second subcell with longer wavelength absorption is placed next to a first subcell having a shorter wavelength absorption than the first subcell to increase the absorption range. Preferably, the tandem cell can absorb in the region from 400 to 800 nm. Another subcell that can absorb from 800 nm and on can be placed next to the cell to increase the absorption to near infra red range. For best performance, the subcell with absorption in shorter wavelength is placed closer to the metal top contact than the subcell with the longer wavelength absorption.

The tandem cell may comprise a subcell, in which the photoactive donor-acceptor heterojunction is a flat heterojunction. In this case, the semiconductor materials mentioned herein below may be used which may be optionally doped. Suitable dopants are mentioned below.

Layer 33 is a recombination layer. The recombination layer enables one type of charge produced in one subcell to recombine to the other type of charge generated from adjacent subcells. Small metal clusters such as Ag, Au or combinations of highly doped n- and p-dopant layers can be used. In case of metal clusters, the thickness ranges from 0.5 to 5 nm. In the case of n- and p-dopant layers the thickness ranges from 5 to 40 nm. The recombination layer usually connects an electron transport layer of one subcell with the hole transport layer of the another subcell. In so doing this, further subcells may be combined to a tandem cell.

Layer 36 is the top electrode. The material of the top electrode depends on the polarity direction of the subcells. When the subcells take normal structure, the top metal is preferably made from low work function materials, such as Ag, Mg, Ca or Al. When the subcells take inverse structure, the top metal is preferably made from high work function materials such as Au, Pt, PEDOT-PSS.

In tandem structure connected in series, the overall voltage is the sum of the single subcells. The overall current is limited by the lowest current amongst the single subcells. For this reason, the thickness of each subcell should be re-optimized so that all subcell show similar current.

Examples of various types of donor-acceptor heterojunctions are a donor-acceptor bilayer forming a planar heterojunction or a hybrid planar-mixed heterojunction or a gradient bulk heterojunction or an annealed bulk heterojunction.

The preparation of a hybrid planar-mixed heterojunction is described in Adv. Mater. 17, 66-70 (2005). Coevaporated mixed heterojunction layers are sandwiched between homogenous donor and acceptors materials.

Figure 5:
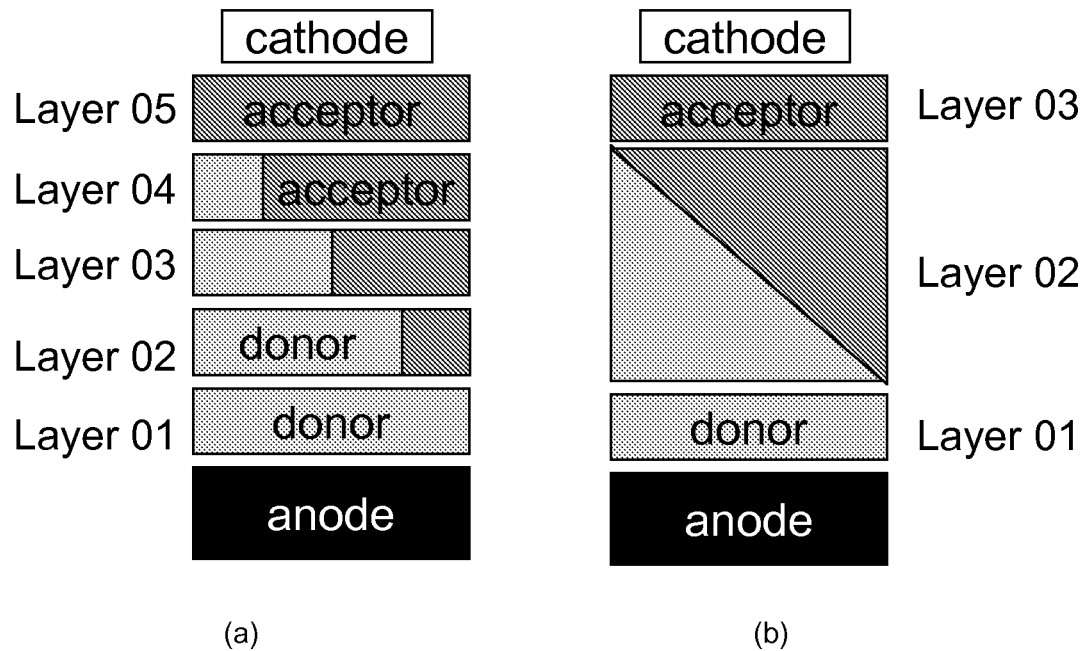

According to a specific embodiment of the invention, the donor-acceptor heterojunction is a gradient bulk heterojunction. The bulk heterojunction layer has a gradual change in donor-acceptor ratio. The cell can have stepwise gradient (FIG. 5 (a)), where layer 01 consists of 100% donor, layer 02 has donor/acceptor ratio>1, layer 03 has donor/acceptor ratio=1, layer 04 has donor/acceptor ratio<1, and layer 05 consists of 100% acceptor. It can also have smooth gradient. (FIG. 5 (b)) where layer 01 consists of 100% donor, layer 02 has decreasing ratio of donor/acceptor as the layer is distanced from the layer 01, and layer 03 consists of 100% acceptor. Different donor-acceptor ratio can be controlled by deposition rate of each material. Such structure can enhance the percolation path of charges.

According to a further specific embodiment of the invention, the donor-acceptor heterojunction is an annealed bulk heterojunction as described for example in Nature 425, 158-162, 2003. The method of fabricating said type of solar cell comprises an annealing step before or after metal deposition. With annealing, donor and acceptor materials can segregate which leads to larger percolation paths.

According to a further specific embodiment of the invention, the solar cells are prepared by organic vapor phase deposition in either a planar or controlled heterojunction architecture. Solar cells of this type are described in Materials, 4, 2005, 37.

According to a further preferred embodiment of the invention the organic solar cell comprises a metallophthalocyanine, e.g. copper phthalocyanine, an interlayer of a compound of formula Ia and/or Ib and an electron acceptor, e.g. a fullerene such as C60. Solar cells of this type are described in U.S. patent application Ser. No. 11/486,163. Without wishing to be bound to any theory, the purpose of the interlayer is to push the hole away from the disassociating interface, so that they don't come close together after they are separated from exciton to get lost by recombination. To achieve this, the interlayer has a deeper HOMO (larger ionization potential) than that of the donor, so that the holes drop to the donor immediately after disassociation has taken place. The interlayer should not block excitons from reaching the disassociating interface, and therefore has to have lower optical gap than the donor. The compound used in the interlayer must have absorption at equal or lower energy (longer wavelength) than the electron donor material. Suitable compounds for use in a cascade type interlayer between CuPc/C60 photovoltaic cell are compounds of formulae Ia and Ib, e.g. copper tetrafluorophthalocyanines, e.g. CuPc-(ortho-$F_4$), CuPc-(meta-$F_4$), CuPc-(otho+meta-$F_4$), zinc tetrafluorophthalocyanines, e.g. ZnPc-(ortho-$F_4$), ZnPc-(meta-$F_4$), ZnPc-(otho+meta-$F_4$), zinc tetrachlorophthalocyanines, e.g. ZnPc-(ortho-$Cl_4$), ZnPc-(meta-$Cl_4$), ZnPc-(otho+meta-$Cl_4$). The interlayer must be very thin (<4 nm), since the holes in the interlayer must "see" the donor, in order for them to fall to the HOMO of the donor.

Suitable organic solar cells may, as mentioned above, have at least one compound of the formula Ia and/or Ib used in accordance with the invention as an electron donor (p-semiconductor) or electron acceptor (n-semiconductor).

In addition to the compounds of the general formula Ia or Ib, the following semiconductor materials are suitable for use in organic photovoltaics: Phthalocyanines other than the compounds used in accordance with the invention. These include phthalocyanines which are unhalogenated or which bear more than 12 halogen substituents, such as hexadecachlorophthalocyanines and hexadecafluorophthalocyanines. They further include metal-free phthalocyanines or phthalocyanines which are unhalogenated or which bear more than 12 halogen substituents, comprising divalent metals or groups containing metal atoms, especially those of titanyloxy, vanadyloxy, iron, copper, zinc etc. Suitable phthalocyanines are especially copper phthalocyanine, zinc phthalocyanine, metal-free phthalocyanine, copper hexadecachlorophthalocyanine, zinc hexadecachlorophthalocyanine, metal-free hexadecachlorophthalocyanine, copper hexadecafluorophthalocyanine, zinc hexadecafluorophthalocyanine or metal-free hexadecafluorophthalocyanine.

Porphyrins, for example 5, 10,15,20-tetra(3-pyridyl)porphyrin (TpyP); or else tetrabenzoporphyrins, for example metal-free tetrabenzoporphyrin, copper tetrabenzoporphyrin or zinc tetrabenzoporphyrin; especially preferred are tetrabenzoporphyrins which, like the compounds of the formula (I) used in accordance with the invention, are processed as soluble precursors from solution and are converted to the pigmentary photoactive component on the substrate by thermolysis.

Acenes such as anthracene, tetracene, pentacene and substituted acenes. Substituted acenes comprise at least one substituent selected from electron-donating substituents (e.g. alkyl, alkoxy, ester, carboxylate or thioalkoxy), electron-withdrawing substituents (e.g. halogen, nitro or cyano) and combinations thereof. These include 2,9-dialkylpentacenes and 2,10-dialkylpentacenes, 2,10-dialkoxypentacenes, 1,4,8,11-tetraalkoxypentacenes and rubrene (5,6,11,12-tetraphenylnaphthacene). Suitable substituted pentacenes are described in US 2003/0100779 and U.S. Pat. No. 6,864,396. A preferred acene is rubrene (5,6,11,12-tetraphenylnaphthacene).

Liquid-crystalline (LC) materials, for example coronenes such as hexabenzocoronene (HBC-PhC$_{12}$), coronenediimides, or triphenylenes such as 2,3,6,7,10,11-hexahexylthiotriphenylene (HTT$_6$), 2,3,6,7,10,11-hexakis(4-n-nonylphenyl)-triphenylene (PTP$_9$) or 2,3,6,7,10,11-hexakis(undecyloxy)triphenylene (HAT$_{11}$). Particular preference is given to liquid-crystalline materials which are discotic. Suitable liquid-crystalline (LC) materials also include liquid crystalline phthalocyanines. These include phthalocyanines which bear $C_6$-$C_{18}$ alkyl, $C_6$-$C_{18}$ alkoxy and $C_6C_{18}$ alkoxycarbonyl radicals, wherein $C_6$-$C_{18}$ alkyl may be interrupted by oxygen. Suitable liquid crystalline phthalocyanines are described in Chem. Soc. Rev. 2007, 36, 1902-1929.

Thiophenes, oligothiophenes and substituted derivatives thereof. Suitable oligothiophenes are quaterthiophenes, quinquethiophenes, sexithiophenes, α,ω-di($C_1$-$C_{18}$)alkyloligothiophenes such as α,ω-dihexylquaterthiophenes, α,ω-dihexylquinquethiophenes and α,ω-dihexylsexithiophenes, poly(alkylthiophenes) such as poly(3-hexylthiophene), bis(dithienothiophenes), anthradithiophenes and dialkylanthradithiophenes such as dihexylanthradithiophene, phenylene-thiophene (P-T) oligomers and derivatives thereof, especially α,ω-alkyl-substituted phenylene-thiophene oligomers.

Also suitable are compounds of the α,α'-bis(2,2-dicyanovinyl)quinquethiophene (DCV5T) type, (3-(4-octylphenyl)-2,2'-bithiophene) (PTOPT), poly(3-(4'-(1,4,7-trioxaoctyl)phenyl)thiophene (PEOPT), poly(3-(2'-methoxy-5'-octylphenyl)thiophene) (POMeOPT), poly(3-octylthiophene) (P$_3$OT), poly(pyridopyrazinevinylene)-polythiophene blends such as EHH-PpyPz, PTPTB copolymers, BBL, F$_8$BT, PFMO; see Brabec C., Adv. Mater., 2996, 18, 2884, (PCPDTBT) poly[2,6-(4,4-bis(2-ethylhexyl)-4H-cyclopenta[2,1-b;3,4-b']-dithiophene)-4,7-(2,1,3-benzothiadiazole).

Poly-phenylene-ethynylene (PPE), paraphenylenevinylene and paraphenylenevinylene-comprising oligomers and polymers, for example polyparaphenylenevinylene, MEH-PPV (poly(2-methoxy-5-(2'-ethylhexyloxy)-1,4-phenylenevinylene)), MDMO-PPV (poly(2-methoxy-5-(3',7'-dimethyloctyloxy)-1,4-phenylenevinylene)), PPV, CN-PPV (with various alkoxy derivatives).

Phenyleneethynylene/phenylenevinylene hybrid polymers (PPE-PPV).

Polyfluorenes and alternating polyfluorene copolymers, for example with 4,7-dithien-2'-yl-2,1,3-benzothiadiazole. Also suitable are poly(9,9'-dioctylfluorene-co-benzothiadiazole) (F$_8$BT), poly(9,9'-dioctylfluorene-co-bis(N,N'-(4-butylphenyl))-bis(N,N'-phenyl)-1,4-phenylenediamine (PFB).

Polycarbazoles, i.e. carbazole-comprising oligomers and polymers.

Polyanilines, i.e. aniline-comprising oligomers and polymers.

Triarylamines, polytriarylamines, polycyclopentadienes, polypyrroles, polyfurans, polysiloles, polyphospholes, TPD, CBP, spiro-MeOTAD.

Rylenes (see below).

Fullerenes and fullerene derivatives, especially C60 and derivatives thereof such as PCBM (=[6,6]-phenyl-C60-butyric acid methyl ester) (see below).

In the context of this application, the term "fullerene" refers to a material which is composed of carbon and has a regular, three-dimensional network of fused carbon rings. These may have spherical, cylindrical, ovoid, flattened or angular structures. Suitable fullerenes are, for example, C60, C70, C76, C80, C82, C84, C86, C90, C96, C120, single-walled carbon nanotubes (SWNT) and multi-walled carbon nanotubes (MWNT). Examples of fullerene derivatives are phenyl-C$_{61}$-butyric acid methyl ester, phenyl-C$_{71}$-butyric acid methyl ester ([71]PCBM), phenyl-C$_{84}$-butyric acid methyl ester ([84]PCBM), phenyl-C$_{61}$-butyric acid butyl ester ([60]PCBB), phenyl-C$_{61}$-butyric acid octyl ester ([60]PCBO) and thienyl-C$_{61}$-butyric acid methyl ester([60]ThCBM). Particular preference is given to using C60. Also suitable are fullerene derivatives such as PCBM (=[6,6]-phenyl-C60-butyric acid methyl ester).

In organic solar cells, particular preference is given to using a combination of semiconductor materials which comprises at least one tetrafluorinated or tetrachlorinated phthalocyanine and C60. In a specific embodiment, the tetrafluorinated phthalocyanine is an isomeric mixture of copper (ortho-tetrafluoro)phthalocyanine, an isomeric mixture of copper (meta-tetrafluoro)phthalocyanine, an isomeric mixture of copper (ortho- and meta-tetrafluoro)phthalocyanine, in which each isomer has a first fluorine substituent in the 1 or 2 or 3 or 4 position, a second fluorine substituent in the 5 or 6 or 7 or 8 position, a third fluorine substituent in the 9 or 10 or 11 or 12 position and a fourth fluorine substituent in the 13 or 14 or 15 or 16 position, an isomeric mixture of zinc (ortho-tetrafluoro)phthalocyanine, an isomeric mixture of zinc (meta-tetrafluoro)phthalocyanine or an isomeric mixture of zinc (ortho- and meta-tetrafluoro)phthalocyanine, in which each isomer has a first fluorine substituent in the 1 or 2 or 3 or 4 position, a second fluorine substituent in the 5 or 6 or 7 or 8 position, a third fluorine substituent in the 9 or 10 or 11 or 12 position and a fourth fluorine substituent in the 13 or 14 or 15 or 16 position. In a further specific embodiment, the tetrachlorinated phthalocyanine is an isomeric mixture of copper (ortho-tetrachloro)phthalocyanine, an isomeric mixture of copper (meta-tetrachloro)phthalocyanine, an isomeric mixture of copper (ortho- and meta-tetrachloro)phthalocyanine, in which each isomer has a first chlorine substituent in the 1 or 2 or 3 or 4 position, a second chlorine substituent in the 5 or 6 or 7 or 8 position, a third chlorine substituent in the 9 or 10 or 11 or 12 position and a fourth chlorine substituent in the 13 or 14 or 15 or 16 position, an isomeric mixture of zinc (ortho-tetrachloro)phthalocyanine, an isomeric mixture of zinc (meta-tetrachloro)phthalocyanine or an isomeric mixture of zinc (ortho- and meta-tetrachloro)phthalocyanine, in which each isomer has a first chlorine substituent in the 1 or 2 or 3 or 4 position, a second chlorine substituent in the 5 or 6 or 7 or 8 position, a third chlorine substituent in the 9 or 10 or 11 or 12 position and a fourth chlorine substituent in the 13 or 14 or 15 or 16 position.

Particularly preferred is a combination of semiconductor materials which comprises at least one copper (ortho-tetrafluoro)phthalocyanine and C60. Particularly preferred is also a combination of semiconductor materials which comprises at least one zinc (ortho-tetrafluoro)phthalocyanine and C60. Particularly preferred is also a combination of semiconductor materials which comprises at least one zinc (meta-tetrafluoro)phthalocyanine and C60. Particularly preferred is also a combination of semiconductor materials which comprises at least one copper (ortho-tetrafluoro)phthalocyanine and PCBM. Particularly preferred is also a combination of semiconductor materials which comprises at least one zinc (ortho-tetrafluoro)phthalocyanine and PCBM. Particularly preferred is also a combination of semiconductor materials which comprises at least one zinc (meta-tetrafluoro)phthalocyanine and PCBM.

Particularly preferred is a combination of semiconductor materials which comprises at least one copper (meta-tetrafluoro)phthalocyanine and C60. Particularly preferred is also a combination of semiconductor materials which comprises at least one zinc (meta-tetrafluoro)phthalocyanine and C60. Particularly preferred is also a combination of semiconductor materials which comprises at least one copper (meta-tetrafluoro)phthalocyanine and PCBM. Particularly preferred is also a combination of semiconductor materials which comprises at least one zinc (meta-tetrafluoro)phthalocyanine and PCBM.

In the context of this application, the term "rylenes" refers to compounds having a molecular structure of naphthalene units linked in the peri position. According to the number of naphthalene units, they may, for example, be perylenes (n=2), terrylenes (n=3), quaterrylenes (n=4) or higher rylenes. Accordingly, they may be perylenes, terrylenes or quaterrylenes of the following formula

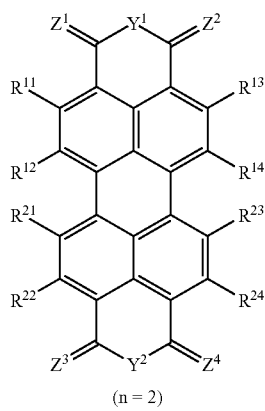

(n = 2)

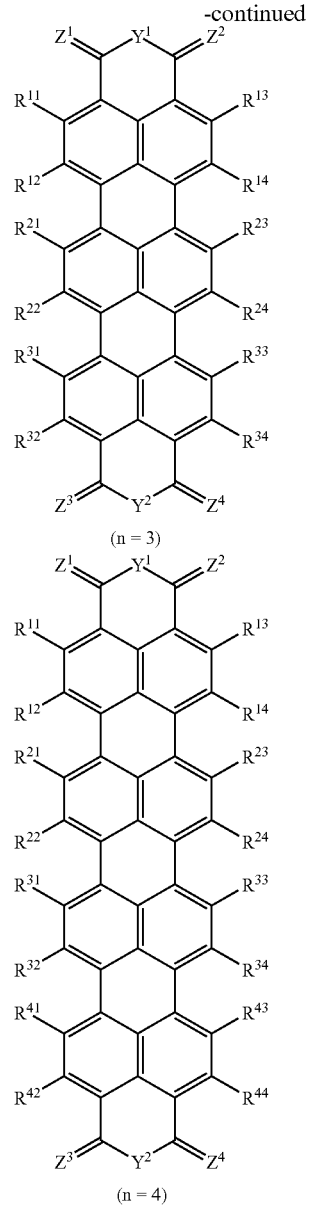

(n = 3)

(n = 4)

in which the $R^{n1}$, $R^{n2}$, $R^{n3}$ and $R^{n4}$ radicals where n is from 1 to 4 may each independently be hydrogen, halogen or groups other than halogen, $Y^1$ is O or $NR^a$, where $R^a$ is hydrogen or an organyl radical,
$Y^2$ is O or $NR^b$, where $R^b$ is hydrogen or an organyl radical,
$Z^1$, $Z^2$, $Z^3$ and $Z^4$ are each O, where, in the case that $Y^1$ is $NR^a$, one of the $Z^1$ and $Z^2$ radicals may also be $NR^c$, where the $R^a$ and $R^c$ radicals together are a bridging group having from 2 to 5 atoms between the flanking bonds, and where, in the case that $Y^2$ is $NR^b$, one of the $Z^3$ and $Z^4$ radicals may also be $NR^d$, where the $R^b$ and $R^d$ radicals together are a bridging group having from 2 to 5 atoms between the flanking bonds.

Suitable rylenes are, for example, described in PCT/EP2006/070143 (=WO2007/074137), PCT/EP2007/051532 (=WO2007/093643) and PCT/EP2007/053330 (=WO2007/116001), to which reference is made here.

In organic solar cells, particular preference is given to using a combination of semiconductor materials which comprises at least one octafluorinated or octachlorinated phthalocyanine used in accordance with the invention and 1,6,7,12-tetrachloroperylene-3,4:9,10-tetracarboximide.

Likewise, preference is given to using a combination of semiconductor materials which comprises at least one octafluorinated or octachlorinated phthalocyanine used in accordance with the invention and perylene-3,4:9,10-tetracarboxylic acid bisbenzimidazole (PTCBI). In a specific embodiment, the octafluorinated phthalocyanine is an isomeric mixture of copper (diortho-octafluoro)phthalocyanine, an isomeric mixture of copper (dimeta-octafluoro)phthalocyanine, an isomeric mixture of zinc (diortho-octafluoro)phthalocyanine or an isomeric mixture of zinc (dimeta-octafluoro)phthalocyanine. In a further specific embodiment, the octachlorinated phthalocyanine is an isomeric mixture of copper (diortho-octachloro) phthalocyanine, an isomeric mixture of copper (dimeta-octachloro)phthalocyanine, an isomeric mixture of zinc (diortho-octafluoro)phthalocyanine or an isomeric mixture of zinc (dimeta-octafluoro)phthalocyanine.

In organic solar cells, particular preference is given to using a combination of semiconductor materials which comprises at least one tetrafluorinated or tetrachlorinated phthalocyanine used in accordance with the invention and 1,6,7,12-tetrachloroperylene-3,4:9,10-tetracarboximide.

Likewise, preference is given to using a combination of semiconductor materials which comprises at least one octafluorinated or octachlorinated phthalocyanine used in accordance with the invention and 1,6,7,12-tetrachloroperylene-3,4:9,10-tetracarboximide. In a specific embodiment, the tetrafluorinated phthalocyanine is an isomeric mixture of copper (ortho-tetrafluoro)phthalocyanine, an isomeric mixture of copper (meta-tetrafluoro)phthalocyanine, an isomeric mixture of copper (ortho- and meta-tetrafluoro)phthalocyanine, in which each isomer has a first fluorine substituent in the 1 or 2 or 3 or 4 position, a second fluorine substituent in the 5 or 6 or 7 or 8 position, a third fluorine substituent in the 9 or 10 or 11 or 12 position and a fourth fluorine substituent in the 13 or 14 or 15 or 16 position, an isomeric mixture of zinc (ortho-tetrafluoro)phthalocyanine, an isomeric mixture of zinc (meta-tetrafluoro)phthalocyanine or an isomeric mixture of zinc (ortho- and meta-tetrafluoro)phthalocyanine, in which each isomer has a first fluorine substituent in the 1 or 2 or 3 or 4 position, a second fluorine substituent in the 5 or 6 or 7 or 8 position, a third fluorine substituent in the 9 or 10 or 11 or 12 position and a fourth fluorine substituent in the 13 or 14 or 15 or 16 position. In a further specific embodiment, the tetrachlorinated phthalocyanine is an isomeric mixture of copper (ortho-tetrachloro)phthalocyanine, an isomeric mixture of copper (meta-tetrachloro)phthalocyanine, an isomeric mixture of copper (ortho- and meta-tetrachloro)phthalocyanine, in which each isomer has a first chlorine substituent in the 1 or 2 or 3 or 4 position, a second chlorine substituent in the 5 or 6 or 7 or 8 position, a third chlorine substituent in the 9 or 10 or 11 or 12 position and a fourth chlorine substituent in the 13 or 14 or 15 or 16 position, an isomeric mixture of zinc (ortho-tetrachloro)phthalocyanine, an isomeric mixture of zinc (meta-tetrachloro)phthalocyanine or an isomeric mixture of zinc (ortho- and meta-tetrachloro)phthalocyanine, in which each isomer has a first chlorine substituent in the 1 or 2 or 3 or 4 position, a second chlorine substituent in the 5 or 6 or 7 or 8 position, a third chlorine substituent in the 9 or 10 or 11 or 12 position and a fourth chlorine substituent in the 13 or 14 or 15 or 16 position.

Particularly preferred is a combination of semiconductor materials which comprises at least one copper (ortho-tetrafluoro)phthalocyanine and 1,6,7,12-tetrachloroperylene-3,4:9,10-tetracarboximide. Particularly preferred is also a combination of semiconductor materials which comprises at least one zinc (ortho-tetrafluoro)phthalocyanine and C60. Particularly preferred is also a combination of semiconductor materials which comprises at least one zinc (meta-tetrafluoro) phthalocyanine and C60.

According to a preferred embodiment of the invention, the solar cell according to the present invention is a bulk-heterojunction solar cell having the following structure:
ITO/
(0 nm-20 nm) compound of formula Ia and/or Ib/
(10 nm-80 nm) C60: compound of formula Ia and/or Ib in the ratio 1:10 to 10:1, preferably 1:2 to 2:1
(10 nm-60 nm) C60
(1 nm-10 nm) BOP/
Ag All aforementioned semiconductor materials may also be doped. The conductivity of such semiconductor material may be enhanced through the use of chemical doping techniques using various electron acceptor and/or electron donor dopants. In a specific embodiment, the compound of the formula Ia and/or Ib and/or (if present) a different semiconductor material is thus used in the inventive organic solar cells in combination with at least one dopant. The organic material may be doped with an n-dopant having a HOMO energy level close to or higher in energy to the LUMO energy level of the electron conducting material. The organic material may be doped with a p-dopant having a LUMO energy level close to or lower in energy to the HOMO energy level of the hole conducting material. In other words, in the case of n-doping, an electron is released from the dopant acting as donor, whereas in the case of p-doping, the dopant acting as acceptor absorbs an electron.

Suitable dopants for use of the compounds Ia and Ib as n-semiconductors are $Cs_2CO_3$, LiF, pyronin B (PyB), rhodamine derivatives, especially rhodamine B, cobaltocene, etc, in particular pyronin B and rhodamine derivatives.

Examples of suitable dopants for p-semiconductors are $WO_3$, $MoO_3$, 2,3,5,6-tetrafluoro-7,7,8,8-tetracyanoquinodimethane ($F_4$-TCNQ), 3,6-difluoro-2,5,7,7,8,8-hexacyanoquinodimethane, dichlorodicyanoquinone (DDQ) or tetracyanoquinodimethane (TCNQ), especially 3,6-difluoro-2,5,7,7,8,8-hexacyanoquinodimethane.

Typically, the dopants may be employed in concentrations of up to about 10 mole percent based on the semiconductor material to be doped, preferably up to 5 mole percent based on the semiconductor material to be doped. In particular, a dopant is employed in an amount of 0.1 to 3 mole percent, based on the semiconductor material to be doped.

The invention further relates to an organic light-emitting diode (OLED) which comprises at least one compound of the formula Ia and/or Ib used in accordance with the invention. The compounds of the formula Ia and/or Ib may serve as a charge transport material (especially as electron conductor).

Organic light-emitting diodes are formed in principle from several layers. These include: 1. anode, 2. hole-transporting layer, 3. light-emitting layer, 4. electron-transporting layer and 5. cathode. It is also possible that the organic light-emitting diode does not have all of the layers mentioned; for example, an organic light-emitting diode with the layers (1) (anode), (3) (light-emitting layer) and (5) (cathode) is likewise suitable, in which case the functions of the layers (2) (hole-transporting layer) and (4) (electron-transporting layer) are assumed by the adjacent layers. OLEDs which have the layers (1), (2), (3) and (5) or the layers (1), (3), (4) and (5) are likewise suitable. The structure of organic light-emitting diodes and processes for their production are known in principle to those skilled in the art, for example from WO 2005/019373. Suitable materials for the individual layers of OLEDs are disclosed, for example in WO 00/70655. Reference is made here to the disclosure of these documents. The application of compounds Ia and/or Ib on a substrate can be produced by vapor deposition by customary techniques, i.e. by thermal evaporation, chemical vapor deposition and others.

The invention is illustrated in detail by the nonrestrictive examples which follow.

EXAMPLES

Abbreviations Used

CuPc copper phthalocyanine
$CuPcF_8$ 2,3,6,7,10,11,14,15-octafluorocopper phthalocyanine
$CuPcF_4$ tetrafluorocopper phthalocyanine
$CuPc\text{-}oF_4$ (ortho-tetrafluoro)copper phthalocyanine
$CuPc\text{-}m\,F_4$ (meta-tetrafluoro)copper phthalocyanine
$CuPc\text{-}(o+m)F_4$ (ortho+meta-tetrafluoro)copper phthalocyanine
$CuPcCl_8$ 2,3,6,7,10,11,14,15-octachlorocopper phthalocyanine
$ZnPc\text{-}oF_4$ (ortho-tetrafluoro)zinc phthalocyanine
$ZnPc\text{-}mF_4$ (meta-tetrafluoro)zinc phthalocyanine
C60 [60]fullerene
PEDOT poly(3,4-ethylenedioxythiophene)
BCP bathocuproine
BPE-PTCDI N,N'-bis(2-phenylethyl)perylene-3,4:9,10-bis (dicarboximide)
Bphen 4,7-diphenyl-1,10-phenanthroline
PTCBI 3,4,9,10-perylene tetracarboxylic acid bisbenzimidazole
PEDOT-PSS poly(3,4-ethylenedioxythiophene)-poly(styrenesulfonate)
ITO indium tin oxide

I. Preparation of the Halogenated Phthalocyanines

Example 1

2,3,6,7,10,11,14,15-octafluorocopper phthalocyanine (Route a—in the presence of solvent)

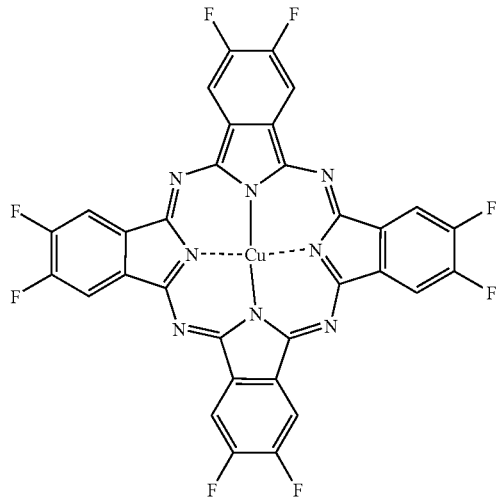

1.1 4,5-difluorophthalonitrile

A mixture of 300 ml of xylene, 5.0 g (20 mmol) of N,N'-dimethylimidazolidino-tetramethylguanidinium chloride and 58.1 g (1000 mmol) of dry KF was heated to 50° C. To this were added 19.7 g (100 mmol) of 4,5-dichlorophthalonitrile and the mixture was heated to 120° C. for 13 hours. The mixture was filtered and the solvent was removed under reduced pressure. The crude compound was purified by column chromatography using 1:1 toluene/petroleum ether as the eluent to obtain 11.96 g (73%) of the title compound as a white substance.

1.2 2,3,6,7,10,11,14,15-octafluorocopper phthalocyanine

A mixture of 100 ml of nitrobenzene, 13.13 g (80 mmol) of 4,5-difluorophthalonitrile, 2.18 g (22 mmol) of CuCl and 0.29 g (2 mmol) of $MoO_3$ was subjected to the action of ammonia (1 bar) and heated to 200° C. The mixture was kept at this temperature under ammonia for 2 hours. Thereafter, 100 ml of nitrobenzene were added and the ammonia stream was stopped. The mixture was stirred at this temperature for a further 3 hours, allowed to cool to room temperature, washed with ethanol and dried under reduced pressure. 10.88 g (76%) of the title compound were obtained as blue powder.
Fractional Crystallization:
Fractional Crystallization a)
  7.0 g of the crude product were dissolved in 350 g of 98% sulfuric acid. The solution was heated to 50° C. and 490 g of 50% sulfuric acid were added with stirring within 20 hours. The resulting suspension of 70% sulfuric acid was stirred for a further 16 hours, the suspension was allowed to cool slowly to room temperature and then filtered. The filtercake was washed with 50% sulfuric acid and then with water to obtain 0.93 g (13%) of the title compound.
Fractional Crystallization b)
  The above-described crystallization was repeated to obtain the title compound in a yield of 87%.
Fractional Crystallization c)
  The above-described crystallization was repeated to obtain the title compound in a yield of 74%.

Example 2

2,3,6,7,10,11,14,15-octafluorocopper phthalocyanine (Route b—in the absence of solvent)

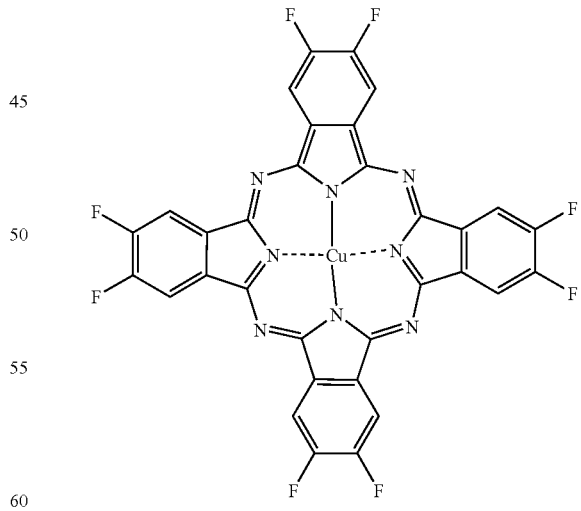

A mixture of 1.3 g (8 mmol) of 4,5-difluorophthalonitrile, 0.22 g (2.2 mmol) of CuCl and 29 mg (0.2 mmol) of $MoO_3$ was heated to 220° C. in an oil bath. The melt was heated to a temperature above 255° C. with stirring. After 10 minutes, the mixture was allowed to cool to room temperature, and the reaction mixture was poured on to 1 M hydrochloric acid, stirred at 50° C. and filtered. The residue was washed with 1

M NaOH, filtered and dried. 1.06 g (74%) of the title compound were obtained as a blue powder.
$\lambda_{max}$ (H$_2$SO$_4$)=255 l/g cm (758 nm)

Example 3

3a) Preparation of 2,3,6,7,10,11,14,15-octachlorocopper phthalocyanine

A mixture of 100 ml of nitrobenzene, 10.1 g (51 mmol) of 4,5-dichlorophthalonitrile, 1.39 g (14 mmol) of CuCl and 0.21 g (1.5 mmol) of MoO$_3$ was subjected to the action of 1 bar of ammonia. Thereafter, the mixture was heated to 200° C. and the mixture was stirred at this temperature for 3 hours. The mixture was filtered, washed with methanol and dried under reduced pressure. 9.83 g of the title compound were obtained as a blue powder.
$\lambda_{max}$ (H$_2$SO$_4$)=270 L/g cm (801 nm)

3b) Further Purification

Fractional Crystallization 18.0 g of the crude product were dissolved in 900 g of 98% sulfuric acid and diluted with 1260 g of 50% sulfuric acid. The solution was heated to 50° C. The procedure was repeated two more times to yield 15.3 g (63%) of the purified material.
$\lambda_{max}$ (H$_2$SO$_4$)=285 L/g cm (760 nm).

3c) Further Purification

Gradient Sublimation 1.8 g of the material obtained from example 3b were sublimed in a three zone gradient sublimation apparatus at 40° C., 250° C. and 425° C. 0.9 g of the title compound were received.
$\lambda_{max}$ (H$_2$SO$_4$)=282 L/g cm (760 nm).

Examples 3c shows that octachlorocopper phthalocyanine can be purified by gradient sublimation and can be used for organic cells processed from vacuum.

Example 4

Mixture of Tetrafluorophthalocyanines (CuPc-mF$_4$) of the Following Formula

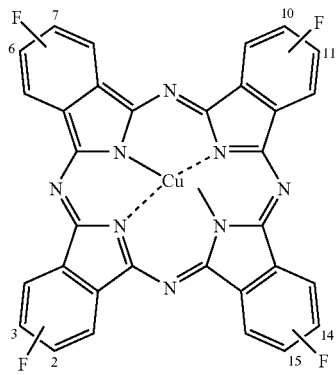

in which each isomer has a first fluorine substituent in the 2 or 3 position, a second fluorine substituent in the 6 or 7 position, a third fluorine substituent in the 10 or 11 position and a fourth fluorine substituent in the 14 or 15 position.

4a) Preparation

A mixture of 2.92 g (20 mmol) of 4-fluorophthalonitrile, 1.99 g (10 mmol) of copper acetate monohydrate, 2.00 g (33 mmol) of urea and a catalytic amount of ammonium molybdate in 25 ml of nitrobenzene was heated to 160° C. under nitrogen for 5 h. Thereafter, the mixture was allowed to cool to room temperature, diluted with toluene and filtered. The resulting crude product was washed cautiously with acetone, water and acetonitrile.

For purification, the crude product was dissolved in formic acid and precipitated with acetonitrile. This procedure was repeated twice. Subsequently, a second purification step followed, in which the title compound was dissolved in dimethylformamide and precipitated with ethanol. 2.13 g (65.7%) of the title compound were obtained.

4b) Further Purification

Gradient Sublimation

For further purification, 0.383 g of the title compound was subjected to a temperature gradient of room temperature, 200° C. and 390° C. In the interior of the tube, 0.198 g of the title compound was obtained:
$\lambda_{max}$ (H$_2$SO$_4$)=780.5 nm

Example 5

Mixture of tetrafluorophthalocyanines (CuPc-oF$_4$) of the following general formula

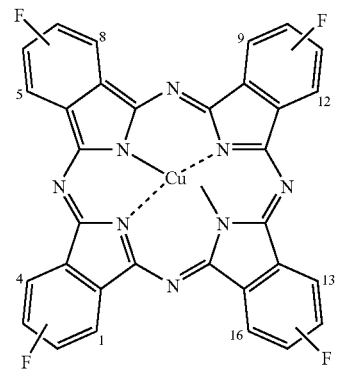

in which each isomer has a first fluorine substituent in the 1 or 4 position, a second fluorine substituent in the 5 or 8 position, a third fluorine substituent in the 9 or 12 position and a fourth fluorine substituent in the 13 or 16 position.

5a)

A mixture of 4.38 g (30 mmol) of 3-fluorophthalonitrile, 1.99 g (10 mmol) of copper acetate monohydrate, 3.00 g (50 mmol) of urea and a catalytic amount of ammonium molybdate in 25 ml of nitrobenzene was heated to 160° C. under nitrogen for 7 h. Thereafter, the mixture was allowed to cool to room temperature, diluted with toluene and filtered. The resulting crude product was washed cautiously with acetone, water and acetonitrile.

Purification of the crude product was carried out by dissolving it in 98% $H_2SO_4$ followed by precipitating the acid solution in cold water. Further purification was effected by stirring the product in 38% $H_2SO_4$ for 15 minutes and the solids were separated by using a centrifuge. This process was repeated until the filtrate was colorless. The solid obtained was then washed thoroughly with water, acetone and then dried. Yield after purification 3.9 g (81.3%).

5b)

Subsequent purification was carried out using gradient sublimation technique inside a three zone furnace oven. 1.56 g of material were exposed to a temperature gradient of 425, 250° and room temperature. 0.95 g of product were collected in the first zone.

$\lambda_{max}$ ($H_2SO_4$)=819.0 nm

Example 6

Mixture of tetrafluorozincphthalocyanines (ZnPc-oF$_4$) of the following formula

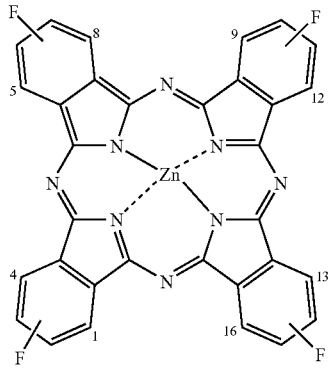

in which each isomer has a first fluorine substituent in the 1 or 4 position, a second fluorine substituent in the 5 or 8 position, a third fluorine substituent in the 9 or 12 position and a fourth fluorine substituent in the 13 or 16 position.

6a) Using Zinc Acetate as Precursor

A mixture of 5.84 g (40 mmol) of 3-fluorophthalonitrile, 2.44 g (13.3 mmol) of zinc acetate, 4.00 g (66.6 mmol) of urea and 0.08 g of ammonium molybdate in 20 mL of nitrobenzene was heated to 180° C. under argon for 7 h. Then, the mixture was cooled to room temperature and filtered. The solid obtained after filtration was washed thoroughly with ethanol. Further purification of the crude product was carried out by dissolving the crude product in formic acid and precipitating it in acetonitrile. This procedure was repeated twice and followed up with a second purification step by dissolving the product in formic acid and precipitating it using ethanol. The dark blue solid obtained was dried under vacuum to yield 1.0 g (15.4%) of the pure product.

6b) Using Zinc Powder as Precursor

A mixture of 5.0 g (33.6 mmol) of 3-fluorophthalonitrile, 0.53 g (8.1 mmol) of zinc dust, 0.22 g, (1.2 mmol) of zinc acetate, 0.16 g (2.55 mmol) of urea and 0.031 g (0.16 mmol) of ammonium molybdate in 11 mL of distilled nitrobenzene was heated to 100° C. under argon for 30 minutes and subsequently at 190° C. for about 3 hours. Then the solids obtained were filtered, washed with methanol, acetone and Tetrahydrofuran (THF) to afford a dirty blue green solid. Further purification of the crude product was carried out using formic acid and methanol to yield a dark blue solid, yield 2.0 g (36%).

For both procedure 6a) and 6b), MALDI-TOF Mass: Mass Calculated for $C_{32}H_{12}F_4N_8Zn$=649, Obtained=648.7 (in DHB ((2,5-dihydroxybenzoic acid) matrix); $^1$H NMR (THF-d8): 9.12-9.21 (m, 4H), 8.1-8.2 (m, 4H), and 7.82-7.90 (m, 4H) ppm; UV-vis: $\lambda_{max}$ (conc. $H_2SO_4$)=813 nm.

6c) Further Purification (Gradient Sublimation) of Example 6a)

For further purification, 0.8 g of the title compound was subjected to a temperature gradient of room temperature, 250° C. and 450° C. in vacuum less than $2\times10^{-5}$ mbar. In the interior of the tube, 0.48 g (yield 60%) of the title compound was obtained:

6d) Further Purification (Gradient Sublimation) of Example 6b)

For further purification, 1.55 g of the title compound was subjected to a temperature gradient of room temperature, 250° C. and 350° C. in vacuum less than $2\times10^{-5}$ mbar. In the interior of the tube, 0.99 g (yield 64%) of the title compound was obtained:

Example 7

Mixture of tetrafluorozincphthalocyanines (ZnPc-mF$_4$) of the following formula

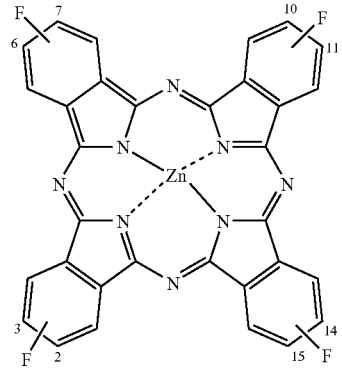

in which each isomer has a first fluorine substituent in the 2 or 3 position, a second fluorine substituent in the 6 or 7 position, a third fluorine substituent in the 10 or 11 position and a fourth fluorine substituent in the 14 or 15 position.

A mixture of 7.3 g (50 mmol) of 4-fluorophthalonitrile, 3.29 g (15 mmol) of zinc acetate monohydrate, 5.00 g (83.3 mmol) of urea and 0.08 g of ammonium molybdate in 20 mL nitrobenzene was heated to 160° C. under argon for 7 h. Then, the reaction mixture was cooled, and the solid obtained was filtered, washed with acetonitrile and water. Purification was done by dissolving the crude product in dimethyl sulphoxide and precipitated using water. The solid obtained by filtration was washed thoroughly with water and dried. The filtrate obtained was diluted with ethanol and kept overnight which resulted in precipitation of more solids which were collected by filtration and purified separately.

Further purification of the two crude products was carried out separately by dissolving them in formic acid followed by precipitating it using acetonitrile. This procedure is repeated twice and followed up with a second purification step by dissolving the product in formic acid and precipitating it using ethanol. The dark blue solid obtained was dried under vacuum to yield=0.64 g and 2.06 g respectively. Combined yield was 2.7 G (33.3%).

MALDI-TOF Mass: Mass Calculated for $C_{32}H_{12}F_4N_8Zn$=649, Obtained=647.89 (without matrix); UV-vis: $\lambda_{max}$ (Con. $H_2SO_4$)=775 nm.

Example 8

Mixture of tetrafluorocopperphthalocyanines (CuPc-(o+m)F$_4$) of the following formula

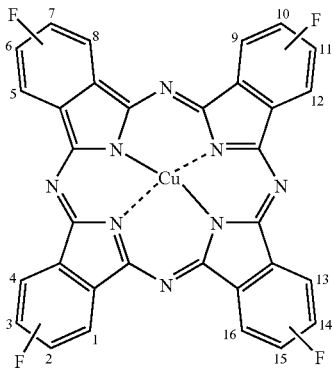

in which each isomer has a first fluorine substituent in the 1 or 2 or 3 or 4 position, a second fluorine substituent in the 5 or 6 or 7 or 8 position, a third fluorine substituent in the 9 or 10 or 11 or 12 position and a fourth fluorine substituent in the 13 or 14 or 15 or 16 position.

A mixture of 1.46 g (10 mmol) of 3-fluorophthalonitrile, 1.46 g (10 mmol) of 4-fluorophthalonitrile, 1.33 g (6.66 mmol) of copper acetate monohydrate, 2.0 g (33.3 mmol) of urea and 0.025 g of ammonium molybdate in 20 mL of nitrobenzene was heated to 165° C. under argon for 6 h. The reaction mixture was cooled to room temperature and diluted with acetone and the solid obtained was filtered, washed thoroughly with acetone and dried to yield 3.5 g of the crude product. The crude product was washed several times with 40% sulphuric acid and finally with water and acetone to yield a dark blue solid which was dried under vacuum to yield 1.9 g (58.8%) of the title compound.

MALDI-TOF Mass: Mass Calculated for $C_{32}H_{12}F_4N_8Cu$=648, Obtained=646.87 (Without matrix); UV-vis: $\lambda_{max}$ (Con. $H_2SO_4$)=800.5 nm.

Example 9

Mixture of tetrachlorozincphthalocyanines (ZnPc-oCl$_4$) of the following general formula

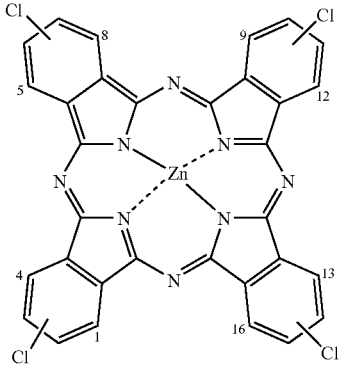

in which each isomer has a first chlorine substituent in the 1 or 4 position, a second chlorine substituent in the 5 or 8 position, a third chlorine substituent in the 9 or 12 position and a fourth chlorine substituent in the 13 or 16 position.

9a)

A mixture of 1.62 g (10 mmol) of 3-chlorophthalonitrile, 0.60 g (3.3 mmol) of zinc acetate, 1.00 g (16.7 mmol) of urea and 0.02 g of ammonium molybdate in 10 mL of nitrobenzene was heated to 185° C. under argon for 7 h. Then, the reaction mixture was cooled to room temperature and the solid obtained was filtered and washed thoroughly with ethanol.

Further purification of the crude product was carried out by dissolving the crude product in formic acid and precipitating it using acetonitrile. This procedure was repeated twice and followed up with a second purification step were the solids were dissolved in formic acid and then precipitated using methanol. Yield after purification, 1.6 g (89.6%) of the title compound.

MALDI-TOF Mass: Mass Calculated for $C_{32}H_{12}Cl_4N_8Zn$=713, Obtained=714.5 (With DHB matrix); $^1$H NMR (THF-d8): 8.9-9.08 (bm, 4H) and 7.90-8.06 (bm, 8H) ppm; UV-vis: $\lambda_{max}$ (con. $H_2SO_4$)=818.5 nm.

9b)

Subsequent purification was carried out using gradient sublimation technique inside a three zone furnace oven. 1.21 g of material were exposed to a temperature gradient of 500, 375° and 50° C. 0.05 g of product were collected in the first zone.

Example 10

Mixture of tetrafluoro aluminumchloridephthalocyanines (AlClPc-oF$_4$) of the following general formula

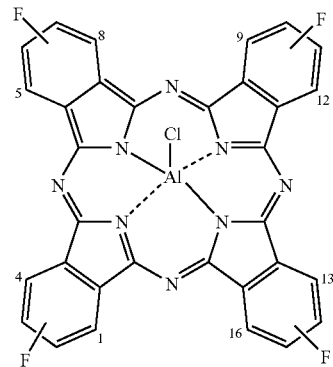

in which each isomer has a first fluorine substituent in the 1 or 4 position, a second fluorine substituent in the 5 or 8 position, a third fluorine substituent in the 9 or 12 position and a fourth fluorine substituent in the 13 or 16 position 10a)

A mixture of 2.92 g (20 mmol) of 3-fluorophthalonitrile, 0.93 g (7 mmol) of anhydrous aluminium chloride, 2 g (33.3 mmol) of urea and 0.04 g of ammonium molybdate were dissolved in 10 mL of nitrobenzene and stirred at 180° C. under argon for 18 h. Then, the reaction mixture was cooled to room temperature and diluted with acetonitrile. The blue solid precipitated was filtered and washed well with ethanol and acetonitrile. Further purification of the crude product was carried out by dissolving the solid in dimethylformamide and precipitating it using acetonitrile. The solid obtained was filtered and dried to yield 1.2 g (37.3%) after purification.

MALDI-TOF Mass: Mass Calculated for $C_{32}H_{12}ClF_4N_8Al$=646, Obtained=645.96 (Without Matrix); UV-vis: $\lambda_{max}$ (Con. $H_2SO_4$)=833 nm.

10b)

Subsequent purification was carried out using gradient sublimation technique inside a three zone furnace oven. 1.02 g of material were exposed to a temperature gradient of 425, 300° and room temperature. 0.11 g (11% yield) of product were collected in the first zone.

II. Use of the Halogenated Phthalocyanines According to the Present Invention Construction of a Solar Cell In a standard construction, the organic solar cell is produced on a glass substrate which has been coated with a transparent conductive indium tin oxide layer (ITO). To improve the contact properties, an additional layer of PEDOT can be applied between ITO electrode and the absorber. The absorber layer which follows consists of an electron donor and an electron acceptor, one of the materials being a halogenated phthalocyanine. The counterelectrode applied by vapor deposition is a metal, e.g. silver or aluminum.

Characteristics of a Solar Cell:
SC short circuit
$I_{sc}$ short-circuit current $I_{sc}$, delivered by a solar cell when the two terminals are connected without any additional resistance
$J_{sc}$ short-circuit current density
OC open circuit
$V_{OC}$ open-circuit voltage—voltage present in the unloaded/unlit state
FF filling factor
η efficiency
Conversion: 1 sun=100 mW/cm²

Example 11

Solar Cell Based on $CuPcF_8$ Doped with Pyronin B and CuPc

ITO glass was purchased from Merck. The glass substrate was cleaned by means of ultrasound in boiling acetone.

Subsequently, the layers of the solar cell were applied in a high-vacuum chamber ($10^{-7}$ mbar; vacuum system from Lesker) at the given deposition temperatures and rates.

The $CuPcF_8$ obtained in Example 1 after crystallization by fractional crystallization c) was doped by cosublimation with pyronin B (1:7% by weight).

| ITO substrate | | |
|---|---|---|
| CuPc | 23 nm | 0.1-0.5 nm/s |
| CuPcF₈ | 34 nm | 0.1-0.5 nm/s |
| Ag | 100 nm | 0.5 nm/s |
| Size | 7.3 * 10⁻⁴ cm² | |
| Illuminance | 0.85 suns | |
| $V_{OC}$ | 410 mV | |
| $J_{SC}$ | 1.22 mA/cm² | |
| FF | 56% | |
| η | 0.32% | |

Figure 6:
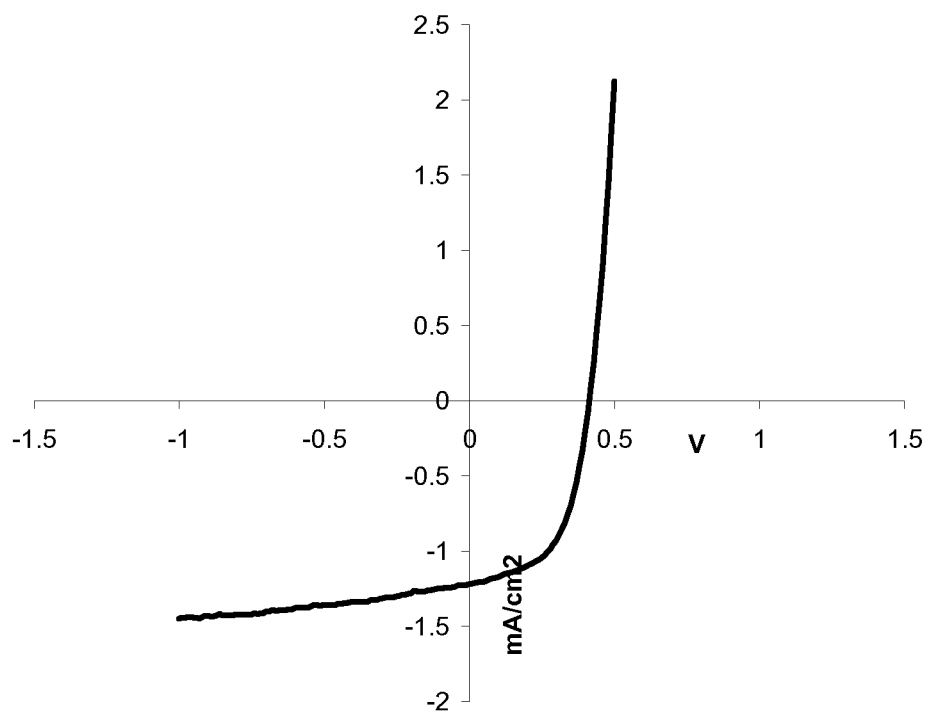

The results are shown graphically in FIG. 6.

Example 11 shows that $CuPcF_8$ can be used as an n-semiconductor.

In the following examples 12 to 17, the solar cell were prepared as follows:

ITO Preparation

Indium tin oxide (ITO) on glass substrate is purchased from Merck Display Technologies Ltd. The Thickness of the ITO layer was 140±15 nm, and had a sheet resistance of 11.70Ω per square. The ITO was cleaned by following procedure. First the ITO was cleaned in 5% RB535 detergent bath for 5 minutes, rinsed in deinoized water for 5 minutes, followed by cleaning in boiling acetone 2 times for 5 minutes and isopropanol 2 times for 5 minutes. Cleaning was completed by subjecting the ITO an ultrasonic bath in 150° C. N-Methyl-2-pyrrolidone (NMP) for 5 minutes.

PEDOT-PSS (Poly(3,4-ethylenedioxythiophene)poly(styrenesulfonate) Layer Deposition For deposition of PEDOT-PSS(H. C. Starks A14083), ITO substrates were UV ozoned prior to spin coating. A UV lamp (FHR Anlagenbau Gmbh) with power of 50 mW/cm² was used. The UV ozoned ITO was brought into a glove box to be coated with PEDOT-PSS. The spin coating was done within 30 minutes after the UV ozoning procedure. Dispersion of PEDOT-PSS was spun at 2500 RPM for 5 seconds and ramped up to 6000 RPM for 25 seconds, followed by annealing in nitrogen at 100° C. for 20 minutes.

Polyamide Insulating Layer

Polyamide resin (Supelco) may be applied for the insulation between top and bottom electrode. The sample was placed at 200° C. for 15 minutes for curing.

Light Source

AM 1.5 simulator from Solar Light Co. Inc using xenon lamp (Model 16S-150 V3), if not stated to the contrary (was this light source also used in examples 14) The UV region under 415 nm was filtered and IV measurement was performed at ambient condition.

Reference Cell

The solar simulator intensity is calibrated with monocrystalline FZ silicon solar cell (Fraunhofer ISE).

Materials

CuPc obtained from BASF, 1 time purified by sublimation purification

C60 obtained from NeoTech Prodocut, 1 time purified by sublimation purification

BCP obtained from Sensient Technology, 1 time purified by sublimation purification Ag obtained from Acros organics, used as received CuPc-(o+m)F4: as described by above procedure, 1 time purified by sublimation purification Evaporation The thickness of the evaporated layers (for both organic and metal) was monitored with quartz crystal monitor (QCM). The tooling factor was calibrated with ellipsometry measurement.

Temperature

The temperature was recorded with thermocouple directly in contact with the bottom of the crucible.

| | |
|---|---|
| CuPc | 420 ± 20° C. |
| C60 | 460 ± 20° C. |
| BCP | 110 ± 20° C. |
| CuPc-mF₄ | 400 ± 20° C. |
| CuPc-oF4 | 400 ± 20° C. |

Bilayer Cell Fabrication

Comparative Example 12

ITO/PEDOT-PSS/CuPc/C60/BCP/Ag

ITO was prepared as described in ITP preparation and PEDOT-PSS was prepared as described in PEDOT-PSS layer deposition. The Insulating layer was painted on the part of the sample for insulation between bottom (PEDOT-PSS) and top (Ag) electrode. The rest of the evaporation (both organics and metals) are done in high vacuum chamber (p<$10^{-7}$ torr)

| CuPc | 20 nm | 0.1 nm/sec |
|---|---|---|
| C60 | 40 nm | 0.1 nm/sec |
| BCP | 4 nm | 0.1 nm/sec |
| Ag | 100 nm | 0.1 nm/sec |

Cell size=0.01 cm$^2$
Measured under 1 Sun intensity (100 mW/cm$^2$)

| $V_{OC}$ | 520 mV |
|---|---|
| $J_{SC}$ | 5.4 mA/cm$^2$ |
| FF | 50% |
| η | 1.4% |

$J_{sc}$ and η are lower than the best reported values in US2002189666, S. Forrest et al. 2002. This may be due to different material quality. In addition, the light source used filters out UV light, where C60 shows large photon-to-charge conversion (350-400 nm).

Example 13

ITO/PEDOT-PSS/CuPc-mF4/C60/BCP/Ag

The solar cell was constructed as described in Example 12. CuPc-mF4 from Example 4b was used. Cell size and measurement condition same as measurements with <ITO/PEDOT-PSS/CuPc/C60/BCP/Ag> in example 12

| CuPc-mF4 | 20 nm | 0.1 nm/sec |
|---|---|---|
| $V_{OC}$ | 740 mV | |
| $J_{SC}$ | 1.3 mA/cm$^2$ | |
| FF | 31% | |
| η | 0.3% | |

Example 14

ITO/PEDOT-PSS/CuPc-oF4/C60/BCP/Ag

The solar cell was constructed as described in Example 12. One time sublimed CuPc-oF4 from Example 5 was used. Cell size and measurement condition are the same as measurements with <ITO/PEDOT-PSS/CuPc/C60/BCP/Ag> device from example 12.

| CuPc-oF4 | 20 nm | 0.1 nm/sec |
|---|---|---|
| $V_{OC}$ | 660 mV | |
| $J_{SC}$ | 4.0 mA/cm$^2$ | |
| FF | 37% | |
| η | 1.1% | |

Bulk Heterojunction Cell Fabrication
<ITO/CuPc:C60(1:1)/C60/BCP/Ag>

ITO was prepared as described in example 12 and no PEDOT-PSS layer was deposited. The device showed better efficiency without PEDOT-PSS. Insulating layer was painted on the part of the sample for insulation between bottom (ITO) and top (Ag) electrode. The rest of the evaporation (both organics and metals) are done in high vacuum chamber (p<$10^{-7}$ torr)

Comparative Example 15

The CuPc:C60 heterojunction layer is deposited by co-evaporation. Two separate quartz crystal monitor was used to monitor the rate of each organic source, and the mixture ratio between two materials was based on wt % measured by each QCM.

| CuPc:C60 1:1 | 60 nm | 0.1 nm/sec for both material |
|---|---|---|
| C60 | 2 nm | 0.1 nm/sec |
| BCP | 4 nm | 0.1 nm/sec |
| Ag | 100 nm | 0.1 nm/sec |

Cell size = 0.01 cm$^2$

Measured under 1 Sun intensity (100 mW/cm$^2$)

| $V_{OC}$ | 480 mV |
|---|---|
| $J_{SC}$ | 12.6 mA/cm$^2$ |
| FF | 38% |
| η | 2.3% |

$J_{sc}$ and η are lower than the best reported values in Applied Physics Letters 84, 4218 S. Uchida et al. 2004. This may be due to different material quality and/or different thickness compared to cited reference. In addition, the light source used in this examples filters out UV light, where C60 shows large photon-to-charge conversion (350-400 nm). This could have decreased the overall current, hence power conversion efficiency η.

Example 16

ITO/CuPc-oF4:C60(1:1)/C60/BCP/Ag

CuPc-oF4 was taken from example 5b. Same substrate procedure was taken and same device structure was used as in comparative example 15 device.
Cell size and measurement condition are the same as measurements with <ITO/CuPc:C60(1:1)/C60/BCP/Ag> comparative example 15.

| $V_{OC}$ | 485 mV |
|---|---|
| $J_{SC}$ | 1.1 mA/cm$^2$ |
| FF | 30% |
| η | 0.15% |

In the following examples 17 to 22 the solar cell were prepared as follows

Substrate Preparation

Patterned ITO substrate was received from Lehrstuhl für Bildschirmtechnik (Stuttgart). The thickness of the ITO layer is 140 nm and the RMS (roughness mean square) was <5 nm. The substrate was UV ozoned for 20 minutes prior to organic deposition. No additional hole transporting layer, such as PEDOT-PSS was applied Basic Measurement Setup Same procedure was taken as in examples 11 to 16. All the measurement was performed under 1 Sun intensity (100 mW/cm$^2$).

| Materials | | |
|---|---|---|
| C60 | from Alfa Aeser/CreaPhys sublimed grad. | Used as recieved |
| Bphen | from Sigma Aldrich | used as received |
| Ag | from Acros organics | used as received |

Evaporation

Two types of cells (bilayer and bulk heterojunction(BHJ)) were fabricated in high vacuum system (pressure<10-6 mbar)

The bilayer cell (ITO/example material/C60/Bphen/Ag) was built with (example materials) and C60 evaporated in turns on ITO substrate. Deposition rate was 0.1 nm/sec for (example materials) layer and 0.2 nm/sec for C60 layer. Bphen evaporation was followed on top of the mixed layer. The evaporation temperature for the materials 470° C. for ZnPc-oF$_4$, 450° C. for ZnPc-mF$_4$, 330° C. for ZnPc-oCl$_4$, 390° C. for C60 and 120° C. for Bphen. Finally 100 nm of Ag was evaporated for the top contact.

The bulk heterojunction cell (ITO/example material:C60 (1:1)/C60/Bphen/Ag) structure was built. The example material and C60 were coevaporated on ITO at same rate (0.1 nm/sec) to have 1:1 volume ratio of DBP and C60 mixed layer. Additional C60 layer is evaporated at rate of 0.2 nm/sec followed by Bphen and Ag layer deposition, unless otherwise explained. Same evaporation condition was used as in the case of bilayer devices.

In all examples 18 to 23, the device had an area of 0.03 cm$^2$. Thicknesses of each layer are optimized to yield highest efficiency, and are mentioned in each example.

Bilayer Cell Fabrication

Example 17

ITO/ZnPc-mF$_4$/C60/Bphen/Ag

ZnPc-m F$_4$ from Example 7 was used.

| thickness | |
|---|---|
| ZnPc-mF$_4$ | 20 nm |
| C60 | 40 nm |
| Bphen | 6 nm |
| Ag | 100 nm |
| $V_{OC}$ | 680 mV |
| $J_{SC}$ | 2.3 mA/cm$^2$ |
| FF | 46% |
| η | 0.7% |

Example 18

18a)

<ITO/ZnPc-oF4/C60/Bphen/Ag>

ZnPc-oF4 from Example 6c (Zn acetate precursor, one time sublimed) was used.

| thickness | |
|---|---|
| ZnPc-oF$_4$ | 20 nm |
| C60 | 40 nm |
| Bphen | 6 nm |
| Ag | 100 nm |
| $V_{OC}$ | 700 mV |
| $J_{SC}$ | 5.64 mA/cm$^2$ |
| FF | 70% |
| η | 2.76% |

18b)

<ITO/ZnPc-oF$_4$/C60/Bphen/Ag>

ZnPc-oF$_4$ from Example 6d (Zn powder precursor, one time sublimed) was used.

| thickness | |
|---|---|
| ZnPc-oF$_4$ | 40 nm |
| C60 | 40 nm |
| Bphen | 6 nm |
| Ag | 100 nm |
| $V_{OC}$ | 700 mV |
| $J_{SC}$ | 5.67 mA/cm$^2$ |
| FF | 63% |
| η | 2.5% |

As in the case of CuPc, fluorinated ones yielded higher $V_{OC}$ than unsubstituted Pc's. In addition the material with the -ortho position yields better result compared to -meta position in bilayer cells.

Example 19

ITO/ZnPc-oCl$_4$/C60/Bphen/Ag

ZnPc-oCl$_4$ from Example 9b (one time sublimed) was used.

| thickness | |
|---|---|
| ZnPc-oCl$_4$ | 10 nm |
| C60 | 40 nm |
| Bphen | 6 nm |
| Ag | 100 nm |
| $V_{OC}$ | 660 mV |
| $J_{SC}$ | 4.23 mA/cm$^2$ |
| FF | 71% |
| η | 2.0% |

Chlorinated copperphthalocyanine also showed higher $V_{OC}$ than unsubstituted copperphthalocyanine.

Example 20

ITO/CuPc-(o+m) F$_4$/C60/Bphen/Ag

CuPc-(o+m)F$_4$ from Example 8 was used.

| thickness | |
|---|---|
| CuPc-(o + m)F$_4$ | 15 nm |
| C60 | 40 nm |

-continued

| thickness | |
|---|---|
| Bphen | 6 nm |
| Ag | 100 nm |
| $V_{OC}$ | 740 mV |
| $J_{SC}$ | 1.35 mA/cm$^2$ |
| FF | 39% |
| η | 0.38% |

Bulk Heterojunction Cell Fabrication

Example 21

21a)

<ITO/ZnPc-oF$_4$:C60 (1:1)/C60/Bphen/Au>
ZnPc-oF$_4$ from Example 6c (Zn acetate precursor, one time sublimed) was used.

| thickness | |
|---|---|
| ZnPc-oF$_4$:C60 | 40 nm |
| C60 | 20 nm |
| Bphen | 6 nm |
| Au | 80 nm |
| $V_{OC}$ | 660 mV |
| $J_{SC}$ | 10.1 mA/cm$^2$ |
| FF | 50% |
| η | 3.2% |

21b)

<ITO/ZnPc-oF$_4$:C60 (1:1)/C60/Bphen/Ag>
ZnPc-oF$_4$ from Example 6c (Zn acetate precursor, one time sublimed) was used.

| thickness | |
|---|---|
| ZnPc-oF$_4$:C60 | 30 nm |
| C60 | 20 nm |
| Bphen | 6 nm |
| Ag | 100 nm |
| $V_{OC}$ | 640 mV |
| $J_{SC}$ | 11.5 mA/cm$^2$ |
| FF | 50% |
| η | 3.6% |

21c)

<ITO/ZnPc-oF$_4$:C60 (1:1)/C60/Bphen/Ag>
ZnPc-oF$_4$ from Example 6d (Zn powder precursor, one time sublimed) was used.

| thickness | |
|---|---|
| ZnPc-oF$_4$:C60 | 40 nm |
| C60 | 40 nm |
| Bphen | 6 nm |
| Au | 80 nm |
| $V_{OC}$ | 640 mV |
| $J_{SC}$ | 11.5 mA/cm$^2$ |
| FF | 52% |
| η | 3.8% |

Example 22

ITO/ZnPc-oCl$_4$:C60 (1:1)/C60/Bphen/Au

| thickness | |
|---|---|
| ZnPc-oCl$_4$:C60 | 40 nm |
| C60 | 20 nm |
| Bphen | 6 nm |
| Ag | 100 nm |
| $V_{OC}$ | 680 mV |
| $J_{SC}$ | 10.3 mA/cm$^2$ |
| FF | 44% |
| η | 3.1% |

Cascade Type Interlayer

Example 23

ITO/PEDOT-PSS/CuPc/CuPc-oF4/C60/BCP/Ag

CuPc-oF4 used as an interlayer to enhance charge extraction.

Same substrate procedure was taken and same device structure was used as in Example 12. CuPc-oF4 was taken from example 5b.

| | | |
|---|---|---|
| CuPc | 17 nm | 0.1 nm/sec |
| CuPc-oF4c | 2 nm | 0.1 nm/sec |
| C60 | 40 nm | 0.1 nm/sec |
| BCP | 4 nm | 0.1 nm/sec |
| Ag | 100 nm | 0.1 nm/sec |
| $V_{OC}$ | 560 mV | |
| $J_{SC}$ | 6.6 mA/cm$^2$ | |
| FF | 54% | |
| η | 2.0% | |

The invention claimed is:
1. An organic solar cell comprising a substrate comprising at least one cathode, at least one anode and a charge transport material or absorber material comprising at least one compound represented by formulae Ia or Ib or a mixture thereof,

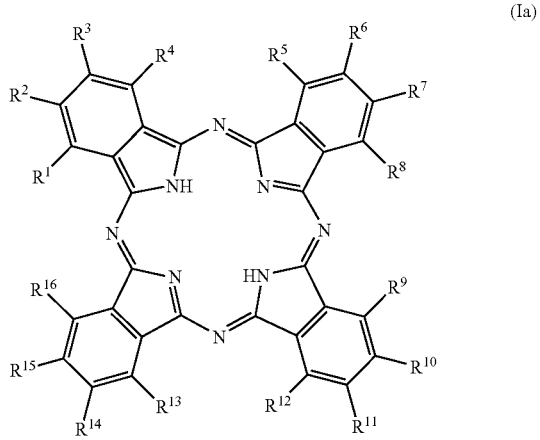

(Ia)

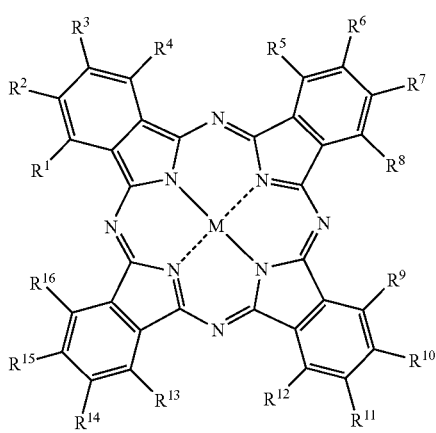

where
from 1 to 12 of the $R^1$ to $R^{16}$ radicals are each halogen and the others are each hydrogen, and M in the formula Ib is a divalent metal, a divalent metal atom group or a divalent metalloid group as a photoactive material in combination with at least one further different semiconductor material comprising 1,6,7,12-tetrachloroperylene-3,4:9,10-tetracarboximide.

2. An organic solar cell comprising a substrate comprising at least one cathode, at least one anode and a charge transport material or absorber material comprising at least one compound represented by formulae Ia or Ib or a mixture thereof,

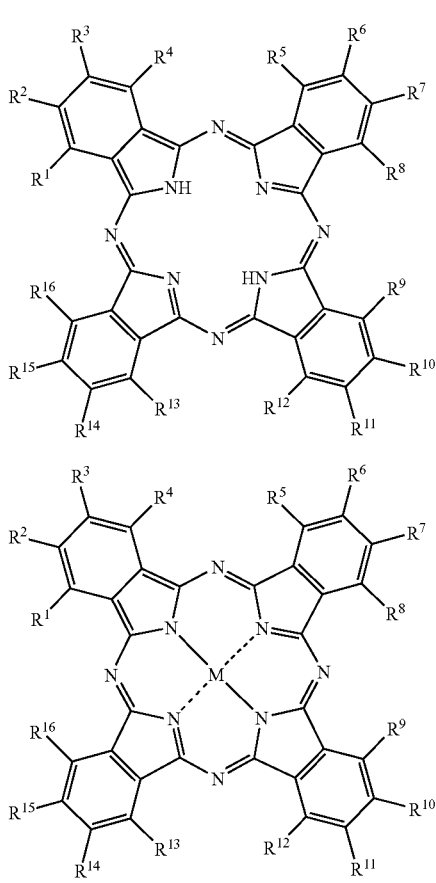

where
from 1 to 12 of the $R^1$ to $R^{16}$ radicals are each halogen and the others are each hydrogen, and M in the formula Ib is a divalent metal, a divalent metal atom group or a divalent metalloid group as a photoactive material in combination with at least one further different semiconductor material comprises a material selected from the group consisting of at least one fullerene, a fullerene derivative or a mixture thereof.

3. The organic solar cell according to claim 2, wherein M in formula Ib is a divalent metal.

4. The c organic solar cell according to claim 2, wherein 1 to 10 of the $R^1$ to $R^{16}$ radicals are each halogen and the others are each hydrogen.

5. The organic solar cell according to claim 2, wherein 4 of the $R^1$ to $R^{16}$ radicals are each halogen and the others are each hydrogen.

6. The organic solar cell according to claim 2, wherein 8 of the $R^1$ to $R^{16}$ radicals are each halogen and the others are each hydrogen.

7. The organic solar cell according to claim 2, wherein the $R^1$ to $R^{16}$ radicals which are halogen are all F or are all Cl.

8. The organic solar cell according to claim 2, wherein M in the formula Ib is Cu or Zn.

9. The organic solar cell according to claim 2, wherein M in the formula Ib is a divalent halogenometal moiety.

10. The organic solar cell according to claim 2, wherein the further semiconductor material comprises C60.

11. The organic solar cell according to claim 2, wherein the further semiconductor material comprises at least one rylene.

12. The organic solar cell according to claim 2, wherein the compound-represented by formulae Ia or Ib and said further different semiconductor material are present in combination with at least one dopant.

13. The organic solar cell according to claim 2, wherein the organic solar cell is a tandem solar cell.

14. The organic solar cell according to claim 13 having at least one donor-acceptor junction in the form of a flat junction.

15. The organic solar cell according to claim 13 having at least one donor-acceptor junction in the form of a bulk heterojunction.

16. The organic solar cell according to claim 2 in the form of a tandem cell comprising a subcell, which comprises at least one compound represented by formulae Ia or Ib, or mixtures thereof, and at least one fullerene or fullerene derivative.

17. The organic solar cell according to claim 2, in the form of a tandem cell comprising a subcell, which comprises at least one compound represented by formulae Ia or Ib, or mixtures thereof, and C60.

18. The organic solar cell according to claim 12, wherein said at least one dopant is at least one dopant selected from pyronin B, rhodamine, 3,6-difluoro-2,5,7,7,8,8-hexacyano-quinodimethane and combinations thereof.

19. The organic solar cell according to claim 2, wherein M in the formula Ib is Al(III)Cl or Al(III)F.

20. The organic solar cell according to claim 2, wherein said compound represented by formulae Ia or Ib is at least one compound selected from the group consisting of 2,3,6,7,10,11,14,15-octafluorocopper phthalocyanine

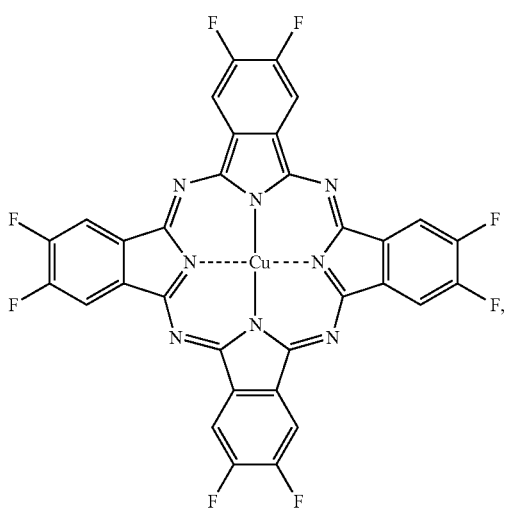

a mixture of tetrafluorocopper phthalocyanines of the following formula

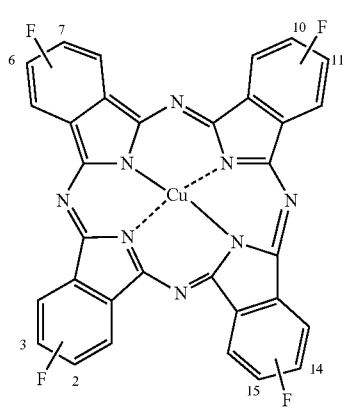

where each isomer has a first fluorine substituent in the 2 or 3 position, a second fluorine substituent in the 6 or 7 position, a third fluorine substituent in the 10 or 11 position and a fourth fluorine substituent in the 14 or 15 position, a mixture of ortho-tetrafluorocopper phthalocyanines of the following formula

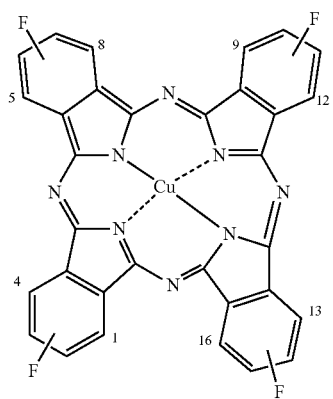

where each isomer has a first fluorine substituent in the 1 or 4 position, a second fluorine substituent in the 5 or 8 position, a third fluorine substituent in the 9 or 12 position and a fourth fluorine substituent in the 13 or 16 position, a mixture of tetrafluorocopper phthalocyanines of the following formula

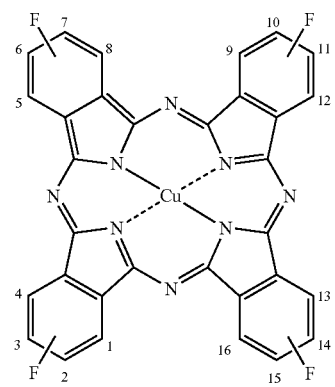

in which each isomer has a first fluorine substituent in the 1 or 2 or 3 or 4 position, a second fluorine substituent in the 5 or 6 or 7 or 8 position, a third fluorine substituent in the 9 or 10 or 11 or 12 position and a fourth fluorine substituent in the 13 or 14 or 15 or 16 position, a mixture of meta-tetrafluorozinc phthalocyanines of the following formula

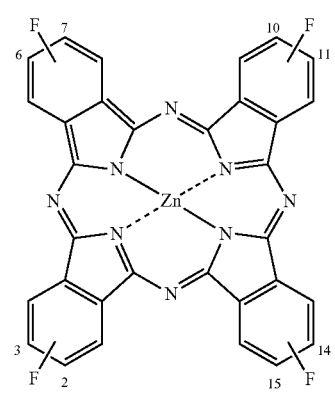

in which each isomer has a first fluorine substituent in the 2 or 3 position, a second fluorine substituent in the 6 or 7 position, a third fluorine substituent in the 10 or 11 position and a fourth fluorine substituent in the 14 or 15 position, a mixture of ortho-tetrafluorozinc phthalocyanines of the following formula

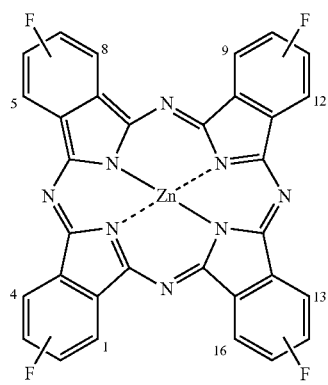

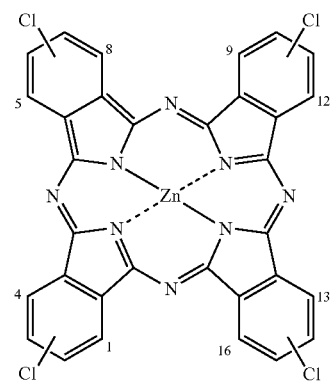

in which each isomer has a first fluorine substituent in the 1 or 4 position, a second fluorine substituent in the 5 or 8 position, a third fluorine substituent in the 9 or 12 position and a fourth fluorine substituent in the 13 or 16 position,
a mixture of ortho-tetrachlorozinc phthalocyanines of the following formula in which each isomer has a first chlorine substituent in the 1 or 4 position, a second chlorine substituent in the 5 or 8 position, a third chlorine substituent in the 9 or 12 position and a fourth chlorine substituent in the 13 or 16 position.

\* \* \* \* \*